(12) United States Patent
Abbott et al.

(10) Patent No.: US 8,758,401 B2
(45) Date of Patent: *Jun. 24, 2014

(54) SYSTEMS AND METHODS FOR TREATING SEPTAL DEFECTS

(75) Inventors: Ryan Abbott, San Jose, CA (US); W. Martin Belef, San Jose, CA (US); Dean Carson, Mountain View, CA (US); Rajiv Doshi, Stanford, CA (US); Ronald J. Jabba, Redwood City, CA (US)

(73) Assignee: Promed, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/250,671

(22) Filed: Sep. 30, 2011

(65) Prior Publication Data

US 2012/0022587 A1 Jan. 26, 2012

Related U.S. Application Data

(60) Continuation of application No. 12/725,595, filed on Mar. 17, 2010, now abandoned, which is a continuation of application No. 11/422,871, filed on Jun. 7, 2006, now Pat. No. 7,686,828, which is a division of application No. 11/175,814, filed on Jul. 5, 2005, now abandoned, which is a continuation-in-part of application No. 10/847,747, filed on May 17, 2004, now abandoned, which is a continuation-in-part of application No. 10/734,670, filed on Dec. 11, 2003, now Pat. No. 8,070,826, which is a division of application No. 09/948,453, filed on Sep. 7, 2001, now Pat. No. 6,702,835, which is a continuation-in-part of application No. 09/948,502, filed on Sep. 6, 2001, now Pat. No. 6,776,784.

(51) Int. Cl.
*A61D 1/00* (2006.01)

(52) U.S. Cl.
USPC .......................................................... 606/213

(58) Field of Classification Search
CPC ................. A61B 17/0057; A61B 2017/00575; A61B 2017/00623
USPC .......... 606/213, 139, 142, 143, 151, 185, 215
See application file for complete search history.

(56) References Cited

U.S. PATENT DOCUMENTS

| 2,670,673 A | 3/1954 | Gordon et al. |
| 3,874,388 A | 4/1975 | King et al. |

(Continued)

FOREIGN PATENT DOCUMENTS

| DE | 4222291 C1 | 7/1992 |
| EP | 0432320 A1 | 6/1991 |

(Continued)

OTHER PUBLICATIONS

Baim, D., "Chapter 4: Percutaneous Approach, Including Transseptal and Apical Puncture", Grossman's Cardiac Catheterization, Angiography, and Intervention, 6th Ed., 2000, pp. 69-100.

(Continued)

*Primary Examiner* — Darwin Erezo
*Assistant Examiner* — Lindsey Bachman
(74) *Attorney, Agent, or Firm* — Mark Stirrat; ONE LLP

(57) ABSTRACT

A system for treating a septal defect having an implantable treatment apparatus and devices for delivering the implantable treatment apparatus and methods for treating a septal defect are provided. The implantable treatment apparatus is preferably implantable through a septal wall or portion thereof. The treatment system can include a flexible elongate body member, a delivery device configured to deliver the implantable apparatus, a stabilization device configured to stabilize the body member and a positioning device configured to position the delivery device in a desired location.

15 Claims, 52 Drawing Sheets

(56) References Cited

U.S. PATENT DOCUMENTS

| | | |
|---|---|---|
| 3,875,648 A | 4/1975 | Bone |
| 4,006,747 A | 2/1977 | Kronenthal et al. |
| 4,007,743 A | 2/1977 | Blake |
| 4,316,469 A | 2/1982 | Kapitanov |
| 4,576,162 A | 3/1986 | McCorkle |
| 4,601,718 A | 7/1986 | Possis et al. |
| 4,665,906 A | 5/1987 | Jervis |
| 4,669,473 A | 6/1987 | Richards et al. |
| 4,696,300 A | 9/1987 | Anderson |
| 4,702,250 A | 10/1987 | Ovil et al. |
| 4,705,040 A | 11/1987 | Mueller et al. |
| 4,721,115 A | 1/1988 | Owens |
| 4,741,336 A | 5/1988 | Failla et al. |
| 4,779,616 A | 10/1988 | Johnson |
| 4,800,890 A | 1/1989 | Cramer |
| 4,802,478 A | 2/1989 | Powell |
| 4,836,204 A | 6/1989 | Landymore et al. |
| 4,850,960 A | 7/1989 | Grayzel |
| 4,861,336 A | 8/1989 | Helzel |
| 4,878,893 A | 11/1989 | Chin |
| 4,892,098 A | 1/1990 | Sauer |
| 4,902,508 A | 2/1990 | Badylak et al. |
| 4,917,089 A | 4/1990 | Sideris |
| 4,929,246 A | 5/1990 | Sinofsky |
| 4,946,467 A | 8/1990 | Ohi et al. |
| 4,985,014 A | 1/1991 | Orejola |
| 4,994,069 A | 2/1991 | Ritchart et al. |
| 5,021,059 A | 6/1991 | Kensey et al. |
| 5,037,433 A | 8/1991 | Wilk et al. |
| 5,041,129 A | 8/1991 | Hayhurst et al. |
| 5,049,153 A | 9/1991 | Nakao et al. |
| 5,067,957 A | 11/1991 | Jervis |
| 5,073,166 A | 12/1991 | Parks et al. |
| 5,108,420 A | 4/1992 | Marks |
| 5,112,310 A | 5/1992 | Grobe |
| 5,171,218 A | 12/1992 | Fonger et al. |
| 5,171,259 A | 12/1992 | Inoue |
| 5,190,050 A | 3/1993 | Nitzsche |
| 5,190,528 A | 3/1993 | Fonger et al. |
| 5,190,546 A | 3/1993 | Jervis |
| 5,192,301 A | 3/1993 | Kamiya et al. |
| 5,219,358 A | 6/1993 | Bendel et al. |
| 5,222,974 A | 6/1993 | Kensey et al. |
| 5,236,440 A | 8/1993 | Hlavacek |
| 5,242,427 A | 9/1993 | Bilweis |
| 5,250,054 A | 10/1993 | Li |
| 5,250,055 A | 10/1993 | Moore et al. |
| 5,257,637 A | 11/1993 | El Gazayerli |
| 5,281,234 A | 1/1994 | Wilk et al. |
| 5,282,827 A | 2/1994 | Kensey et al. |
| 5,284,488 A | 2/1994 | Sideris |
| 5,290,272 A | 3/1994 | Burstein et al. |
| 5,290,278 A | 3/1994 | Anderson |
| 5,300,065 A | 4/1994 | Anderson |
| 5,304,184 A | 4/1994 | Hathaway et al. |
| 5,304,185 A | 4/1994 | Taylor |
| 5,312,341 A | 5/1994 | Turi |
| 5,312,435 A | 5/1994 | Nash et al. |
| 5,318,525 A | 6/1994 | West et al. |
| 5,330,488 A | 7/1994 | Goldrath |
| 5,330,496 A | 7/1994 | Alferness |
| 5,334,191 A | 8/1994 | Poppas et al. |
| 5,334,217 A | 8/1994 | Das |
| 5,357,979 A | 10/1994 | Imran |
| 5,364,410 A | 11/1994 | Failla et al. |
| 5,370,679 A | 12/1994 | Atlee, III |
| 5,383,852 A | 1/1995 | Stevens-Wright |
| 5,387,227 A | 2/1995 | Grice |
| 5,394,880 A | 3/1995 | Atlee, III |
| 5,403,329 A | 4/1995 | Hinchcliffe |
| 5,403,338 A | 4/1995 | Milo |
| 5,409,469 A | 4/1995 | Schaerf |
| 5,409,481 A | 4/1995 | Poppas et al. |
| 5,413,584 A | 5/1995 | Schulze |
| 5,417,699 A | 5/1995 | Klein et al. |
| 5,417,713 A | 5/1995 | Cohen |
| 5,421,338 A | 6/1995 | Crowley et al. |
| 5,425,744 A | 6/1995 | Fagan et al. |
| 5,431,696 A | 7/1995 | Atlee, III |
| 5,433,727 A | 7/1995 | Sideris |
| 5,441,504 A | 8/1995 | Pohndorf et al. |
| 5,443,478 A | 8/1995 | Purdy |
| 5,451,235 A | 9/1995 | Lock et al. |
| 5,461,235 A | 10/1995 | Cottrell et al. |
| 5,462,560 A | 10/1995 | Stevens |
| 5,462,561 A | 10/1995 | Voda |
| 5,474,573 A | 12/1995 | Hatcher |
| 5,478,353 A | 12/1995 | Yoon |
| 5,486,183 A | 1/1996 | Middleman et al. |
| 5,486,193 A | 1/1996 | Bourne et al. |
| 5,503,634 A | 4/1996 | Christy |
| 5,507,744 A | 4/1996 | Tay et al. |
| 5,507,811 A | 4/1996 | Koike et al. |
| 5,522,873 A | 6/1996 | Jackman et al. |
| 5,527,388 A | 6/1996 | Berke et al. |
| 5,545,138 A | 8/1996 | Fugoso et al. |
| 5,548,872 A | 8/1996 | Oetiker |
| 5,554,162 A | 9/1996 | DeLange |
| 5,570,671 A | 11/1996 | Hickey |
| 5,573,540 A | 11/1996 | Yoon |
| 5,573,542 A | 11/1996 | Stevens |
| 5,575,772 A | 11/1996 | Lennox |
| 5,577,299 A | 11/1996 | Thompson et al. |
| 5,578,045 A | 11/1996 | Das |
| 5,582,616 A | 12/1996 | Bolduc et al. |
| 5,584,803 A | 12/1996 | Stevens et al. |
| 5,601,571 A | 2/1997 | Moss |
| 5,605,696 A | 2/1997 | Eury et al. |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,645,557 A | 7/1997 | Yoon |
| 5,649,950 A | 7/1997 | Bourne et al. |
| 5,658,280 A | 8/1997 | Issa |
| 5,662,621 A | 9/1997 | Lafontaine |
| 5,662,643 A | 9/1997 | Kung et al. |
| 5,682,906 A | 11/1997 | Sterman et al. |
| 5,702,368 A | 12/1997 | Stevens et al. |
| 5,702,421 A | 12/1997 | Schneidt |
| 5,709,224 A | 1/1998 | Behl et al. |
| 5,709,707 A | 1/1998 | Lock et al. |
| 5,713,867 A | 2/1998 | Morris |
| 5,713,911 A | 2/1998 | Racenet et al. |
| 5,714,297 A | 2/1998 | Chamberlain et al. |
| 5,716,367 A | 2/1998 | Koike et al. |
| 5,720,754 A | 2/1998 | Middleman et al. |
| 5,722,981 A | 3/1998 | Stevens |
| 5,725,512 A | 3/1998 | Swartz et al. |
| 5,725,552 A | 3/1998 | Kotula et al. |
| 5,725,554 A | 3/1998 | Simon et al. |
| 5,728,151 A | 3/1998 | Garrison et al. |
| 5,733,294 A | 3/1998 | Forber et al. |
| 5,738,652 A | 4/1998 | Boyd et al. |
| 5,741,429 A | 4/1998 | Donadio, III et al. |
| 5,755,778 A | 5/1998 | Kleshinski |
| 5,759,170 A | 6/1998 | Peters |
| 5,769,812 A | 6/1998 | Stevens et al. |
| 5,772,672 A | 6/1998 | Toy et al. |
| 5,776,162 A | 7/1998 | Kleshinski |
| 5,782,860 A | 7/1998 | Epstein et al. |
| 5,792,094 A | 8/1998 | Stevens et al. |
| 5,797,960 A | 8/1998 | Stevens et al. |
| 5,807,339 A | 9/1998 | Bostrom et al. |
| 5,810,882 A | 9/1998 | Bolduc et al. |
| 5,810,884 A | 9/1998 | Kim |
| 5,814,016 A | 9/1998 | Valley et al. |
| 5,814,068 A | 9/1998 | Koike et al. |
| 5,814,097 A | 9/1998 | Sterman et al. |
| 5,823,956 A | 10/1998 | Roth et al. |
| 5,827,216 A | 10/1998 | Igo et al. |
| 5,829,447 A | 11/1998 | Stevens et al. |
| 5,836,311 A | 11/1998 | Borst et al. |
| 5,853,422 A | 12/1998 | Huebsch et al. |

(56) References Cited

U.S. PATENT DOCUMENTS

| | | |
|---|---|---|
| 5,855,614 A | 1/1999 | Stevens et al. |
| 5,861,003 A | 1/1999 | Latson et al. |
| 5,865,791 A | 2/1999 | Whayne et al. |
| 5,868,702 A | 2/1999 | Stevens et al. |
| 5,868,733 A | 2/1999 | Ockuly et al. |
| 5,868,753 A | 2/1999 | Schatz |
| 5,879,499 A | 3/1999 | Corvi |
| 5,885,238 A | 3/1999 | Stevens et al. |
| 5,893,856 A | 4/1999 | Jacob et al. |
| 5,895,404 A | 4/1999 | Ruiz |
| 5,902,319 A | 5/1999 | Daley |
| 5,904,703 A | 5/1999 | Gilson |
| 5,908,428 A | 6/1999 | Scirica et al. |
| 5,910,150 A | 6/1999 | Saadat |
| 5,911,717 A | 6/1999 | Jacobsen et al. |
| 5,913,810 A | 6/1999 | Andre |
| 5,913,842 A | 6/1999 | Boyd et al. |
| 5,919,200 A | 7/1999 | Stambaugh et al. |
| 5,924,424 A | 7/1999 | Stevens et al. |
| 5,927,284 A | 7/1999 | Borst et al. |
| 5,928,181 A | 7/1999 | Coleman et al. |
| 5,928,250 A | 7/1999 | Koike et al. |
| 5,931,848 A | 8/1999 | Saadat |
| 5,941,899 A | 8/1999 | Granger et al. |
| 5,944,738 A | 8/1999 | Amplatz et al. |
| 5,947,997 A | 9/1999 | Pavcnik et al. |
| 5,955,110 A | 9/1999 | Patel et al. |
| 5,967,977 A | 10/1999 | Mullis et al. |
| 5,972,013 A | 10/1999 | Schmidt |
| 5,976,174 A | 11/1999 | Ruiz |
| 5,980,503 A | 11/1999 | Chin |
| 5,989,268 A | 11/1999 | Pugsley, Jr. et al. |
| 5,993,475 A | 11/1999 | Lin et al. |
| 6,007,563 A | 12/1999 | Nash et al. |
| 6,010,517 A | 1/2000 | Baccaro |
| 6,013,052 A | 1/2000 | Durman et al. |
| 6,015,378 A | 1/2000 | Borst et al. |
| 6,015,417 A | 1/2000 | Reynolds, Jr. |
| 6,024,756 A | 2/2000 | Huebsch et al. |
| 6,027,476 A | 2/2000 | Sterman et al. |
| 6,030,007 A | 2/2000 | Bassily et al. |
| 6,036,699 A | 3/2000 | Andreas et al. |
| 6,036,720 A | 3/2000 | Abrams et al. |
| 6,056,760 A | 5/2000 | Koike et al. |
| 6,071,271 A | 6/2000 | Baker et al. |
| 6,071,292 A | 6/2000 | Makower et al. |
| 6,077,281 A | 6/2000 | Das |
| 6,077,291 A | 6/2000 | Das |
| 6,079,414 A | 6/2000 | Roth |
| 6,080,182 A | 6/2000 | Shaw et al. |
| 6,090,084 A | 7/2000 | Hassett et al. |
| 6,090,096 A | 7/2000 | St. Goar et al. |
| 6,093,199 A | 7/2000 | Brown et al. |
| 6,095,997 A | 8/2000 | French et al. |
| 6,110,145 A | 8/2000 | Macoviak |
| 6,113,609 A | 9/2000 | Adams |
| 6,113,610 A | 9/2000 | Poncet |
| 6,113,611 A | 9/2000 | Allen et al. |
| 6,117,145 A | 9/2000 | Wood et al. |
| 6,117,159 A | 9/2000 | Huebsch et al. |
| 6,126,658 A | 10/2000 | Baker |
| 6,127,410 A | 10/2000 | Duhaylongsod |
| 6,132,438 A | 10/2000 | Fleischman et al. |
| 6,135,981 A | 10/2000 | Dyke |
| 6,142,975 A | 11/2000 | Jalisi et al. |
| 6,149,664 A | 11/2000 | Kurz |
| 6,152,141 A | 11/2000 | Stevens et al. |
| 6,152,144 A | 11/2000 | Lesh et al. |
| 6,162,195 A | 12/2000 | Igo et al. |
| 6,162,202 A | 12/2000 | Sicurelli et al. |
| 6,165,183 A | 12/2000 | Kuehn et al. |
| 6,165,204 A | 12/2000 | Levinson et al. |
| 6,171,329 B1 | 1/2001 | Shaw et al. |
| 6,171,338 B1 | 1/2001 | Talja et al. |
| 6,174,322 B1 | 1/2001 | Schneidt |
| 6,179,809 B1 | 1/2001 | Khairkhahan et al. |
| 6,187,039 B1 | 2/2001 | Hiles et al. |
| 6,200,313 B1 | 3/2001 | Abe et al. |
| 6,206,895 B1 | 3/2001 | Levinson |
| 6,206,907 B1 | 3/2001 | Marino et al. |
| 6,214,029 B1 | 4/2001 | Thill et al. |
| 6,221,092 B1 | 4/2001 | Koike et al. |
| 6,231,561 B1 | 5/2001 | Frazier et al. |
| 6,245,080 B1 | 6/2001 | Levinson |
| 6,254,550 B1 | 7/2001 | McNamara et al. |
| 6,270,490 B1 | 8/2001 | Hahnen |
| 6,270,515 B1 | 8/2001 | Linden et al. |
| 6,275,730 B1 | 8/2001 | KenKnight et al. |
| 6,277,138 B1 | 8/2001 | Levinson et al. |
| 6,277,139 B1 | 8/2001 | Levinson et al. |
| 6,280,432 B1 | 8/2001 | Turovskiy et al. |
| 6,280,460 B1 | 8/2001 | Bolduc et al. |
| 6,287,317 B1 | 9/2001 | Makower et al. |
| 6,290,674 B1 | 9/2001 | Roue et al. |
| 6,293,920 B1 | 9/2001 | Sweezer et al. |
| 6,302,903 B1 | 10/2001 | Mulier et al. |
| 6,305,378 B1 | 10/2001 | Lesh |
| 6,306,150 B1 | 10/2001 | Levinson |
| 6,306,424 B1 | 10/2001 | Vyakarnam et al. |
| 6,308,090 B1 | 10/2001 | Tu et al. |
| 6,309,415 B1 | 10/2001 | Pulnev et al. |
| 6,312,446 B1 | 11/2001 | Huebsch et al. |
| 6,319,263 B1 | 11/2001 | Levinson |
| 6,322,548 B1 | 11/2001 | Payne et al. |
| 6,328,727 B1 | 12/2001 | Frazier et al. |
| 6,336,898 B1 | 1/2002 | Borst et al. |
| 6,342,064 B1 | 1/2002 | Koike et al. |
| 6,346,074 B1 | 2/2002 | Roth |
| 6,346,099 B1 | 2/2002 | Altman |
| 6,346,112 B2 | 2/2002 | Adams |
| 6,350,229 B1 | 2/2002 | Borst et al. |
| 6,352,531 B1 | 3/2002 | O'Connor et al. |
| 6,352,552 B1 | 3/2002 | Levinson et al. |
| 6,355,052 B1 | 3/2002 | Neuss et al. |
| 6,364,826 B1 | 4/2002 | Borst et al. |
| 6,371,906 B1 | 4/2002 | Borst et al. |
| 6,375,671 B1 | 4/2002 | Kobayashi et al. |
| 6,379,368 B1 | 4/2002 | Corcoran et al. |
| 6,387,104 B1 | 5/2002 | Pugsley, Jr. et al. |
| 6,394,948 B1 | 5/2002 | Borst et al. |
| 6,398,796 B2 | 6/2002 | Levinson |
| 6,401,720 B1 | 6/2002 | Stevens et al. |
| 6,402,772 B1 | 6/2002 | Amplatz et al. |
| 6,416,493 B1 | 7/2002 | Del Giglio |
| 6,419,669 B1 | 7/2002 | Frazier et al. |
| 6,432,059 B2 | 8/2002 | Hickey |
| 6,436,088 B2 | 8/2002 | Frazier et al. |
| 6,440,152 B1 | 8/2002 | Gainor et al. |
| 6,458,100 B2 | 10/2002 | Roue et al. |
| 6,464,640 B1 | 10/2002 | Guracar et al. |
| 6,464,645 B1 | 10/2002 | Park et al. |
| 6,482,224 B1 | 11/2002 | Michler et al. |
| 6,482,228 B1 | 11/2002 | Norred |
| 6,485,504 B1 | 11/2002 | Johnson et al. |
| 6,488,706 B1 | 12/2002 | Solymar |
| 6,497,698 B1 | 12/2002 | Fonger et al. |
| 6,506,205 B2 | 1/2003 | Goldberg et al. |
| 6,532,388 B1 | 3/2003 | Hill et al. |
| 6,537,300 B2 | 3/2003 | Girton |
| 6,551,272 B2 | 4/2003 | Göbel |
| 6,551,303 B1 | 4/2003 | Van Tassel et al. |
| 6,551,344 B2 | 4/2003 | Thill |
| 6,560,489 B2 | 5/2003 | Hauck |
| 6,562,051 B1 | 5/2003 | Bolduc et al. |
| 6,562,052 B2 | 5/2003 | Nobles et al. |
| 6,572,593 B1 | 6/2003 | Daum |
| 6,579,259 B2 | 6/2003 | Stevens et al. |
| 6,585,716 B2 | 7/2003 | Altman |
| 6,592,552 B1 | 7/2003 | Schmidt |
| 6,592,557 B2 | 7/2003 | Barbut |
| 6,596,013 B2 | 7/2003 | Yang et al. |
| 6,606,513 B2 | 8/2003 | Lardo et al. |
| 6,613,062 B1 | 9/2003 | Leckrone et al. |
| 6,623,508 B2 | 9/2003 | Shaw et al. |

(56) References Cited

U.S. PATENT DOCUMENTS

| | | |
|---|---|---|
| 6,623,518 B2 | 9/2003 | Thompson et al. |
| 6,626,841 B1 | 9/2003 | Atlee, III |
| 6,626,890 B2 | 9/2003 | Nguyen et al. |
| 6,626,899 B2 | 9/2003 | Houser et al. |
| 6,626,930 B1 | 9/2003 | Allen et al. |
| 6,629,534 B1 | 10/2003 | Dell et al. |
| 6,632,223 B1 | 10/2003 | Keane |
| 6,645,225 B1 | 11/2003 | Atkinson |
| 6,650,923 B1 | 11/2003 | Lesh et al. |
| 6,651,672 B2 | 11/2003 | Roth |
| 6,656,206 B2 | 12/2003 | Corcoran et al. |
| 6,659,981 B2 | 12/2003 | Stewart et al. |
| 6,662,045 B2 | 12/2003 | Ideker et al. |
| 6,663,639 B1 | 12/2003 | Laufer et al. |
| 6,666,861 B1 | 12/2003 | Grabek |
| 6,679,268 B2 | 1/2004 | Stevens et al. |
| 6,685,728 B2 | 2/2004 | Sinnott et al. |
| 6,689,062 B1 | 2/2004 | Mesallum |
| 6,692,471 B2 | 2/2004 | Boudreaux |
| 6,692,512 B2 | 2/2004 | Jang |
| 6,695,838 B2 | 2/2004 | Wellman et al. |
| 6,699,231 B1 | 3/2004 | Sterman et al. |
| 6,702,835 B2 | 3/2004 | Ginn |
| 6,706,033 B1 | 3/2004 | Martinez et al. |
| 6,706,047 B2 | 3/2004 | Tanner et al. |
| 6,712,804 B2 | 3/2004 | Roue et al. |
| 6,712,836 B1 | 3/2004 | Berg et al. |
| 6,726,662 B2 | 4/2004 | Altman |
| 6,730,061 B1 | 5/2004 | Cuschieri et al. |
| 6,735,471 B2 | 5/2004 | Hill et al. |
| 6,736,828 B1 | 5/2004 | Adams et al. |
| 6,746,404 B2 | 6/2004 | Schwartz |
| 6,746,456 B2 | 6/2004 | Xiao |
| 6,749,617 B1 | 6/2004 | Palasis et al. |
| 6,773,441 B1 | 8/2004 | Laufer et al. |
| 6,776,784 B2 | 8/2004 | Ginn |
| 6,776,797 B1 | 8/2004 | Blom et al. |
| 6,783,499 B2 | 8/2004 | Schwartz |
| 6,790,218 B2 | 9/2004 | Jayaraman |
| 6,802,840 B2 | 10/2004 | Chin et al. |
| 6,821,265 B1 | 11/2004 | Bertolero et al. |
| 6,840,246 B2 | 1/2005 | Downing |
| 6,854,467 B2 | 2/2005 | Boekstegers |
| 6,855,116 B2 | 2/2005 | Atlee, III |
| 6,866,650 B2 | 3/2005 | Stevens et al. |
| 6,878,118 B2 | 4/2005 | Atlee, III |
| 6,882,883 B2 | 4/2005 | Condie et al. |
| 6,889,694 B2 | 5/2005 | Hooven |
| 6,899,704 B2 | 5/2005 | Sterman et al. |
| 6,902,545 B2 | 6/2005 | Bertolero et al. |
| 6,913,600 B2 | 7/2005 | Valley et al. |
| 6,913,607 B2 | 7/2005 | Ainsworth et al. |
| 6,915,149 B2 | 7/2005 | Ben-Haim |
| 6,918,890 B2 | 7/2005 | Schmidt |
| 6,918,908 B2 | 7/2005 | Bonner et al. |
| 6,929,011 B2 | 8/2005 | Knudson et al. |
| 6,932,792 B1 | 8/2005 | St. Goar et al. |
| 6,932,811 B2 | 8/2005 | Hooven et al. |
| 6,934,583 B2 | 8/2005 | Weinberg et al. |
| 6,939,348 B2 | 9/2005 | Malecki et al. |
| 6,939,361 B1 | 9/2005 | Kleshinski |
| 6,952,613 B2 | 10/2005 | Swoyer et al. |
| 6,953,466 B2 | 10/2005 | Palasis et al. |
| 6,955,175 B2 | 10/2005 | Stevens et al. |
| 6,960,220 B2 | 11/2005 | Marino et al. |
| 6,971,998 B2 | 12/2005 | Rosenman et al. |
| 6,976,990 B2 | 12/2005 | Mowry |
| 6,991,635 B2 | 1/2006 | Takamoto et al. |
| 6,994,094 B2 | 2/2006 | Schwartz |
| 6,994,713 B2 | 2/2006 | Berg et al. |
| 7,001,415 B2 | 2/2006 | Hooven |
| 7,004,952 B2 | 2/2006 | Nobles et al. |
| 7,018,390 B2 | 3/2006 | Turovskiy et al. |
| 7,020,518 B2 | 3/2006 | Zheng et al. |
| 7,039,467 B2 | 5/2006 | Hauck |
| 7,044,135 B2 | 5/2006 | Lesh |
| 7,048,733 B2 | 5/2006 | Hartley et al. |
| 7,056,331 B2 | 6/2006 | Kaplan et al. |
| 7,083,628 B2 | 8/2006 | Bachman |
| 7,087,072 B2 | 8/2006 | Marino et al. |
| 7,090,683 B2 | 8/2006 | Brock et al. |
| 7,090,686 B2 | 8/2006 | Nobles et al. |
| 7,094,244 B2 | 8/2006 | Schreck |
| 7,097,653 B2 | 8/2006 | Freudenthal et al. |
| 7,101,395 B2 | 9/2006 | Tremulis et al. |
| 7,108,660 B2 | 9/2006 | Stephens et al. |
| 7,112,219 B2 | 9/2006 | Vidlund et al. |
| 7,113,831 B2 | 9/2006 | Hooven |
| 7,115,135 B2 | 10/2006 | Corcoran et al. |
| 7,186,251 B2 | 3/2007 | Malecki et al. |
| 7,288,105 B2 | 10/2007 | Oman et al. |
| 7,320,692 B1 | 1/2008 | Bender et al. |
| 7,507,252 B2 | 3/2009 | Lashinski et al. |
| 7,618,426 B2 * | 11/2009 | Ewers et al. ............ 606/139 |
| 7,736,374 B2 * | 6/2010 | Vaughan et al. ......... 606/153 |
| 2001/0014800 A1 | 8/2001 | Frazier et al. |
| 2001/0034537 A1 | 10/2001 | Shaw et al. |
| 2001/0037129 A1 | 11/2001 | Thill |
| 2001/0039435 A1 | 11/2001 | Roue et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0026208 A1 | 2/2002 | Roe et al. |
| 2002/0032462 A1 | 3/2002 | Houser et al. |
| 2002/0035361 A1 | 3/2002 | Houser et al. |
| 2002/0035374 A1 | 3/2002 | Borillo et al. |
| 2002/0039048 A1 | 4/2002 | Matsuge |
| 2002/0043307 A1 | 4/2002 | Ishida et al. |
| 2002/0052572 A1 | 5/2002 | Franco et al. |
| 2002/0077555 A1 | 6/2002 | Schwartz |
| 2002/0096183 A1 | 7/2002 | Stevens et al. |
| 2002/0099389 A1 | 7/2002 | Michler et al. |
| 2002/0099437 A1 | 7/2002 | Anson et al. |
| 2002/0107531 A1 | 8/2002 | Schreck et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0138095 A1 | 9/2002 | Mazzocchi et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0025421 A1 | 2/2003 | Ebihara et al. |
| 2003/0028213 A1 | 2/2003 | Thill et al. |
| 2003/0033006 A1 | 2/2003 | Phillips et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0059640 A1 | 3/2003 | Marton et al. |
| 2003/0100920 A1 | 5/2003 | Akin et al. |
| 2003/0139819 A1 | 7/2003 | Beer et al. |
| 2003/0144694 A1 | 7/2003 | Chanduszko et al. |
| 2003/0167071 A1 | 9/2003 | Martin et al. |
| 2003/0191495 A1 | 10/2003 | Ryan et al. |
| 2003/0195530 A1 | 10/2003 | Thill |
| 2003/0195555 A1 | 10/2003 | Khairkhahan et al. |
| 2003/0204203 A1 | 10/2003 | Khairkhahan et al. |
| 2003/0208232 A1 | 11/2003 | Blaeser et al. |
| 2003/0225421 A1 | 12/2003 | Peavey et al. |
| 2004/0044361 A1 | 3/2004 | Frazier et al. |
| 2004/0073242 A1 | 4/2004 | Chanduszko |
| 2004/0092973 A1 | 5/2004 | Chanduszko et al. |
| 2004/0098042 A1 | 5/2004 | Devellian et al. |
| 2004/0098121 A1 | 5/2004 | Opolski |
| 2004/0133230 A1 | 7/2004 | Carpenter et al. |
| 2004/0133236 A1 | 7/2004 | Chanduszko |
| 2004/0138682 A1 | 7/2004 | Onuki et al. |
| 2004/0162568 A1 | 8/2004 | Saadat et al. |

(56) References Cited

U.S. PATENT DOCUMENTS

| | | |
|---|---|---|
| 2004/0176799 A1 | 9/2004 | Chanduszko et al. |
| 2004/0193185 A1 | 9/2004 | McBrayer |
| 2004/0193194 A1 | 9/2004 | Laufer et al. |
| 2004/0210301 A1 | 10/2004 | Obermiller |
| 2004/0220596 A1 | 11/2004 | Frazier et al. |
| 2004/0225183 A1 | 11/2004 | Michlitsch et al. |
| 2004/0230185 A1 | 11/2004 | Malecki et al. |
| 2004/0243122 A1 | 12/2004 | Auth et al. |
| 2004/0267191 A1 | 12/2004 | Gifford, III et al. |
| 2004/0267306 A1 | 12/2004 | Blaeser et al. |
| 2005/0034735 A1 | 2/2005 | Deem et al. |
| 2005/0043759 A1 | 2/2005 | Chanduszko |
| 2005/0055050 A1 | 3/2005 | Alfaro |
| 2005/0059984 A1* | 3/2005 | Chanduszko et al. ........ 606/151 |
| 2005/0070923 A1 | 3/2005 | McIntosh |
| 2005/0075653 A1 | 4/2005 | Saadat et al. |
| 2005/0080406 A1 | 4/2005 | Malecki et al. |
| 2005/0119675 A1 | 6/2005 | Adams et al. |
| 2005/0125032 A1 | 6/2005 | Whisenant et al. |
| 2005/0131460 A1 | 6/2005 | Gifford et al. |
| 2005/0149066 A1 | 7/2005 | Stafford |
| 2005/0149115 A1 | 7/2005 | Roue et al. |
| 2005/0187568 A1 | 8/2005 | Klenk et al. |
| 2005/0187588 A1 | 8/2005 | Stahmann et al. |
| 2005/0187620 A1 | 8/2005 | Pai et al. |
| 2005/0192626 A1 | 9/2005 | Widomski et al. |
| 2005/0192627 A1 | 9/2005 | Whisenant et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2005/0228434 A1 | 10/2005 | Amplatz et al. |
| 2005/0234509 A1 | 10/2005 | Widomski et al. |
| 2005/0250988 A1 | 11/2005 | Ewers et al. |
| 2005/0251154 A1 | 11/2005 | Chanduszko et al. |
| 2005/0251165 A1 | 11/2005 | Vaughan et al. |
| 2005/0251201 A1 | 11/2005 | Roue et al. |
| 2005/0256532 A1 | 11/2005 | Nayak et al. |
| 2005/0267493 A1 | 12/2005 | Schreck et al. |
| 2005/0267495 A1 | 12/2005 | Ginn et al. |
| 2005/0267523 A1 | 12/2005 | Devellian et al. |
| 2005/0267524 A1 | 12/2005 | Chanduszko |
| 2005/0267525 A1 | 12/2005 | Chanduszko |
| 2005/0267526 A1 | 12/2005 | Wahr et al. |
| 2005/0267529 A1 | 12/2005 | Crockett et al. |
| 2005/0271631 A1 | 12/2005 | Lee et al. |
| 2005/0273119 A1 | 12/2005 | Widomski et al. |
| 2005/0273124 A1 | 12/2005 | Chanduszko |
| 2005/0273135 A1 | 12/2005 | Chanduszko et al. |
| 2005/0277982 A1 | 12/2005 | Marino et al. |
| 2005/0288706 A1 | 12/2005 | Widomski et al. |
| 2005/0288786 A1 | 12/2005 | Chanduszko |
| 2006/0009800 A1 | 1/2006 | Christianson et al. |
| 2006/0015002 A1 | 1/2006 | Moaddeb et al. |
| 2006/0036282 A1 | 2/2006 | Wahr et al. |
| 2006/0036284 A1 | 2/2006 | Blaeser et al. |
| 2006/0052821 A1 | 3/2006 | Abbott et al. |
| 2006/0069408 A1 | 3/2006 | Kato |
| 2006/0079870 A1 | 4/2006 | Barry |
| 2006/0095052 A1 | 5/2006 | Chambers |
| 2006/0122633 A1 | 6/2006 | To et al. |
| 2006/0200197 A1 | 9/2006 | Brenzel et al. |
| 2006/0217764 A1 | 9/2006 | Abbott et al. |
| 2006/0271089 A1 | 11/2006 | Alejandro et al. |
| 2007/0005018 A1 | 1/2007 | Tekbuchava |
| 2007/0010806 A1 | 1/2007 | Malecki et al. |
| 2007/0049970 A1 | 3/2007 | Belef et al. |
| 2007/0073337 A1 | 3/2007 | Abbott et al. |
| 2007/0123851 A1 | 5/2007 | Alejandro et al. |
| 2007/0185530 A1 | 8/2007 | Chin-Chen et al. |
| 2008/0015633 A1 | 1/2008 | Abbott et al. |

FOREIGN PATENT DOCUMENTS

| | | |
|---|---|---|
| EP | 0553259 B1 | 3/1995 |
| EP | 1013227 A2 | 6/2000 |
| EP | 1046375 B1 | 11/2004 |
| EP | 1222897 B1 | 3/2008 |
| JP | 04-22643 | 8/1992 |
| WO | WO 92/05828 | 4/1992 |
| WO | WO 92/06733 | 4/1992 |
| WO | WO 96/25179 A1 | 8/1996 |
| WO | WO 96/31157 A1 | 10/1996 |
| WO | WO 97/42878 A1 | 11/1997 |
| WO | WO 98/02100 A1 | 1/1998 |
| WO | WO 98/07375 A1 | 2/1998 |
| WO | WO 99/02100 A1 | 1/1999 |
| WO | WO 99/18862 | 4/1999 |
| WO | WO 99/18864 | 4/1999 |
| WO | WO 99/18870 | 4/1999 |
| WO | WO 99/18871 | 4/1999 |
| WO | WO 00/07506 A2 | 2/2000 |
| WO | WO 00/27292 A1 | 5/2000 |
| WO | WO 00/35352 A2 | 6/2000 |
| WO | WO 00/44428 A2 | 8/2000 |
| WO | WO 01/21247 A1 | 3/2001 |
| WO | WO 01/49185 A1 | 7/2001 |
| WO | WO 01/78596 A1 | 10/2001 |
| WO | WO 02/024106 A2 | 3/2002 |
| WO | WO 02/062236 A1 | 8/2002 |
| WO | WO 03/059152 A2 | 7/2003 |
| WO | WO 03/063732 A2 | 8/2003 |
| WO | WO 03/077733 A2 | 9/2003 |
| WO | WO 03/094742 A1 | 11/2003 |
| WO | WO 03/103476 A2 | 12/2003 |
| WO | WO 2004/026146 A1 | 4/2004 |
| WO | WO 2004/043266 A2 | 5/2004 |
| WO | WO 2004/052213 A1 | 6/2004 |
| WO | WO 2004/069054 A2 | 8/2004 |
| WO | WO 2004/069055 A2 | 8/2004 |
| WO | WO 2004/086951 A2 | 10/2004 |
| WO | WO 2004/087235 A2 | 10/2004 |
| WO | WO 2005/006990 A2 | 1/2005 |
| WO | WO 2005/027752 A1 | 3/2005 |
| WO | WO 2005/034738 A2 | 4/2005 |
| WO | WO 2005/039419 | 5/2005 |
| WO | WO 2005/074517 A2 | 8/2005 |
| WO | WO 2005/074814 A2 | 8/2005 |
| WO | WO 2005/082255 | 9/2005 |
| WO | WO 2005/092203 | 10/2005 |
| WO | WO 2005/110240 A1 | 11/2005 |
| WO | WO 2005/112779 A1 | 12/2005 |
| WO | WO 2006/036837 A2 | 4/2006 |
| WO | WO 2007/024615 A1 | 3/2007 |
| WO | WO 2008/024489 A2 | 2/2008 |
| WO | WO 2008/153872 A2 | 12/2008 |

OTHER PUBLICATIONS

Daoud, E., et al., " Intracardiac Echocardiography to Guide Transseptal Left Heart Catheterization for Radiofrequency Catheter Ablation", Journal of Cardiovascular.

De Pont!, R., et al., "Trans-septal catheterization for radiofrequency catheter ablation of cardiac arrhythmias", European Heart Journal, vol. 19, 1998, pp. 943-950.

Epstein, L., et al., "Nonfluoroscopic Transseptal Catheterization: Safety and Efficacy of Intracardiac Echocardiographic Guidance", Journal of Cardiovascular Electrophysiology, vol. 9, No. 6, Jun. 1998, pp. 625-630.

Hara, H., et al., " Patent Foramen Ovale: Current Pathology, Pathophysiology, and Clinical Status", Journal of the American College of Cardiology, vol., 46, No. 9, Nov. 2005, pgs. 1768-1776.

Hurrell, D., et al., " Echocardiography in the Invasive Laboratory: Utility of Two- Dimensional Echocardiography in Performing Transseptal Catherization", Mayo Clinic Proc., vol. 73, 1998, pgs. 126-131.

Lesh, M., et al., "Comparison of the Retrograde and Transseptal Methods for Ablation of Left Free Wall Accessory Pathways", Journal of American College of Cardiology, vol. 22, No. 2, Aug. 1993, pgs. 542-549.

(56) References Cited

OTHER PUBLICATIONS

Lundqvist, C., et al., "Transseptal Left Heart Catheterization: a Review of 278 Studies", Clin. Cardiol., vol. 9, Jan. 1986, pgs. 21-26.

Mitchel, J., et al., " Intracardiac Ultrasound Imaging During Transseptal Catheterization", Chest, vol. 108, No. 1, Jul. 1995, pgs. 104-0108.

Montenero, a., et al., "Catheter Ablation of Left Accessory Atrioventricular Connections: the Transseptal Approach", Journal of Interventional Cardiology, vol. 8, No. 6 (Suppl), 1995, pgs. 806-812.

Peckham, G., et al., " Combined Percutaneous Retrograde Aortic and Transseptal Left Heart Catheterization", Brit. Heart Journal, vol. 26, 1964, pgs. 460-468.

Reig, J., et al., "Morphologic characteristics of the fossa ovalis as an anatomic basis for transseptal catheterization", Surg. Radial. Anat., vol. 19, No. 5, 1997, pgs. 279- 282.

Roelke, M., et al., "The Technique and Safety of Transseptal Left Heart Catheterization: the Massachusetts General Hospital Experience With 1,279 Procedures", Catheterization and Cardiovascular Diagnosis, vol. 32, No. 4, Aug. 1994, pgs. 332-339.

Ruiz, C., et al., "The Puncture Technique: a New Method for Transcatheter Closure of Patent Foramen Ovale", Catherization and Cardiovascular Interventions, vol. 53, 2001, pgs. 369-372.

St. Jude Medical, Brktm Transseptal Needle (Instructions for Use), Nov. 2006.

Szili-Torok, T., et al. "Transseptal left heart catherisation guided by intracardiac echocardiography", Heart, vol. 86, vol. 5, Nov. 2001, pgs. 1-5.

Tucker, K., et al., "Transesophageal Echocardiographic Guidance of Transseptal Left Heart Catheterization During Radiofrequency Ablation of Left-Sided Accessory Pathways in Humans", Pace, vol. 19, Mar. 1996, pgs. 272-281.

\* cited by examiner

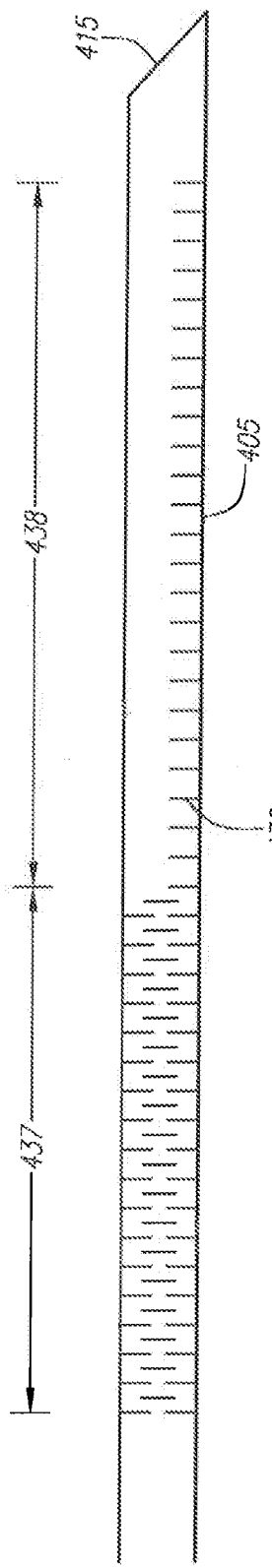
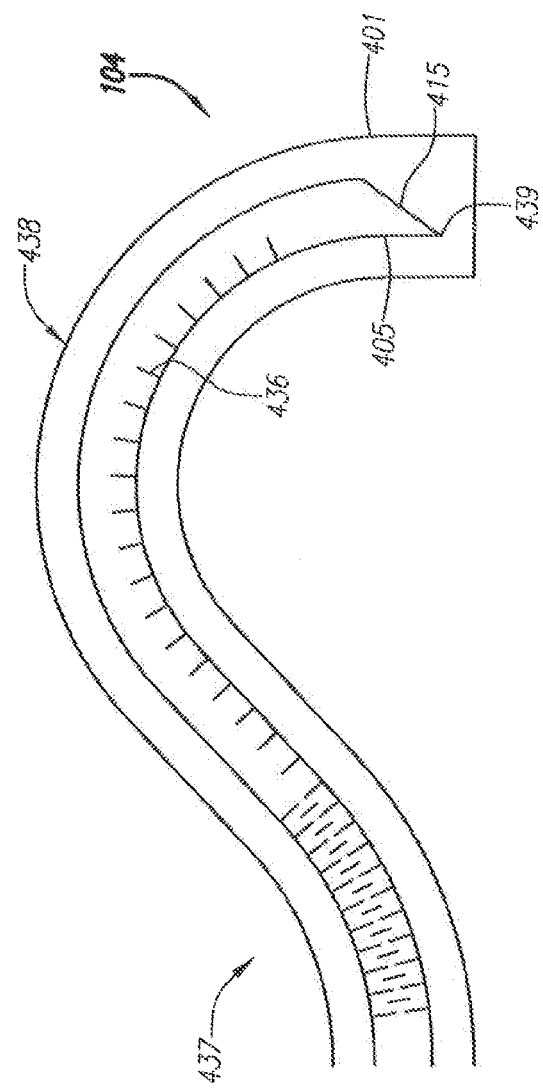
FIG. 18A
FIG. 18B

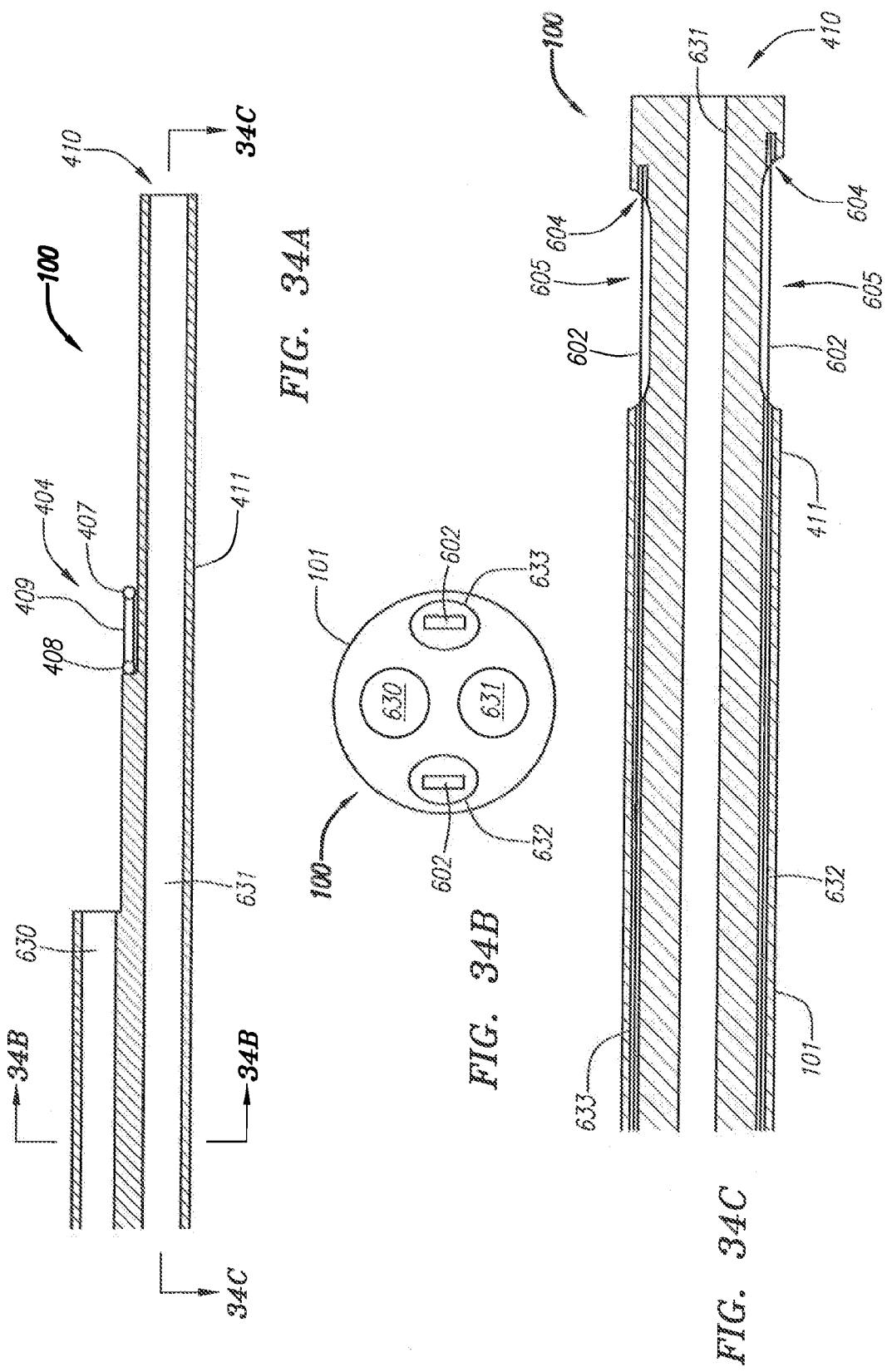

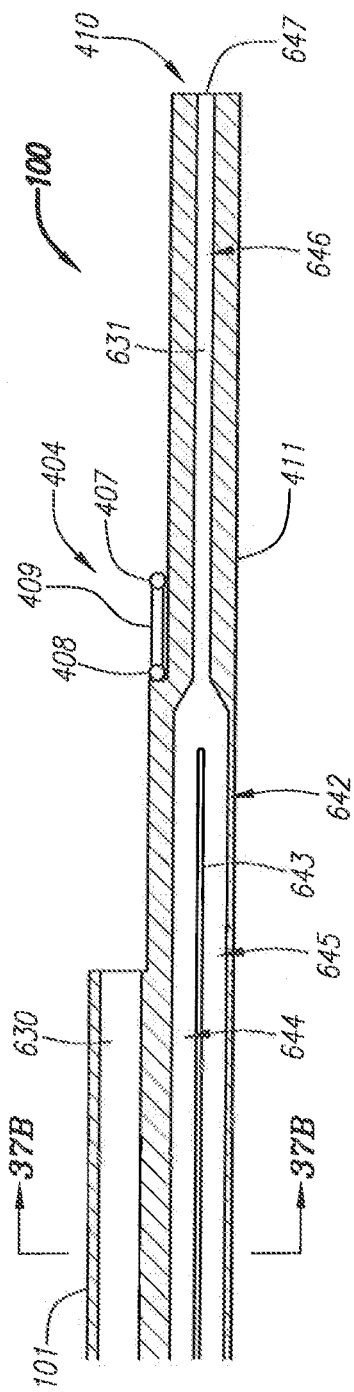
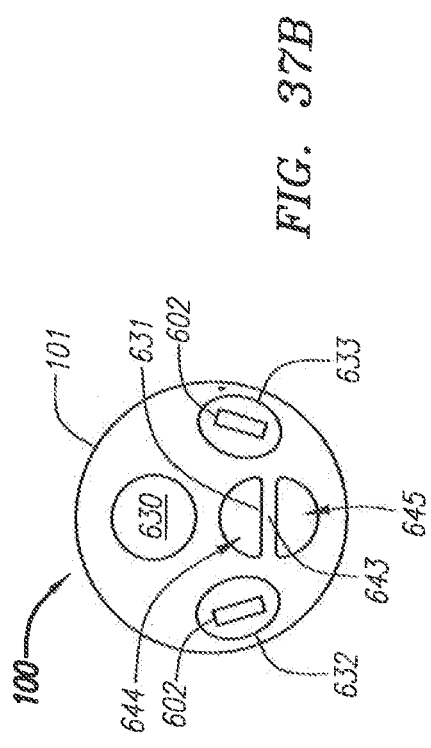
FIG. 37A
FIG. 37B

*FIG. 39B*

```
700 ──➤  From 720
```

722 — Needle member 405 is advanced through septum secundum 210 and septum primum 214 and into left atrium 212

724 — Pusher member 406 is advanced distally to at least partially deploy LA portion 302 of implant 103

726 — Grasping element 506 is moved to the second configuration to free stabilization device 105 from septum primum 214

728 — LA portion 302 is fully deployed of not already

730 — Grasping element 406 is removed to the first configuration

732 — Centering device 106 is moved to the undeployed configuration

734 — Stabilization device 105 is retracted proximally from PFO entrance 217

736 — Needle member 405 is withdrawn into OA delivery member 401 to deploy central portion 303 and at least a portion of RA portion 301 of implant 103

738 — A closure test is performed

740 — OA delivery member 401 is retracted proximally with respect to body member 101

742 — Any tether connection to implant 103 is released

744 — Body member 101 is retracted proximally and withdrawn from the patient

SYSTEMS AND METHODS FOR TREATING SEPTAL DEFECTS

CROSS-REFERENCE TO RELATED APPLICATIONS

This application is a continuation of U.S. patent application Ser. No. 12/725,595, filed Mar. 17, 2010, now abandoned, which is a continuation of U.S. patent application Ser. No. 11/422,871, filed Jun. 7, 2006, now U.S. Pat. No. 7,686,828, which is a divisional of U.S. patent application Ser. No. 11/175,814, filed Jul. 5, 2005, now abandoned, which is a continuation-in-part of U.S. patent application Ser. No. 10/847,747, filed on May 17, 2004, now abandoned which is a continuation-in-part of U.S. patent application Ser. No. 10/734,670, filed Dec. 11, 2003, now U.S. Pat. No. 8,070,826, which is a divisional of U.S. patent application Ser. No. 09/948,453, filed Sep. 7, 2001, now U.S. Pat. No. 6,702,835 and which is a continuation-in-part of U.S. application Ser. No. 09/948,502, filed Sep. 6, 2001, now U.S. Pat. No. 6,776,784, each of which are fully incorporated herein by reference.

FIELD OF THE INVENTION

The present invention relates generally to systems and methods for closing internal tissue defects, and more particularly to systems and methods for closing a patent foramen ovale or other septal defect.

BACKGROUND OF THE INVENTION

By nature of their location, the treatment of internal tissue defects is inherently difficult. Access to a defect through invasive surgery introduces a high level of risk that can result in serious complications for the patient. Access to the defect remotely with a catheter or equivalent device is less risky, but treatment of the defect itself is made more difficult given the limited physical abilities of the catheter. The difficulty in accessing and treating tissue defects is compounded when the defect is found in or near a vital organ. For instance, a patent foramen ovale ("PFO") is a serious septal defect that can occur between the left and right atria of the heart and a patent ductus arteriosus ("PDA") is an abnormal shunt between the aorta and pulmonary artery.

During development of a fetus in utero, oxygen is transferred from maternal blood to fetal blood through complex interactions between the developing fetal vasculature and the mother's placenta. During this process, blood is oxygenated within the fetal lungs. In fact, most of the fetus' circulation is shunted away from the lungs through specialized vessels and foramens that are open during fetal life, but typically will close shortly after birth. Occasionally, however, these foramen fail to close and create hemodynamic problems, which, in extreme cases, can ultimately prove fatal. During fetal life, an opening called the foramen ovale allows blood to pass directly from the right atrium to the left atrium (bypassing the lungs). Thus, blood that is oxygenated via gas exchange with the placenta may travel through the vena cava into the right atrium, through the foramen ovale into the left atrium, and from there into the left ventricle for delivery to the fetal systemic circulation. After birth, with pulmonary circulation established, the increased left atrial blood flow and pressure causes the functional closure of the foramen ovale and, as the heart continues to develop, this closure allows the foramen ovale to grow completely sealed.

In some cases, however, the foramen ovale fails to close entirely. This condition, known as a PFO, can allow blood to continue to shunt between the left and right atria of the heart throughout the adult life of the individual. A PFO can pose serious health risks for the individual, including strokes and migraines. The presence of PFO's have been implicated as a possible contributing factor in the pathogenesis of migraine. Two current hypothesis that link PFO's with migraine include the transit of vasoactive substances or thrombus/emboli from the venous circulation directly into the left atrium without passing through the lungs where they would normally be deactivated or filtered respectively. Other diseases that have been associated with PFO's (and which could benefit from PFO closure) include but are not limited to depression and affective disorders, personality and anxiety disorders, pain, stroke, TIA, dementia, epilepsy, and sleep disorders.

Still other septal defects can occur between the various chambers of the heart, such as atrial septal defects (ASD's), ventricular-septal defects (VSD's), and the like. To treat these defects as well as PFO's, open heart surgery can be performed to ligate and close the defect. Alternatively; catheter-based procedures have been developed that require introducing umbrella or disc-like devices into the heart. These devices include opposing expandable structures connected by a hub or waist. Generally, in an attempt to close the defect, the device is inserted through the natural opening of the defect and the expandable structures are deployed on either side of the septum to secure the tissue surrounding the defect between the umbrella or disc-like structure.

These devices suffer from numerous shortcomings. For instance, these devices typically involve frame structures that often support membranes, either of which may fail during the life of the patient, thereby introducing the risk that the defect may reopen or that portions of the device could be released within the patient's heart. These devices can fail to form a perfect seal of the septal defect, allowing blood to continue to shunt through the defect. Also, the size and expansive nature of these devices makes safe withdrawal from the patient difficult in instances where withdrawal becomes necessary. The presence of these devices within the heart typically requires the patient to use anti-coagulant drugs for prolonged periods of time, thereby introducing additional health risks to the patient. Furthermore, these devices can come into contact with other portions of the heart tissue and cause undesirable side effects such as an arrhythmia, local tissue damage, and perforation.

Accordingly, improved systems and methods for closing internal tissue defects within the heart are needed.

SUMMARY

Improved systems and methods for closing internal tissue defects, such as septal defects and the like, are provided herein by the way of exemplary embodiments. These embodiments are examples only and are not intended to limit the invention.

In one exemplary embodiment, a method of treating a septal defect includes placing a delivery device in proximity with a septal wall having a septal defect, stabilizing the delivery device with an elongate device placed at least partially within the septal defect, and positioning a distal end of the delivery device in a desired orientation with respect to the septal wall, where a first longitudinal axis of the delivery device at the distal end is transverse to a second longitudinal axis of the elongate device.

In another exemplary embodiment, an implantable apparatus for treating a septal defect is provided having a body with a first end portion, a second end portion and a central portion located therebetween. Preferably, the first end portion is configured to engage a first septal surface, the second end portion is configured to engage a second septal surface and the central portion is configured to fit within an opening in a septal wall.

In another exemplary embodiment, a treatment system is provided having a first elongate member and a second elongate delivery member having a distal end rotatably coupled with the first elongate member, wherein the orientation of the distal end is adjustable from a first orientation to a second orientation upon advancement of the elongate member in a distal direction.

In another exemplary embodiment, a treatment system is provided having an elongate tubular member having an inner lumen configured to slidably receive and interact with an inner elongate member. Preferably, the inner elongate member is configured to deploy a grasping device through an aperture in the elongate tubular member upon movement of the elongate inner member with respect to the elongate tubular member.

In yet another exemplary embodiment, a treatment system is provided having a flexible positioning member having a distal end and an elongate support member having an inner lumen configured to slidably receive the flexible positioning member. Preferably, the inner lumen has a distal end configured to abut the distal end of the flexible positioning member and an open portion located proximal to the distal end of the lumen. The flexible positioning member is also preferably configured to extend from the open portion upon advancement of the flexible positioning member distally against the distal end of the inner lumen.

In another exemplary embodiment, a method of treating a septal defect is provided, the method including abutting a limbus of a septum secundum with an abutment of a medical device, creating a hole in the septum secundum with the limbus as a point of reference, and using the hole to facilitate delivery of a device configured to treat a septal defect.

In another exemplary embodiment, a treatment system is provided having an implantable treatment device, a flexible elongate delivery device configured to deliver the implantable treatment device, a stabilization device insertable within an opening in a septum, or tunnel between two septa, and configured to stabilize an elongate body member, and the elongate body member configured for insertion within the vasculature of a patient, the body member configured to slidably receive the delivery device and stabilization device.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention is not limited to require the details of the example embodiments.

BRIEF DESCRIPTION OF THE FIGURES

The details of the invention, both as to its structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

FIG. 18A is a cross-sectional view of an exemplary embodiment of a needle member.

FIGS. 18B-C are cross-sectional views depicting additional exemplary embodiments of a delivery device.

FIG. 34A is a longitudinal cross-sectional view of an exemplary embodiment of a treatment system.

FIG. 34B is a radial cross-sectional view of another exemplary embodiment of a treatment system taken along line 34B-34B of FIG. 34A.

FIG. 34C is a longitudinal cross-sectional view of another exemplary embodiment of a treatment system taken along line 34C-34C of FIG. 34A.

FIG. 37A is a longitudinal cross-sectional view of an exemplary embodiment of a treatment system.

FIG. 37B is a radial cross-sectional view of an exemplary embodiment of a treatment system taken along line 37B-37B of FIG. 37A.

FIGS. 39A-B are flow diagrams depicting an example of a method of treating a septal defect.

DETAILED DESCRIPTION

Described herein are improved devices and methods for treating septal defects. For ease of discussion, the devices and methods will be described with reference to treatment of a PFO. However, it should be understood that the devices and methods can be used in treatment of any type of septal defect including ASD's, VSD's and the like, as well as PDA's or other structural cardiac or vascular defects.

Figure 1:
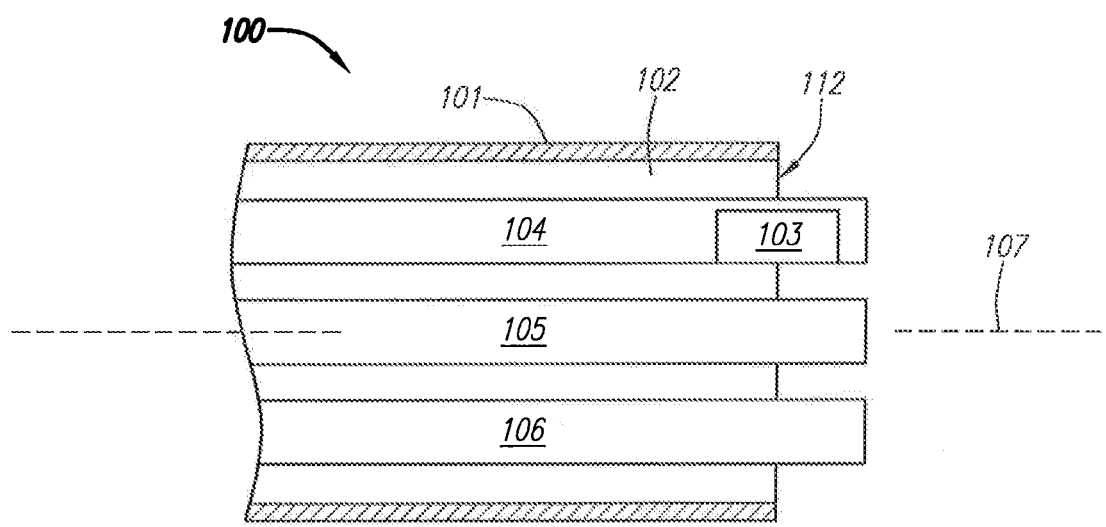
FIG. 1 is a block diagram depicting an exemplary embodiment of a treatment system.

FIG. 1 is a block diagram depicting a distal portion of an exemplary embodiment of a septal defect treatment system 100 configured to treat, and, preferably close, a PFO. In this embodiment, treatment system 100 includes an elongate body member 101 configured for insertion into the vasculature of a patient (human or animal) having a septal defect. Body member 101 has a longitudinal axis 107, distal end 112 and can include one or more lumens 102, each of which can be configured for achieving multiple functions. Preferably, treatment system 100 includes an implantable device 103 (referred to herein as an "implant") configured to at least partially close a septal defect. Treatment system 100 can include a flexible elongate delivery device 104 configured to house and deliver implant 103. To minimize the width of body member 101, implant 103 can be deformable from the configuration desired after implantation to a configuration having a smaller cross-section for storage and housing within delivery device 104 prior to implantation.

Treatment system 100 can also optionally include a stabilization device 105 for stabilization of body member 101 during delivery of implant 103 and a centering device 106 for facilitating the centering or the otherwise desired positioning of implant 103 for delivery. Although shown here as four separate components, any combination of body member 101, delivery device 104, stabilization device 105 and centering device 106 can be integrated together to reduce the number of components to three, two or one total components in treatment system 100.

Figure 2A:
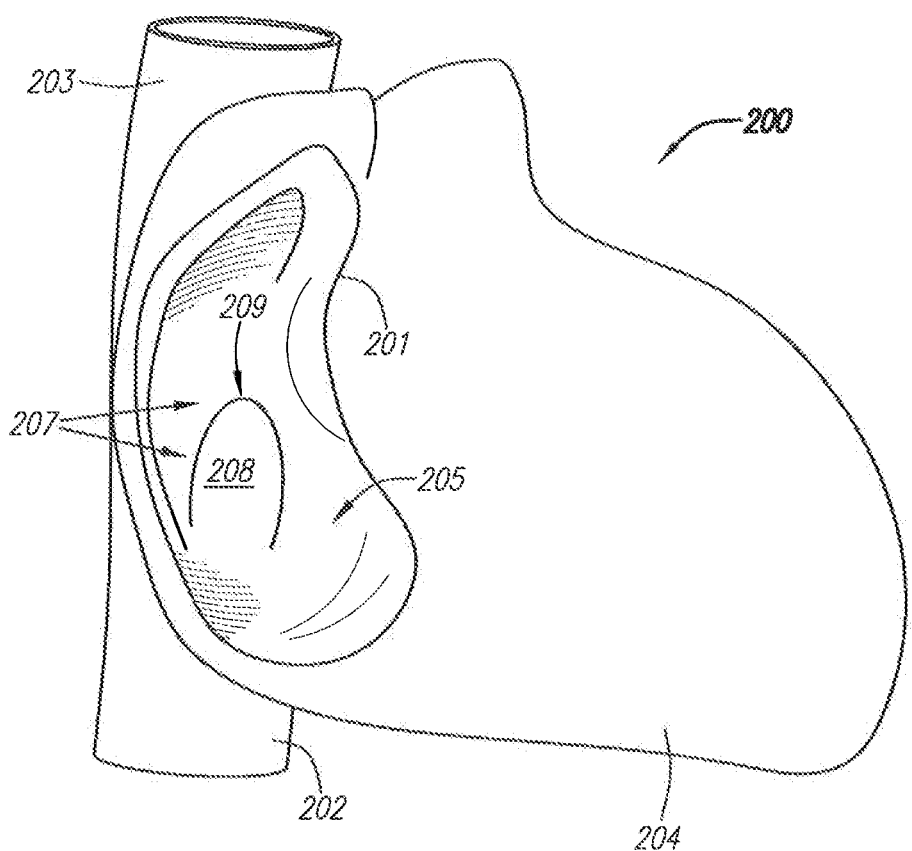
FIG. 2A is an exterior/interior view of the right atrium depicting an example human heart.

To better understand the many alternative embodiments of treatment system 100, the anatomical structure of an example human heart having a PFO will be described in brief. FIG. 2A is an exterior/interior view depicting an example human heart 200 with a portion of the inferior vena cava 202 and the superior vena cava 203 connected thereto. Outer tissue surface 204 of heart 200 is shown along with the interior of right atrium 205 via, cutaway portion 201. Depicted within right atrium 205 is septal wall 207, which is placed between right atrium 205 and the left atrium located on the opposite side (not shown). Also depicted is fossa ovalis 208, which is a region of septal wall 207 where the tissue is relatively thinner than the surrounding tissue, PFO region 209 is located near the upper portion beyond the fossa ovalis 208.

Figure 2B:
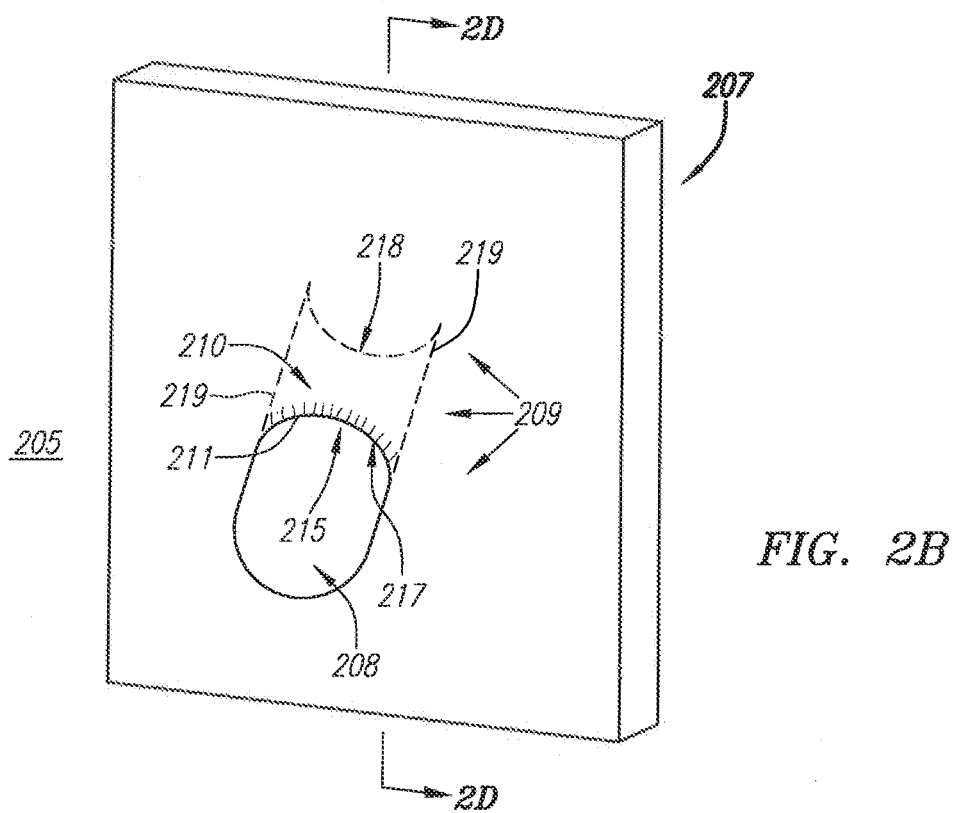
FIGS. 2B-2C are enlarged views of an example atrial septal wall.
Figure 2C:
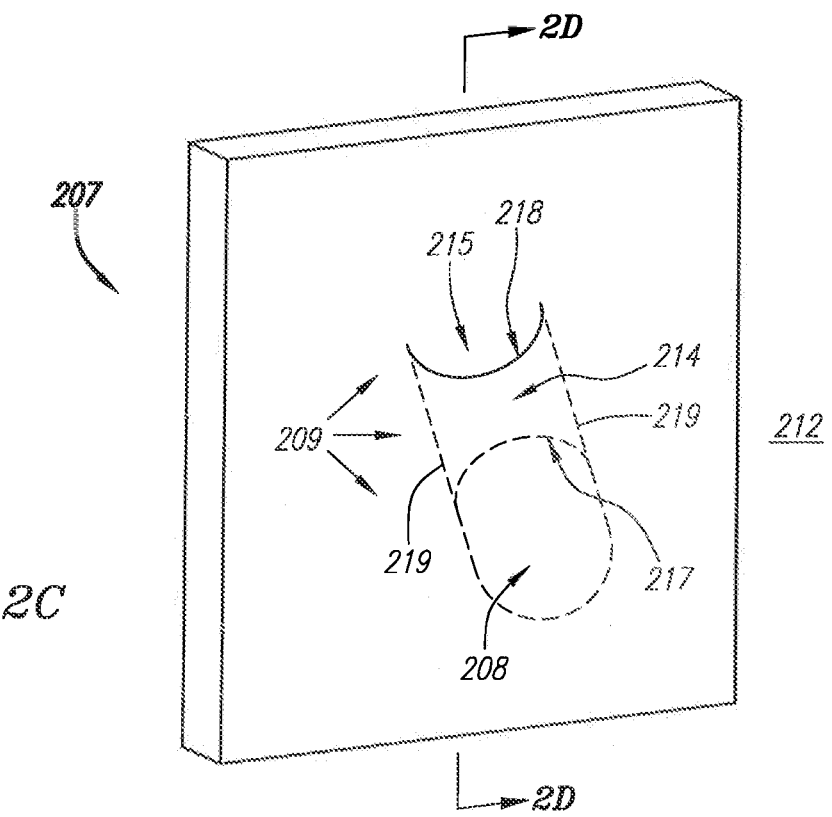

FIG. 2B is an enlarged view of septal wall 207 depicting PFO region 209 in more detail as viewed from right atrium 205. PFO region 209 includes septum secundum 210, which is a first flap-like portion of septal wall 207. The edge of this flap above fossa ovalis 208 is referred to as the limbus 211. FIG. 2C is also an enlarged perspective view of septal wall 207, instead depicting septal wall 207 as viewed from left atrium 212. Here, PFO region 209 is seen to include septum primum 214, which is a second flap-like portion of septal wall 207. Septum primum 214 and septum secundum 210 partially overlap each other and define a tunnel-like opening 215 between sidewalls 219 (indicated as dashed lines in FIGS. 2B-C) that can allow blood to shunt between right atrium 205 and left atrium 212 and is commonly referred to as a PFO.

Figure 2D:
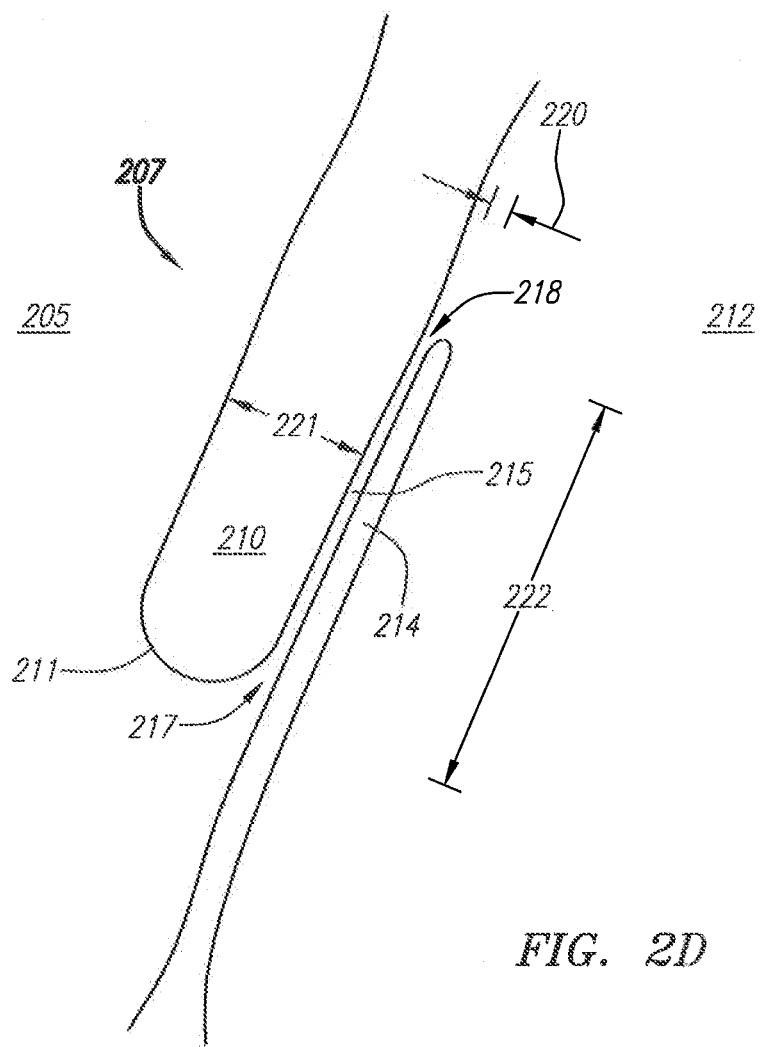
FIG. 2D is a cross-sectional view taken along line 2D-2D of FIGS. 2B-2C depicting another example septal wall.

FIG. 2D is a cross-sectional view depicting an example PFO region 209 taken along line 2D-2D of FIGS. 2B-C. Here, it can be seen that septum secundum 210 is thicker than septum primum 214. Typically, the blood pressure within left atrium 212 is higher than that within right atrium 205 and tunnel 215 remains sealed. However, under some circumstances a valsalva condition can occur where the blood pressure within right atrium 205 becomes higher than the blood pressure within left atrium 212 and blood shunts from right atrium 205 to left atrium 212. Because most typical shunts occur in this manner and for purposes of facilitating the discussion herein, region 217 in FIG. 2D will be referred to as PFO entrance 217, and region 218 will be referred to as PFO exit 218.

Many different variations of PFO's can occur. For instance, thickness 220 of septum primum 214, thickness 221 of septum secundum 210, overlap distance 222 and the flexibility and distensibility of both septum primum 214 and septum secundum 210 can all vary. In FIGS. 2B-C, PFO entrance 217 and PFO exit 218 are depicted as being relatively the same size with the width of tunnel 215, or the distance between sidewalls 219, remaining relatively constant. However, in some cases PFO entrance 217 can be larger than PFO exit 218, resulting in an tunnel 215 that converges as blood passes through. Conversely, PFO entrance 217 can be smaller than PFO exit 218, resulting in an opening that diverges as blood passes through. Furthermore, multiple PFO exits 218 can be present, with one or more individual tunnels 215 therebetween. Also, in FIGS. 2B-D, both septum primum 214 and septum secundum 210 are depicted as relatively planar tissue flaps, but in some cases one or both of septum primum 214 and septum secundum 210 can have folded, non-planar, highly irregular shapes.

As will be described in more detail below, treatment of a PFO preferably includes inserting treatment system 100 into the vasculature of a patient and advancing body member 101 through the vasculature to inferior vena cava 202, from which access to right atrium 205 can be obtained. Once properly positioned within right atrium 205, delivery device 104 can be used to deliver implant 103 to PFO region 209, preferably by inserting implant 103 through septum secundum 210 and primum 214 such that implant 103 lies transverse to tunnel 215 and can at least partially close tunnel 215.

Figure 3:
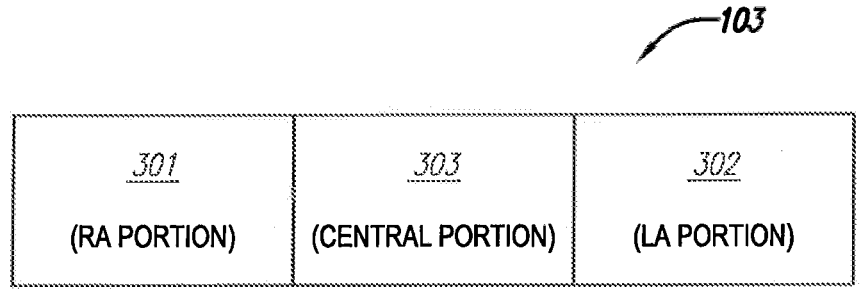
FIG. 3 is a block diagram depicting an exemplary embodiment of an implantable treatment device.

FIG. 3 is a block diagram depicting one exemplary embodiment of implant 103. Implant 103 can be configured in an almost limitless number of different ways, as this block diagram shows. Here, implant 103 includes a first end portion 301, a second end portion 302 and a central portion 303 preferably coupled therebetween. First and second end portions 301-302 are each preferably configured to engage opposing surfaces of septal wall 207. First end portion 301 can be configured to engage the surface of septal wall 207 on the right atrium (RA) side, while second end portion can be configured to engage the surface of septal wall 207 on the left atrium (LA) side. Although end portions 301-302 can be placed anywhere within heart 200 as desired, in order to facilitate the description of implant 103 herein, first end portion 301 will be referred to as RA portion 301 and second end portion will be referred to as LA portion 302.

Central portion 303 is preferably configured to fit within a manmade or surgically created opening in either septum primum 214, septum secundum 210 or both. Central portion 303 is also preferably configured to apply a force adequate to bring end portions 301-302 towards one another when implanted, to be implantable into septal walls 207 of varying thickness and to fit within elongate body member 101, the diameter of which is preferably minimized for ease of insertion within the patient's vasculature.

Implant 103 can be configured in any manner desired to fit the needs of the application. Implant 103 can have any size and shape and can include additional portions not shown in FIG. 3 to achieve a different set of functions. Implant 103 can also be fabricated in any desired manner and from any materials suitable fir implantation within the patient including, but not limited to, elastic materials, superelastic materials, shape-memory materials, composite materials, polymeric materials, coatings, drug containing materials, blends with radio-opaque materials and biodegradable materials.

Figure 4A:
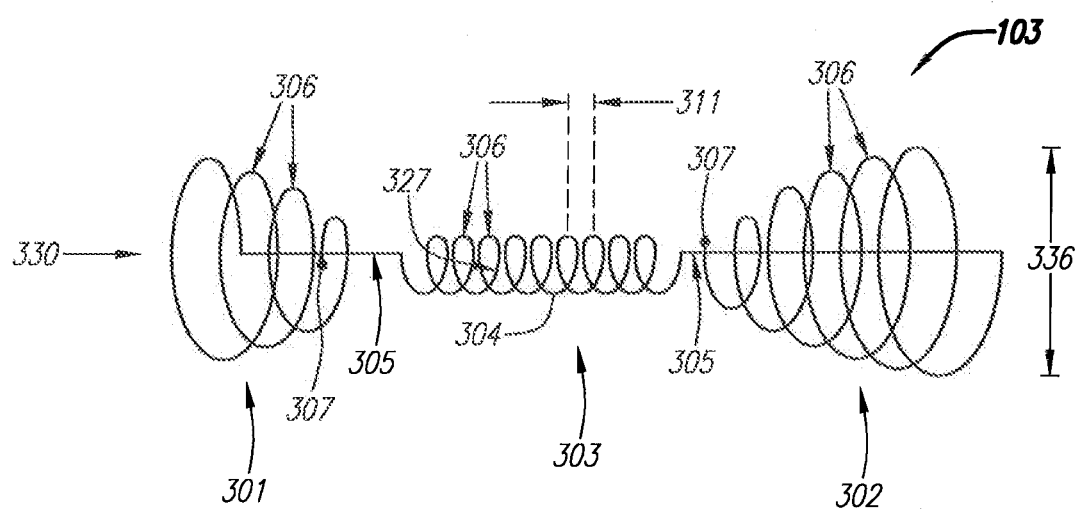
FIG. 4A is a perspective view depicting another exemplary embodiment of an implantable treatment device.
Figure 4B:
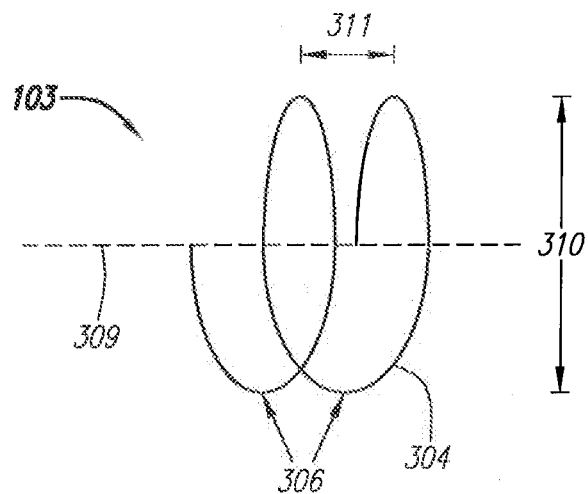
FIG. 4B is a perspective view depicting an exemplary embodiment of several coiled segments of an implantable treatment device.

FIG. 4A is a perspective view depicting another exemplary embodiment of implant 103 shown in an "at rest" configuration. In this embodiment, implant 103 is configured in a coil-shaped manner with a wire-like body 304 composed of an elastic material. Wire-like body 304 can have any wire-like cross-sectional shape including, but not limited to circular, elliptical, oval, rounded, arcuate, polygonal and any combination thereof. Each portion 301-303 can be composed of one or more coiled segments 306, with a coiled segment 306 being defined herein as a segment that is curved or otherwise shaped in any manner about one or more axes. Thus, rounded, straight, irregular and polygonal segments are all considered to be coiled. A coiled segment 306 can be curved or otherwise shaped less than 360 degrees about the one or more axes. FIG. 4B is a perspective view depicting an exemplary embodiment of several coiled segments 306, which could be used in any of portions 301-303. In this embodiment, each coiled segment 306 is coiled with a constant rate of curvature about the same axis 309. Coiled segments 306 have approximately the same width 310 and are stacked and separated by a distance 311, which will be referred to herein as stacking distance 311.

Referring back to FIG. 4A, implant 103 has an overall width 336. Central portion 303 includes a plurality of coiled segments 306 having substantially the same width 310. Each end portion 301-302 includes a plurality of coiled segments having varied widths or diameters 310. In this case, the width 310 of the outermost coiled segment 306 is the greatest and the widths 310 of each successive coiled segment 306 decreases as one approaches the innermost coiled segment 306. Each end portion 301-302 is coupled with central portion 303 via optional generally straight sections 305. Generally straight sections 305 can prevent blood from shunting between the right and left atria through open interior region 327 of coiled central portion 303, by allowing the adjacent tissue to encroach upon and surround straight section 305. Plugs of bioabsorbable or hydrophilic material may also be provided to minimize such shunting. Generally straight sections 305 can also prevent tissue from getting caught, or hung up, between central portion 303 and RA/LA portions 301/302. Each generally straight sections 305 is not required to be straight and, in fact, can have any non-coiled shape. Central portion 303 can be placed approximately equidistant from end portions 301-302, as depicted here, or central portion 303 can be placed closer to one of end portions 301-302 than the other. Generally straight sections 305 are optional and can be included on only one side of central portion 303 or omitted altogether, in which case the coiled segments 306 of central portion 303 extend directly up to a coiled segment 306 of each end portion 301-302.

The end tips 307 of body 304 are preferably atraumatic so as to minimize injury to cardiac tissue. In this embodiment, end tips 307 are rounded and have a larger diameter than body 304. End tips 307 can also be configured as floppy tips that are curled or coiled and can be flexible or non-flexible. Also, it should be noted that any part of implant 103 can be modified for imaging purposes. For instance, in this embodiment end tips 307 are radio-opaque to increase visibility of implant 103 during imaging. Also, end tips 307 can be configured to facilitate delivery. For instance, in one embodiment end tips 307 can be shaped to minimize the risk of becoming caught on any portion of the delivery device 104. In another embodiment, end tips 307 are configured to interface with the delivery device 104 to allow manipulation of implant 103 before, during or after delivery.

Figure 4C:
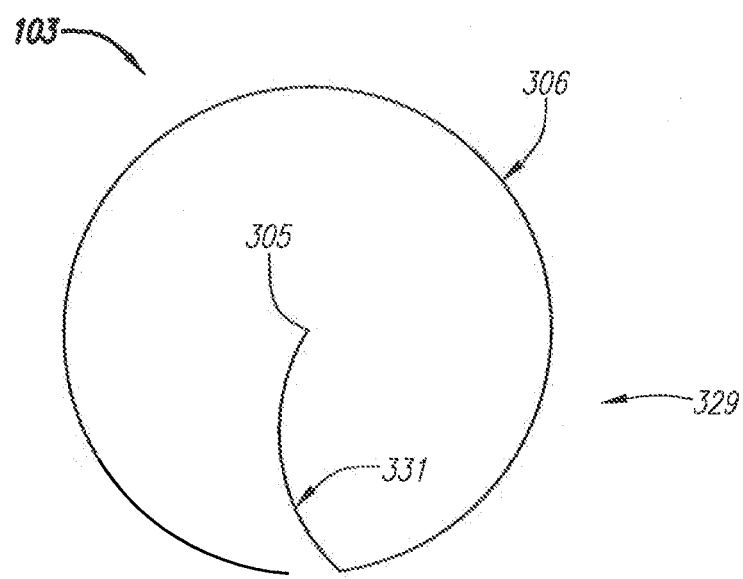
FIG. 4C depicts a side view of the embodiment of the implantable treatment device taken along direction 330 of FIG. 4A.
Figure 4D:
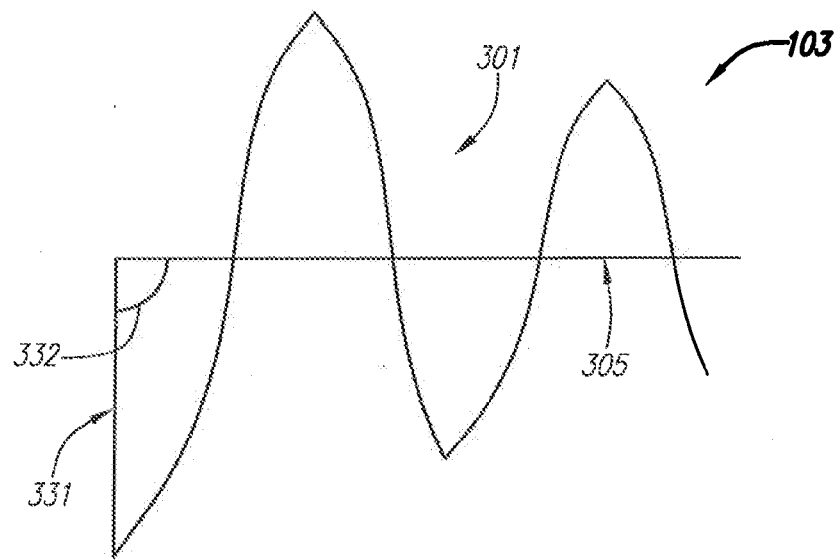
FIG. 4D is a schematic view depicting another exemplary embodiment of the implantable treatment device as viewed from direction 329 of FIG. 4C.

FIG. 4C depicts a side view of the embodiment of implant 303 taken along direction 330 of FIG. 4A. For ease of illustration, FIG. 4C depicts only the outermost coiled segment 306 of RA portion 301, transition section 331 and the generally straight section 305 located between RA portion 301 and central portion 303. Transition section 331 is an optional section of implant 103 that can be straight, curved or any other shape. FIG. 4D depicts RA portion 301, transition section 331 and the generally straight section 305 located between RA portion 301 and central portion 303 as viewed from direction 329 of FIG. 4C. Here, it can be seen that transition section 331 connects to generally straight section 305 at 90 degree angle 332. Angle 332 can be varied as desired, but values of angle 332 approaching 0 degrees or 180 degrees are less preferable due to the increased risk of RA portion 301 (or LA portion 302) being drawn into manmade opening 315, which is described in more detail below.

Figure 4E:
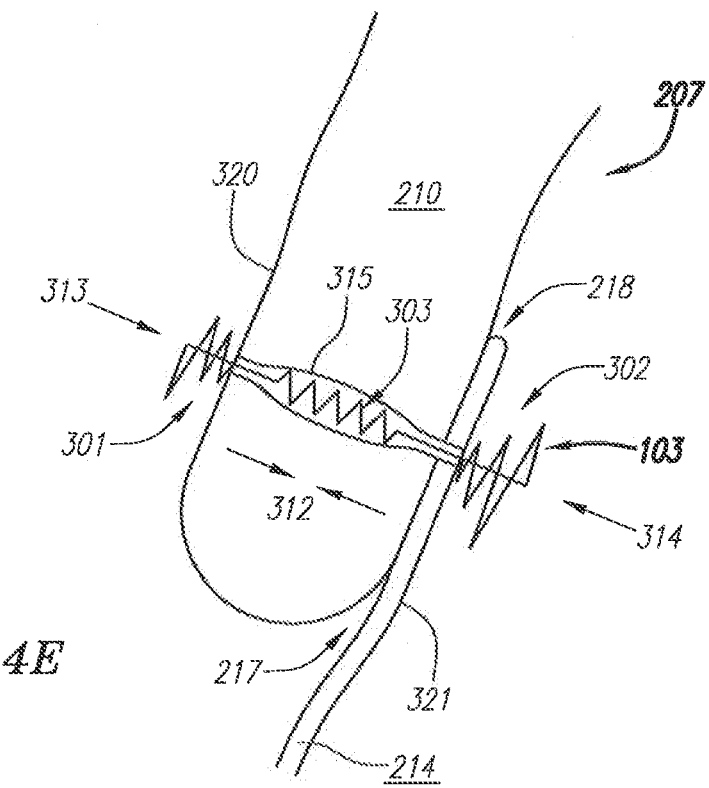
FIG. 4E is cross-sectional view depicting the exemplary embodiment of the implantable treatment device depicted in FIG. 4A implanted within an example heart.

FIG. 4E is cross-sectional view depicting the exemplary embodiment of implant 103 depicted in FIG. 4A implanted within heart 200 using one exemplary method of implantation. Here, an opening 315 has been surgically created in septum primum 214 and septum secundum 210 and implant 103 has been positioned such that central portion 303 resides within the opening 315. RA portion 301 and LA portion 302 are positioned on opposite sides of septal wall 207 to engage surface 320 of septum secundum 210 and surface 321 of septum primum 214, respectively. Central portion 303 preferably exerts a contractile force 312 to bring portions 301-302 towards one another, which in turn preferably draws septum primum 214 and septum secundum 210 together to at least partially close PFO tunnel 215. Typically, portions 301 and 302 will lie flat against the septa, but are illustrated as compressed conical coils for purposes of clarity. As mentioned above, the widths 310 of coiled segments 306 of RA and LA portions 301-302 get progressively larger from the innermost to the outermost segment 306. If the rate of change of width 310 is large enough to allow coiled segments 306 to pass through each other, then portions 301 and 302 can exert additional closure forces 313 and 314, respectively, which oppose each other and assist central portion 303 in closing PFO tunnel 215.

LA portion 302 and RA portion 301 can each be sized in any manner desired. Preferably, LA portion 302 is configured to have relatively larger coiled segment widths 310, include relatively more coiled segments 306 and exert a closure force over a relatively larger area 314 than RA portion 301. This can be for one of at least two reasons. As will be described in more detail below, preferably, LA portion 302 is deployed in PFO region 209 first and, once in contact with septal wall 207, LA portion 302 is used to help deploy, or pull, portions 303 and 301 from delivery device 104. Also, septum primum 214 is typically thinner than septum secundum 210 and more likely to tear or deform to the extent that LA portion 302 can be pulled though septum primum 214.

Preferably, implant 103 is configured to adjust to septal walls 207 having varying degrees of thickness. Accordingly, central portion 303 preferably has a compressibility sufficient to apply a closure force 312 to thinner septal walls 207 while at the same time having an expandability sufficient to accommodate thicker septal walls 207 without excessive permanent deformation. In one exemplary embodiment, which is for purposes of illustration only and should not be used to limit the scope of the invention in any way, central portion 303 is expandable from 3 to 8 millimeters (mm) without excessive permanent deformation.

Figure 4F:
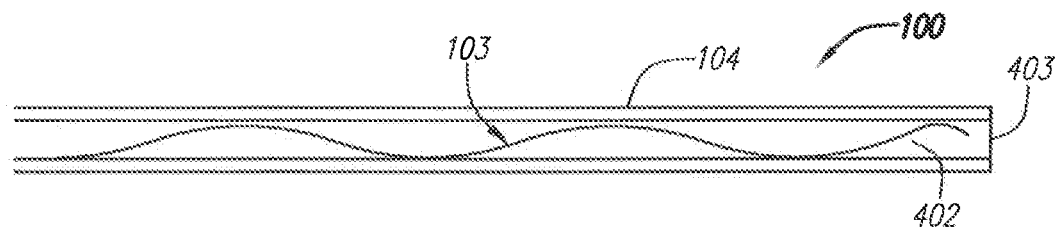
FIGS. 4F-G are cross-sectional views of additional exemplary embodiments of the treatment system with a delivery device.

As mentioned above, implant 103 can be deformable between a configuration suited for housing within delivery device 104 and the implanted configuration depicted in FIG. 4E. FIG. 4F is a cross-sectional view of an exemplary embodiment of treatment system 100 depicting delivery device 104 having an inner lumen 402 with implant 103 housed therein. Implant 103 is preferably housed within lumen 402 until body member 101 is advanced within the patient into the desired position within heart 200 for implantation, at which time implant 103 is delivered to PFO region 209 through open distal end 403. Here, implant 103 is deformed from the at rest, i.e., unbiased, configuration depicted in FIG. 4A into a generally straight configuration where coiled portions 301-303 are mostly unwound into a relatively straight state. This housed configuration significantly reduces the overall anchor width 336 of implant 103 and allows the size of delivery device 104 and, in turn, body member 101 to be minimized.

Figure 4G:
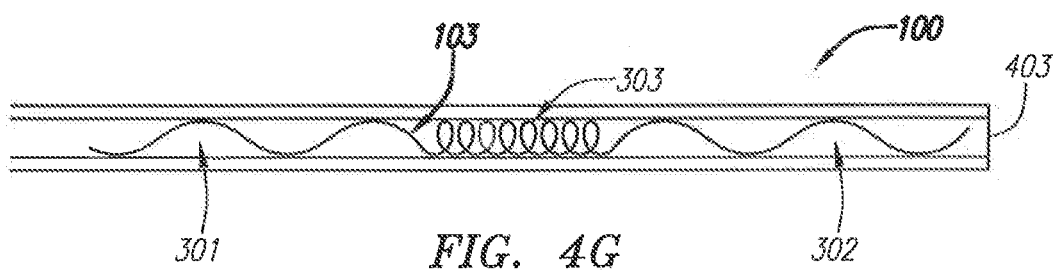

FIG. 4G is a cross-sectional view of another exemplary embodiment of treatment system 100 depicting delivery device 104 with implant 103 in the housed configuration. Here, central portion 303 of implant 103 remains coiled in a state similar to the resting state of FIG. 4A, while RA/LA portions 301/302 are partially unwound into a relatively straight state from the coiled rest state. Preferably, coiled segments 306 of central portion 303 generally have smaller widths 310 than most of the coiled segments 306 of RA/LA portions 301/302. Coiled segments 306 having a smaller width, i.e., more tightly wound coils, can be permanently deformed more easily when unwound and, therefore, by maintaining central portion 303 in the coiled state, the risk of permanent deformation to central portion 303 is reduced. Implant 103 can be deformed in any manner when housed within delivery device 104. For coil-like embodiments of implant 103, this can include deforming any or all of coiled segments 306, to any degree, in any portion 301-303.

To facilitate the deformation of implant 103 between the housed configuration and the implanted configuration depicted in FIG. 4E, implant 103 is preferably composed of an elastic material. Preferably, body 304 is composed of a titanium-nickel alloy such as NITINOL, although any elastic material can be used, including polymers, rubber-like materials, stainless steel, other metal alloys and the like. As one of skill in the art will recognize, the amount of closure force 312-314, the degree of allowable deformation and the like will depend, in part, on the type of material used to form body 304.

Figure 5A:
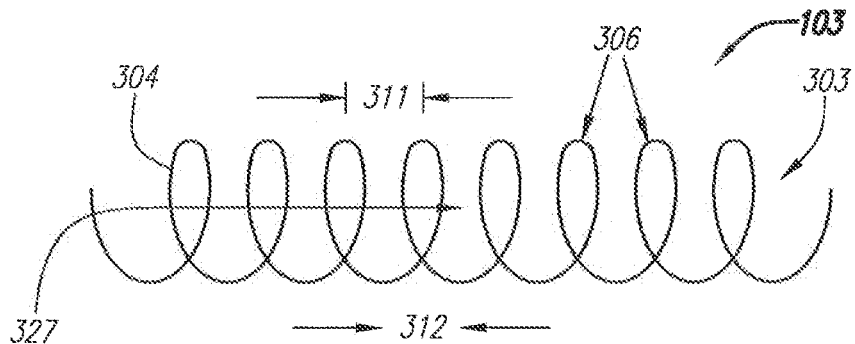
FIGS. 5A-E are perspective views depicting additional exemplary embodiments of the central portion the implantable treatment device.
Figure 5B:
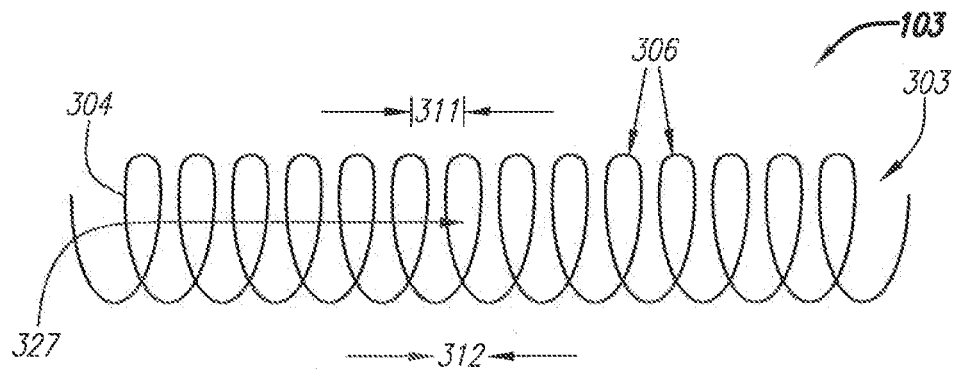

FIGS. 5A-E are perspective views depicting additional exemplary embodiments of central portion 303 of implant 103. Each of these embodiments can be used with any RA portion 301 and LA portion 302. In FIG. 5A, central portion 303 includes a plurality of coiled segments 306 where the stacking distance 311 between each segment 306 is relatively greater than the embodiment of central portion 303 depicted in FIG. 5B. Generally, a smaller stacking distance 311 will provide a greater closure force 312, if all other implant parameters remain the same. Any stacking distance 311 can be used in central portion 303 as desired, including configurations where there is no gap between each coiled segment 306, i.e., each coiled segment 306 lies flush with any adjacent coiled segment 306. Use of a larger stacking distance 311 that provides for gaps between adjacent coiled segments 306 allows the adjacent septal tissue to grow into the open interior region 327 of the coiled central portion 303, which can provide positional stability to the device and reduce any risk of blood shunting through open region 327.

Figure 5C:
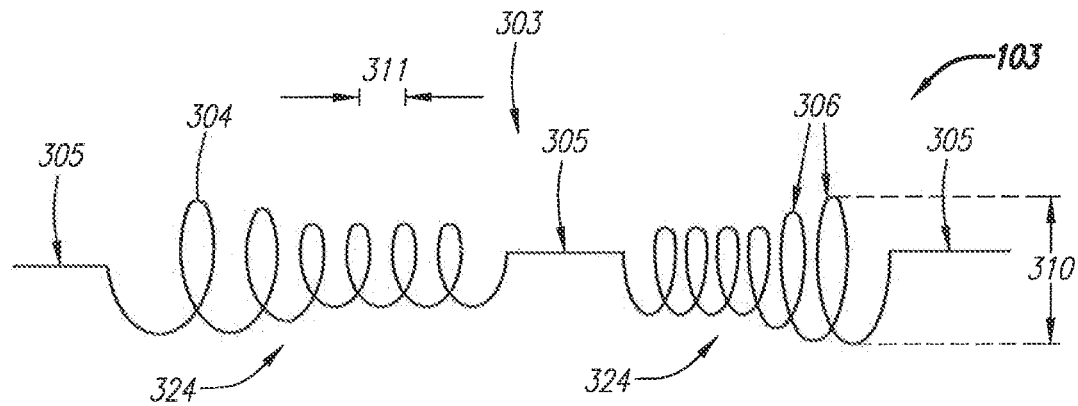

In FIG. 5C, central portion 303 includes a combination of coiled sections 324 and generally straight sections 305. It should be noted that central portion 303 can include any number of one or more coiled sections 324 in any combination with any number of one or more generally straight sections 305. As can be seen here, each coiled section 324 can be configured differently from any other coiled section 324, i.e., each coiled portion can include a different number of coiled segments 306, with different stacking distances 311 and different widths 310, etc.

Figure 5D:
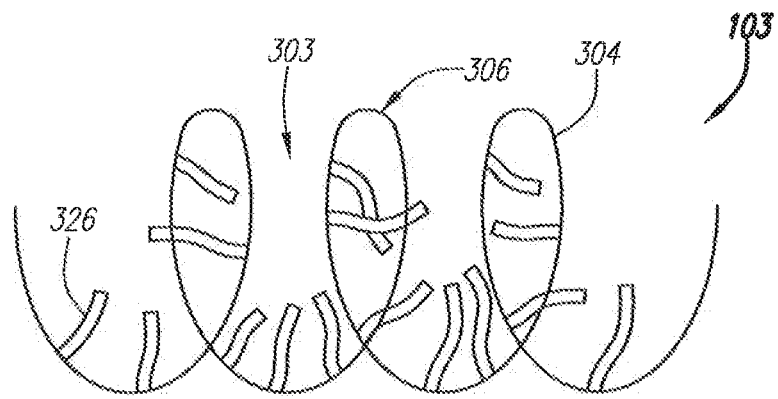

FIG. 5D depicts another exemplary embodiment where blocking material 326 has been coupled with coil body 304. Blocking material 326 preferably reduces any risk of blood shunting through the interior of coiled segments 306, either by blocking blood flow directly or by facilitating the formation of blood clots within open interior region 327. In one exemplary embodiment, blocking material 326 can include multiple DACRON fibers adhesively or mechanically coupled to the outer surface of body 304. In another exemplary embodiment, a polymer or metal plug is placed in open interior region 327 to prevent blood flow. As one of skill in the art will readily recognize, any type of plug, device, material or coating can be used and attached to body 304 in any manner, the numerous combinations of which will not be listed here.

Figure 5E:
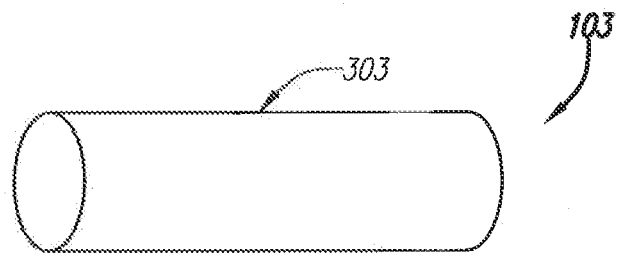

Central portion 303 is not required to include a coiled section 324 and can, in fact, be only a generally straight section 305. Furthermore, central portion 304 is not required to be formed from a wire-like body 304 and can be configured in any manner desired as depicted in the block diagram of FIG. 3. For instance, central portion 303 can be formed from an elastomeric or rubber-like stretchable member, as depicted in FIG. 5E.

Referring in more detail to RA portion 301 and LA portion 302, FIGS. 6A-I are perspective views depicting multiple embodiments exemplary of either RA portion 301 or LA portion 302. Any of the RA/LA portions 301/302 depicted here can be used with any embodiment of central portion 303 described with respect to FIGS. 5A-E. For instance, an exemplary embodiment of implant 103 can have RA portion 301 configured in a manner similar to that described with respect to FIG. 6A, central portion 303 configured in a manner similar to that described with respect to FIG. 5A, and LA portion 302 configured in a manner similar to that described with respect to FIG. 6B.

Figure 6A:
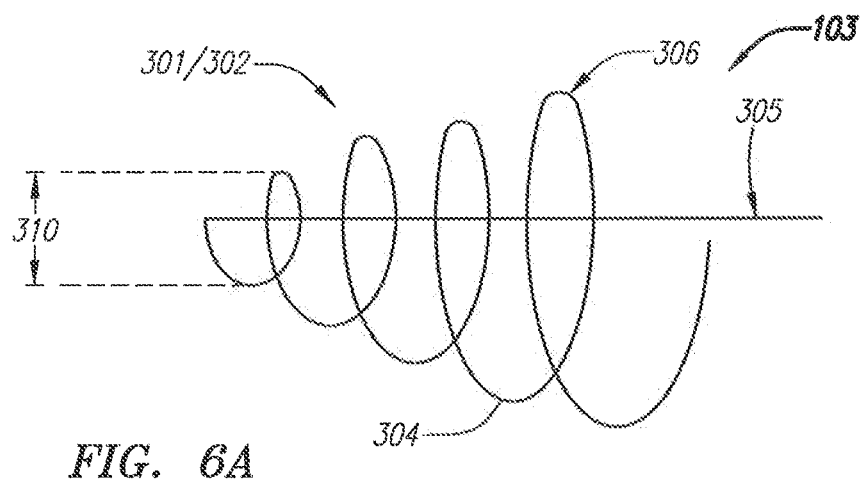
FIGS. 6A-I are perspective views depicting additional exemplary embodiments of either the first and/or the second end portions of the implantable treatment device.

In FIG. 4A, RA/LA portions 301/302 include multiple stacked coiled segments 306 having gradually decreasing widths 310 from the outermost to the innermost segment 306 (outermost being used to reference the segments 306 on the far left and right of FIG. 4A). In FIG. 6A, RA/LA portions 301/302 include multiple coiled segments 306 having gradually increasing widths 310 from the outermost to the innermost segment 306. The embodiment of portions 301-302 described with respect to FIG. 4A can be less susceptible to entering opening 315, due to the presence of a relatively larger coiled segment 306 coupled with transition region 305.

Figure 6B:
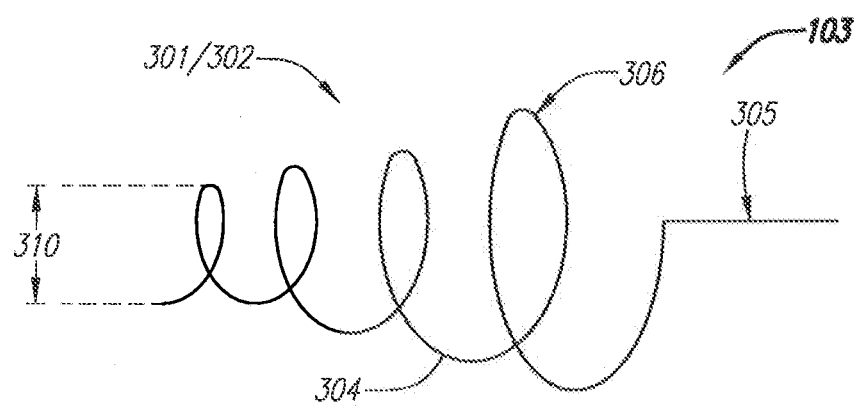
Figure 6C:
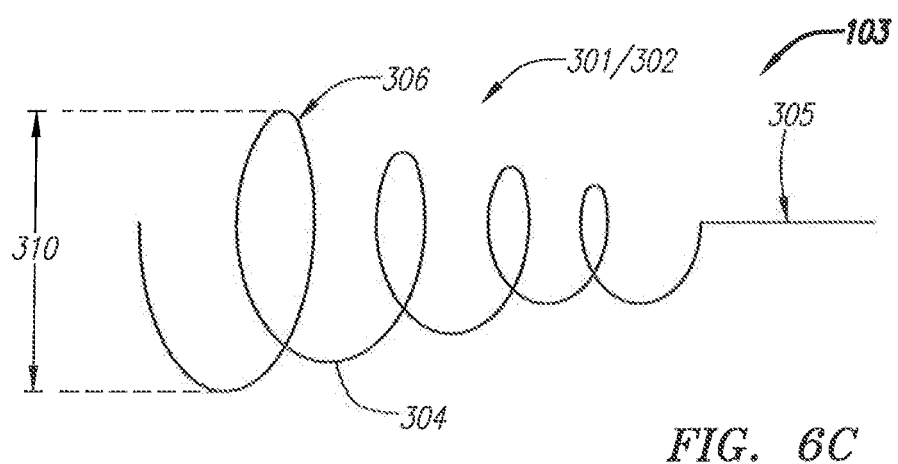

In both FIGS. 4A and 6A, coded segments 306 of RA/LA portions 301/302 are stacked in an inwards manner, i.e., the outermost segment 306 is coupled with central portion 303 or generally straight section 305, if present (as shown here) and RA/LA portion 301/302 overlaps central portion 303. In FIGS. 6B-C, RA/LA portions 301/302 include multiple coiled segments 306 stacked in an outwards manner, i.e., the innermost segment 306 is coupled with central portion 303 or generally straight section 305, if present (as shown here). Generally, stacking segments 306 in an inwards manner will provide greater closure forces than stacking in an outwards manner. In FIG. 6B, RA/LA portions 301/302 include multiple coiled segments 306 having gradually increasing widths 310 from the outermost to the innermost segment 306, while in FIG. 6C, RA/LA portions 301/302 include multiple coiled segments 306 having gradually decreasing widths 310 from the outermost to the innermost segment 306.

Figures 6D, 6E, 6F:
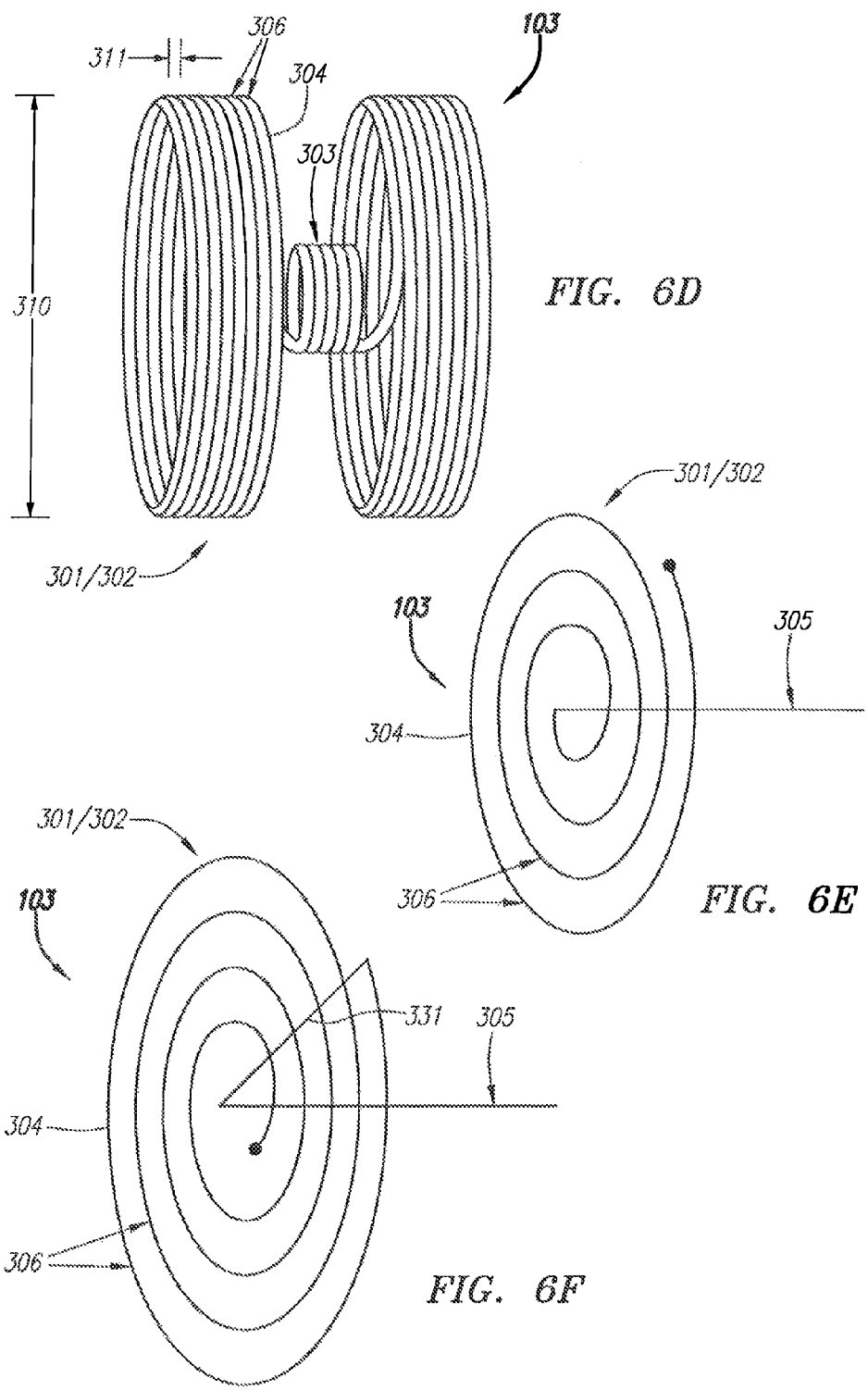

In FIG. 6D, RA/LA portions 301/302 are tightly stacked with a constant width 310 such that no gap exists between adjacent coiled segments 306. This embodiment of RA/LA portions 301/302 exhibits a high resistance to the potential for being pulled into opening 315.

RA/LA portions 301/302 are not required to be implemented in a stacked configuration. For instance, in FIGS. 6E-F, RA/LA portions 301/302 each include multiple coiled segments 306 having varying widths 310 arranged in a generally co-planar fashion, i.e., for all segments 306 the stacking distance 311 is close to or equal to zero. In FIG. 6E, the smallest coiled segment 306 is coupled with generally straight section 305, while in FIG. 6F, the largest coded segment 306 is coupled with generally straight section 305. To lessen the risk of RA/LA portions 301/302 being pulled into opening 315 in the embodiment depicted in FIG. 6F, transition section 331 is preferably positioned on the outside of coiled segments 306 such that, when implanted, coiled segments 306 are located between transition section 331 and septal wall 207.

Figure 6G:
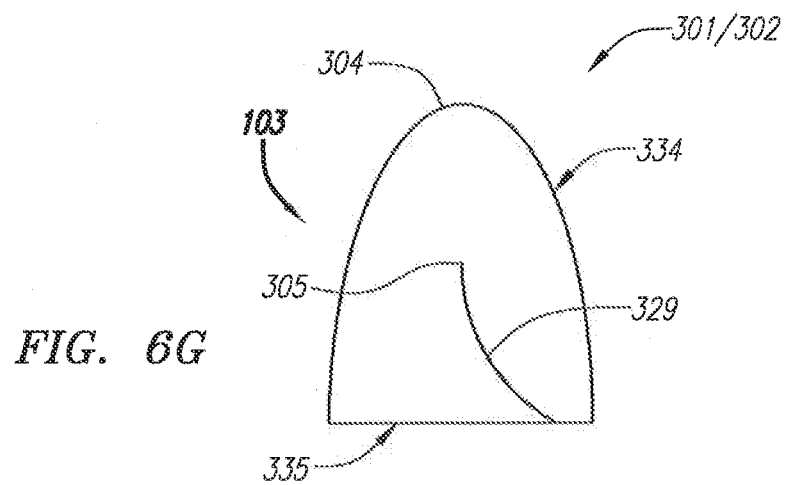
Figure 6H:
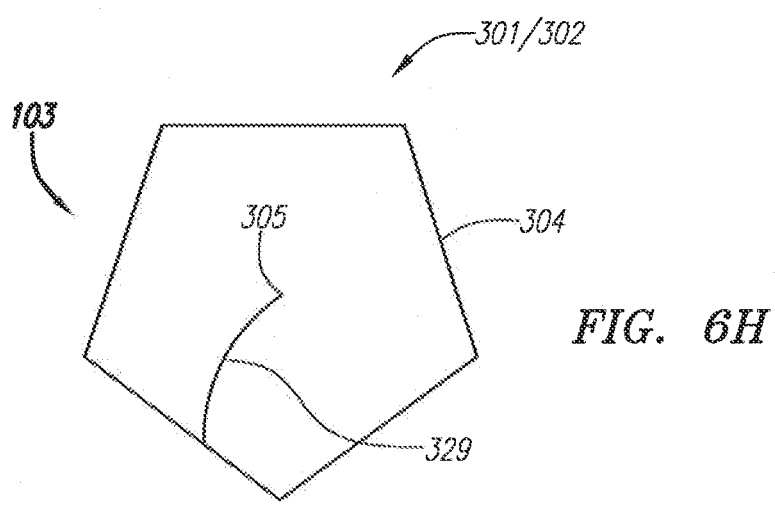
Figure 6I:
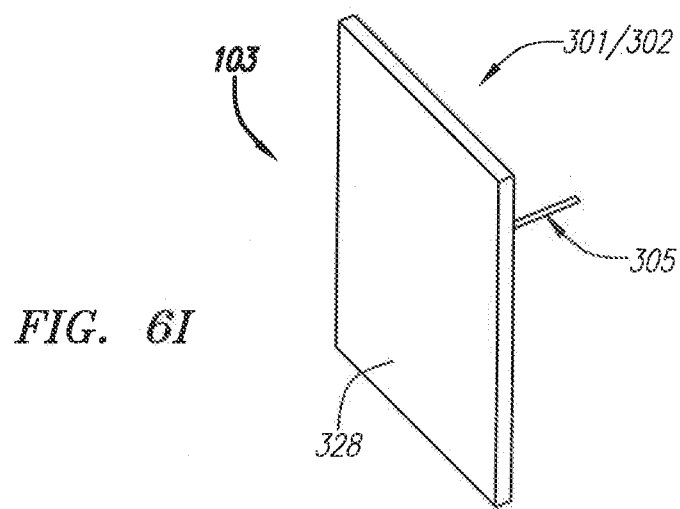

In the embodiments discussed above, the radius of curvature of the coiled segments 306, present in either RA/LA portions 301/302 or central portion 303, is generally constant or varies at a constant rate, resulting in a circular, spiral or helical appearance when viewed from the side (e.g., direction 330 of FIG. 4A). It should be understood that the radius of curvature can vary at any rate, abruptly or gradual, allowing coiled segments 306 to take any shape or form desired, whether in RA/LA portions 301/302 or central portion 303. For instance, FIGS. 6G-H are schematic views depicting additional exemplary embodiments of RA/LA portions 301/302 as viewed from the side. FIG. 6G depicts RA/LA portion 301/302 having an elliptical D shape. Here, RA/LA portion 301/302 has an elliptical portion 334 and a generally straight portion 335, which can be placed adjacent to fossa ovalis 208 to lessen the extent to which RA/LA portion 301/302 overlaps fossa ovalis 208 and minimize the risk of piercing or rupturing fossa ovalis 208. FIG. 6G depicts another exemplary embodiment of RA/LA portion 301/302 having a generally pentagonal shape.

RA/LA portions 301/302 are not required to include coiled segments 306 and are not required to be formed from a wire-like body 304. As mentioned above, RA/LA portions 301/302 can be configured in any manner desired as depicted in the block diagram of FIG. 3. For instance, RA/LA portions 301/302 can be formed from an elastomerie or rubber-like membrane 328 in an umbrella-like fashion, or a sheet-like fashion as depicted in the exemplary embodiment of FIG. 6I.

Figure 7A:
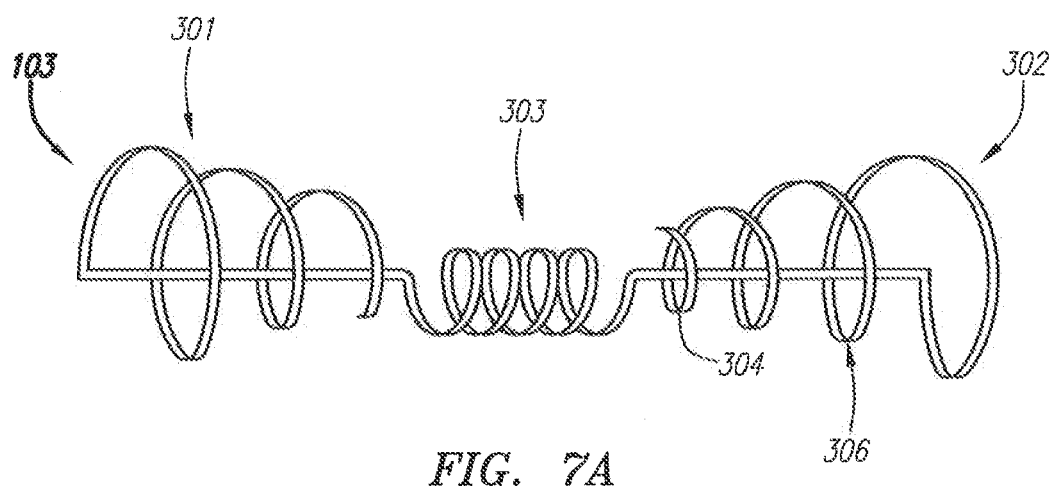
FIG. 7A-C, 8 and 9A-C are perspective views depicting additional exemplary embodiments of the implantable treatment device.
Figure 7B:
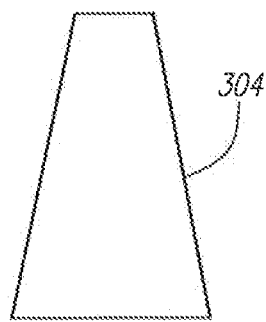
Figure 7C:
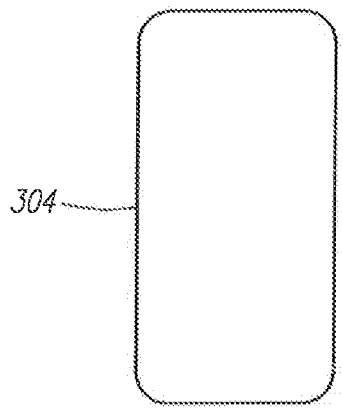

FIG. 7A-C are perspective views depicting additional exemplary embodiments of implant 103 having a ribbon-like body 304. Ribbon-like bodies 304 can have a generally polygonal cross-section and can be differentiated from the wire-like bodies 304 depicted in FIGS. 4A-5E, which can have generally circular, rounded etc. cross-sections as described above. FIG. 7A is an embodiment of implant 103 having a ribbon-like body 304 configured similar to that of the embodiment depicted in FIG. 4A. Generally, any of the embodiments described with respect to wire-like bodies 304 can also be implemented with ribbon-like bodies 304. Ribbon-like bodies 304 can have any ribbon-like cross-sectional shape desired. FIGS. 7B-C are cross-sectional views depicting ribbon-like body 304 having generally polygonal shapes. FIG. 7B is a cross-sectional view depicting ribbon-like body 304 having a generally tapered trapezoidal shape. FIG. 7C is a cross-sectional view depicting ribbon-like body 304 having a generally rectangular shape with rounded corners.

Figure 8:
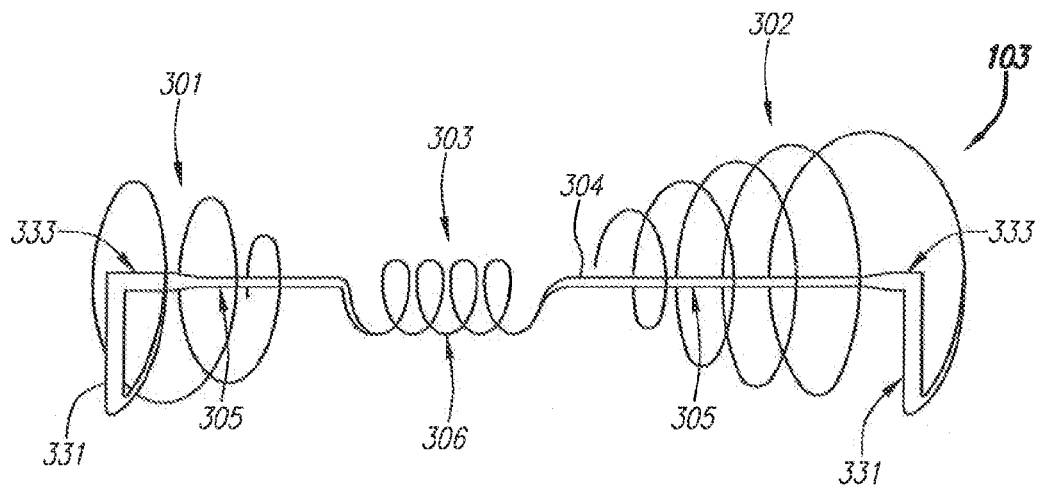

In addition to other parameters, the thickness of implant body 304 can vary as desired. For instance. FIG. 8 is a perspective view depicting another exemplary embodiment of implant 103 having a wire-like body 304 with varying thicknesses. Here, it can be seen that generally straight section 305 is relatively thicker than the coiled segments 306 of central portion 303, while interface 333 between generally straight sections 305 and transition sections 331 is relatively thicker still. Relatively thicker regions of body 304, whether formed from a wire, ribbon or other structure, generally have greater strength and less flexibility than relatively thinner regions of body 304. Thus, relatively thicker regions can be used to add strength while relatively thinner regions can be used where added flexibility is desired.

Like the thickness, the surface of body 304 can also be varied as desired. The surface can be modified directly or through etching, grinding, additional coatings or add-ons, which are applied to the underlying body 304. The surface can be modified for any purpose including, but not limited to increasing surface friction with tissue, increasing the ability to engage tissue, allowing tissue in-growth, promoting healing, promoting scarring, promoting thrombogencity, preventing blood passage or shunting around or through implant 103, minimizing thrombus formation, promoting anti-coagulation (e.g., with drugs such as heparin and the like), modifying imaging characteristics (e.g., radio-opacity and the like) and decreasing body surface friction (e.g., with a hydrophilic coating and the like).

Figure 9A:
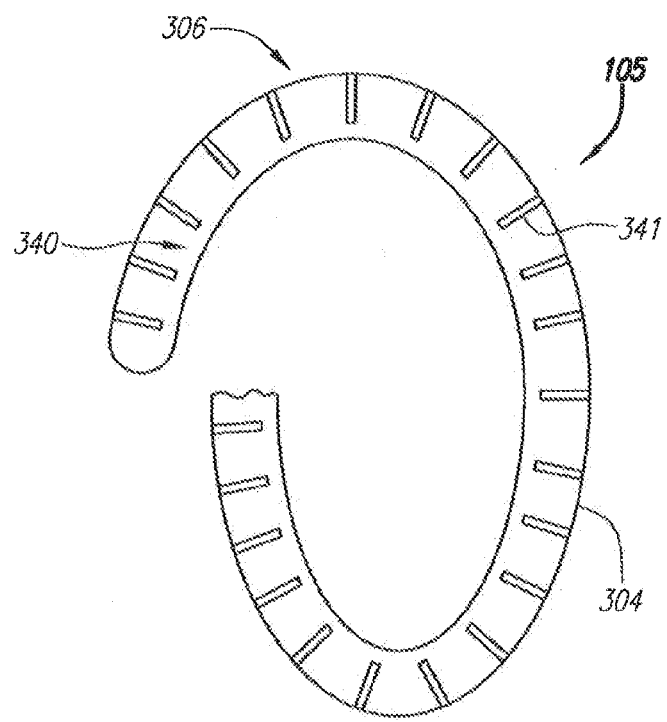
Figure 9B:
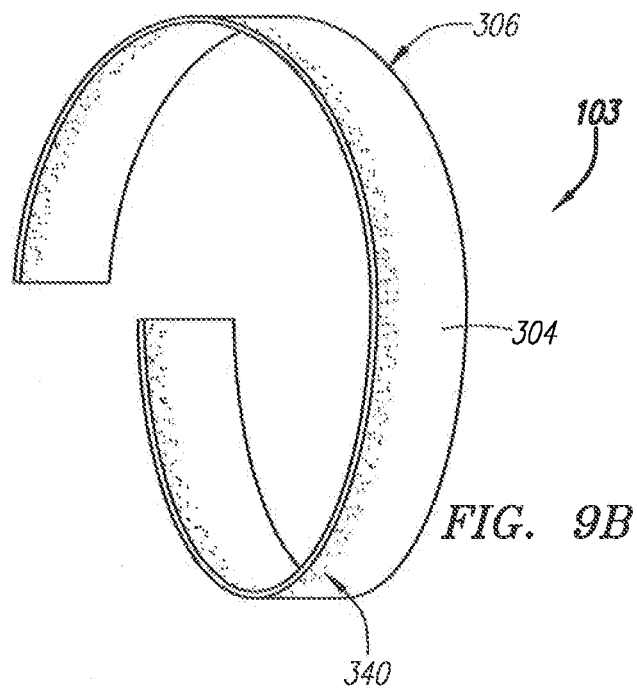
Figure 9C:
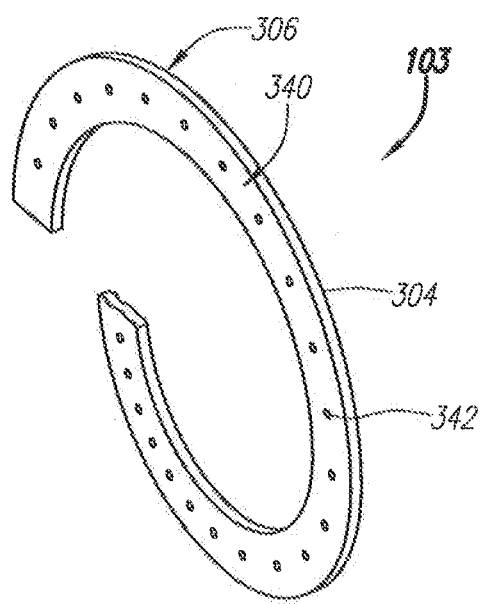

FIGS. 9A-C are perspective views depicting just several additional exemplary embodiments of implant 103 having a modified surface region 340. The surface of implant 103 can be modified in any location and in any manner desired, including, but not limited to, etching, grinding, coating, drilling, and cutting. For instance, FIGS. 9A-C depict the innermost coiled segment 306 of exemplary embodiments of RA/LA portion 301/302. In FIG. 9A, wire-like body 304 has been etched or otherwise treated such that modified surface region 340 is a textured surface including multiple recesses 341 for increasing surface friction and allowing coiled segment 306 to more easily grasp septal wall 207. It should be noted that any surface texture pattern can be used. In FIG. 9B, a coating has been applied to ribbon-like body 304 to create an abrasive surface region 340, also to increase surface friction. In FIG. 9C, apertures 342 in ribbon-like body 304 are present to facilitate tissue in-growth on and around modified surface region 340. Also, in this embodiment the orientation of ribbon-like body 340 has been rotated 90 degrees so that the widest surface is adjacent to the septal tissue.

As stated above, implant 103 can be configured in any manner desired in accordance with the needs of the application. The following is a non-exhaustive list of just some exemplary factors one of skill in the art may consider in designing, configuring, manufacturing and/or otherwise implementing implant 103.

LA portion 302 can be configured to use compressive force 312 from center portion 303 to hold septum primum 214 against septum secundum 210 and at least partially close or seal PFO tunnel 215. LA portion 302 can also be configured to maintain a stable position as central portion 303 and RA portion 301 are deployed without being pulled through septum primum 210 LA portion 302 can be configured to lie flush against septum primum 214 when deployed and not to distort the native geometry of tunnel 215 to create residual shunts. LA portion 302 can be sized to provide adequate coverage over PFO tunnel 215. (In one exemplary embodiment, which is included as an example only and should not be used to limit the invention, LA portion 302 has a maximum width 310 of 1.2 centimeters to accommodate most large PFO tunnels 215.) LA portion 302, in combination with central portion 303 and RA portion. 301, can be configured to exert enough closure force 314 to seal PFO tunnel 215 and prevent shunting during normal and valsalva atrial blood pressures. LA portion 302 can also be configured: to be deployable with minimal and consistent push force (e.g., push force on pusher member 406, which will be described in more detail below); so that the shape before and after deployment is predictable; to be devoid of characteristics that cause chronic or excessive tissue irritation, inflammation, etc.; and/or for visibility during imaging procedures.

Central portion 303 can be configured to maintain LA portion 302 and RA portion 301 in a state of contact with septal wall 207 with enough closure force 312 to at least partially close and seal PFO tunnel 215. Central portion 303 can also be configured: with an adequate spring constant (k) to prevent tunnel 215 from opening during normal and valsalva atrial blood pressures; not to distort the native geometry of tunnel 215 and create residual shunts; to be deployable with minimal and consistent push force (e.g., push force on pusher member 406, which will be described in more detail below); for visibility during imaging procedures; to expand or stretch to accommodate variable septal wall thicknesses without excessive permanent deformation; with adequate strength to withstand any motion it may experience in vivo; to allow LA portion 302 or RA portion 301 to tilt, for instance, if the area of delivery is wedge shaped; so that central portion 303 does not pinch or sever any tissue that could embolize, for instance, with a spring constant low enough to prevent severing tissue; to exert adequate closure force 312 to close any residual shunts that exist; and/or with maximized width 310 and minimized strains to optimize fatigue performance.

RA portion 301 can be configured to hold septum secundum 210 against septum primum 214 and at least partially close or seal PFO tunnel 215. RA portion 301 can also be configured: to lie flush against septum secundum 210 when deployed and not to distort the native geometry of tunnel 215 to create residual shunts; to be deployable with minimal and consistent push force (e.g., push force on pusher member 406, which will be described in more detail below); so that the shape before and after deployment is predictable; to be devoid of characteristics that cause chronic or excessive tissue irritation, inflammation, etc.; for visibility during imaging procedures; and/or to resist being pulled through septal wall 207.

Figure 10A:
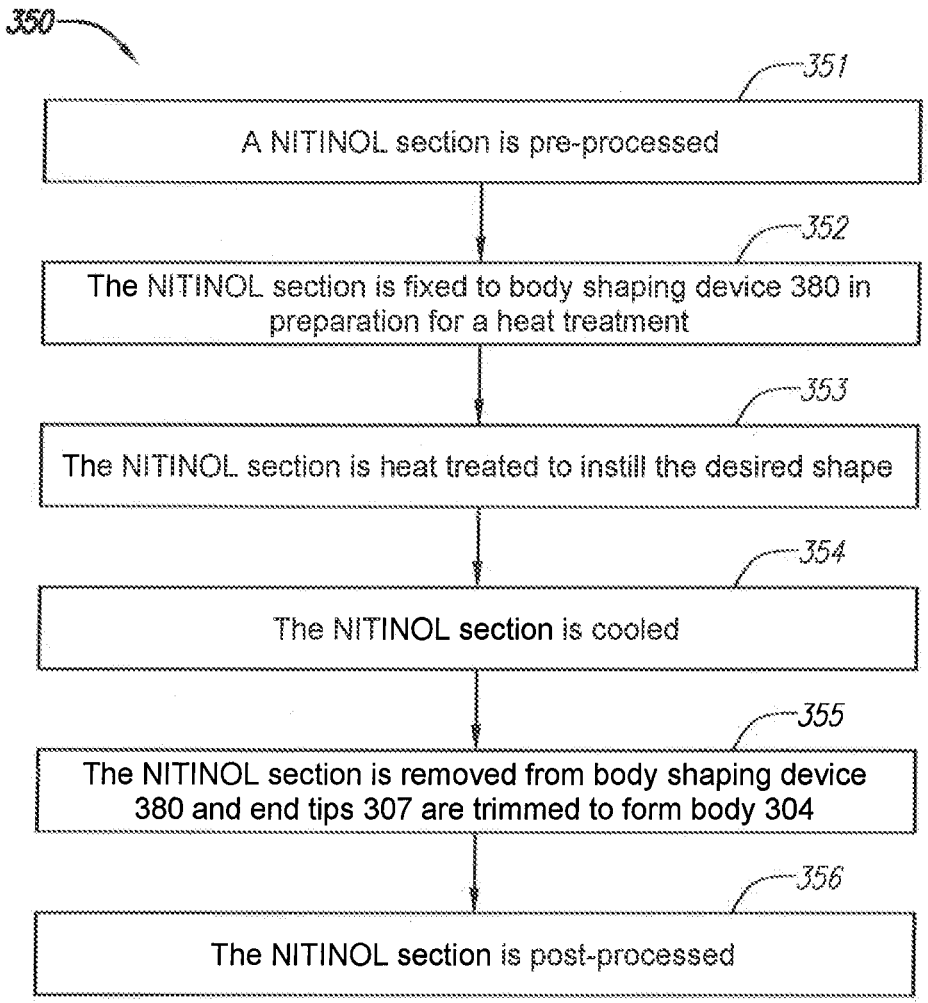
FIG. 10A is a flow diagram depicting one exemplary method of manufacturing another exemplary embodiment of the implantable treatment device.

Also provided herein are methods of manufacturing implant 103. FIG. 10A is a flow diagram depicting one exemplary method 350 of manufacturing an exemplary embodiment of a coil-like implant 103 having body 304, which can be wire, ribbon or the like, composed of NITINOL. First, at 351, a section of NITINOL, from which body 304 can be formed, is pre-processed. Pre-processing 351 can include adding a modified surface region 340 having a desired texture, adjusting body thickness, adjusting the cross-sectional shape of body 304 and the like.

With a ribbon-like implant 103, pre-processing can include etching of the NITINOL section. Methods of etching NITINOL materials are readily understood to one skilled in the art. For instance, a sheet of NITINOL is first etched or grinded or otherwise altered to vary the cross-sectional shape, thickness, surface texture and the like of one or more sections present on the sheet. Etching of the NITINOL sheet can allow for the implementation of numerous different cross-sectional shapes, thicknesses, surface textures and combinations thereof. Afterwards, each section of NITINOL can be cut from the sheet and trimmed as desired.

Figure 10B:
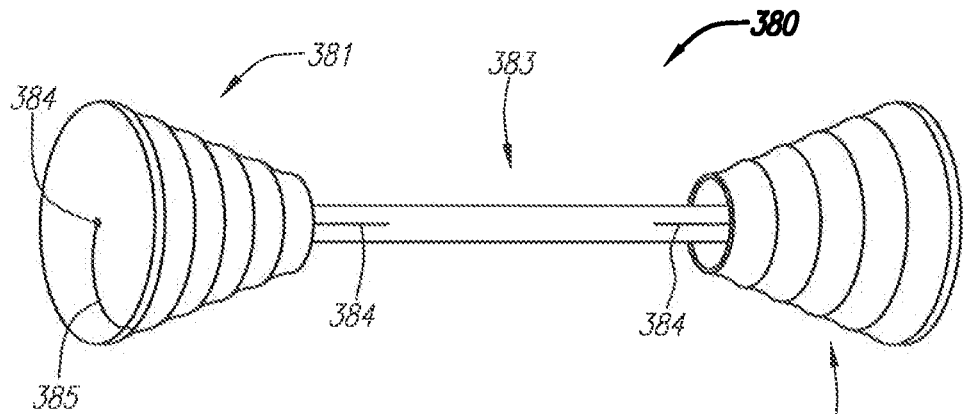
FIG. 10B is a perspective view of an exemplary embodiment of a body shaping device.

At 352, the NITINOL section is fixed to body shaping device 380 in preparation for heat treatment. Heat treatment of NITINOL can instill the desired at rest configuration to body 304 and is well known to those of skill in the art. Accordingly, body shaping device 380 is preferably shaped such that when the NITINOL section is coiled around body shaping device 380, it is in the final desired at rest configuration. One exemplary embodiment of body shaping device 380 is depicted in FIG. 10B. Here, body shaping device 380 is shaped for the exemplary embodiment of implant 103 depicted in FIG. 4A. Body shaping device 380 includes a central body shaping portion 383 corresponding to the shape of central portion 303, and two end body shaping portions 381 and 382 corresponding to the shape of RA portion 301 and LA portion 302, respectively. End body shaping portions 381 and 382 are preferably configured to telescope over central body shaping portion 383 to allow for the inwards manner of coiling of RA/LA portions 301/302 over central portion 303. Central portion 303 includes recesses 384 into which the NITINOL section can be placed to form generally straight sections 305. End body shaping portions 381 and 382 also preferably include recess 385 that can allow for each transition section 331.

Once wrapped around and fixed to body shaping device 380, at 353, the NITINOL section is then preferably heat treated to instill the desired shape. Heat treating can occur at any time and temperature sufficient to instill the desired at rest shape and level of elasticity in implant 103. In one embodiment, which is included as an example only and should in no way be used to limit the invention, heat treating can occur at a temperature range of 500-550 degrees Celsius for approximately five minutes.

At 354, the NITINOL section is preferably cooled, e.g., by rapid quenching in room temperature water, then at 355, the NITINOL section is preferably removed from body shaping device 380 and end tips 307 are trimmed, if necessary, to the desired length to form body 304. Finally, at 356, any post-processing is performed, such as the addition of radio-opaque markers, the shaping of end tips 307 and the addition of any desired coatings or blocking material 326.

Figure 11A:
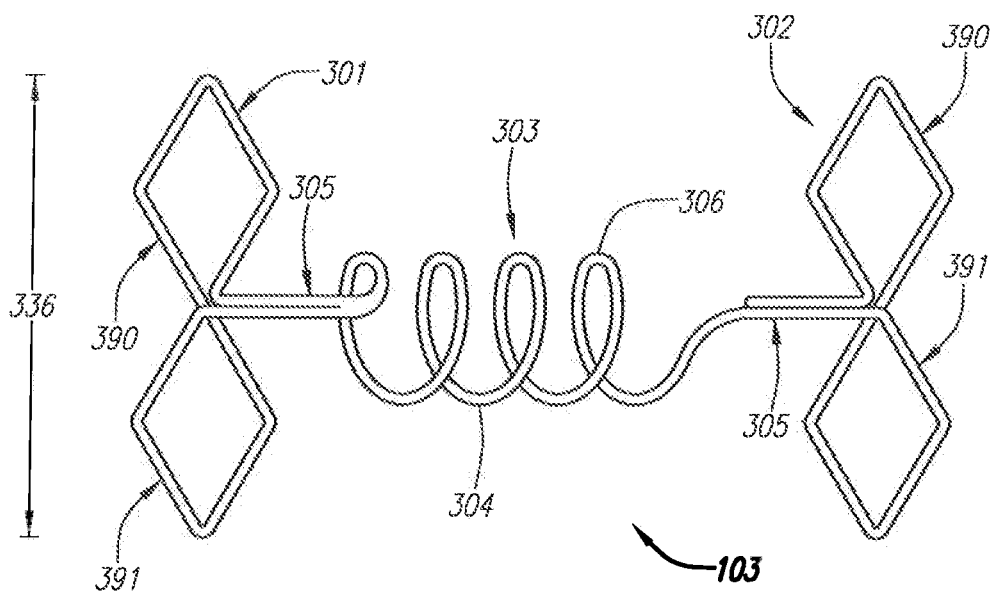
FIGS. 11A-C are perspective views depicting additional exemplary embodiments of an implantable treatment device.
Figure 11B:
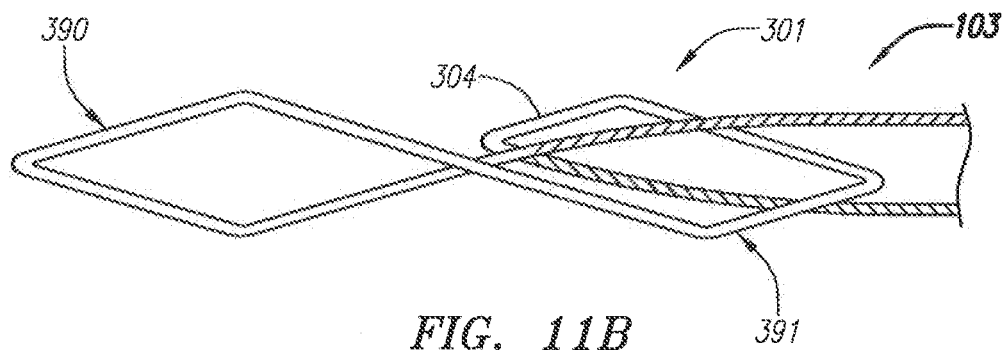
Figure 11C:
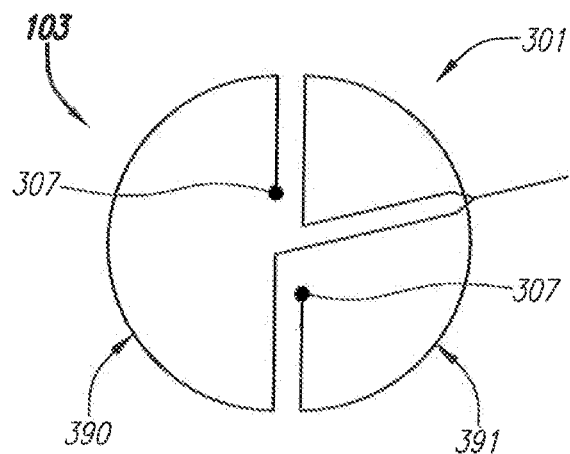

FIGS. 11A-C depict additional exemplary embodiments of implant 103. Specifically, FIG. 11A is a perspective view depicting an exemplary embodiment of implant 103 formed from multiple bodies 304. More specifically, from central portion 303 to RA portion 301 and LA portion 302, body 304 splits into separate wires which are then configured as shaped portions 390 and 391, which in this embodiment have substantially polygonal shapes. The shape and size of polygonal shaped portions 390 and 391 can be configured as desired to facilitate PFO closure. Here, portions 390 and 391 are entirely connected such that implant 103 does not have discrete end tips 307. Polygonal shaped portions 390 and 391 operate similar to coiled segments 306 and are deformable between a housed configuration and an "at rest" deployed configuration as shown here in FIG. 11A. FIG. 11B depicts RA portion 301 in the housed configuration. FIG. 11C depicts another exemplary embodiment where portions 390 and 391 have "D" shapes. Each portion 390 and 391 is not entirely connected and each portion 390 and 391 has an atraumatic end tip 307. It should be noted that body 304 can split into any number of separate portions having any number of configurations. Also, although not shown, implant 103 can include any number of separate bodies 304.

Figure 12:
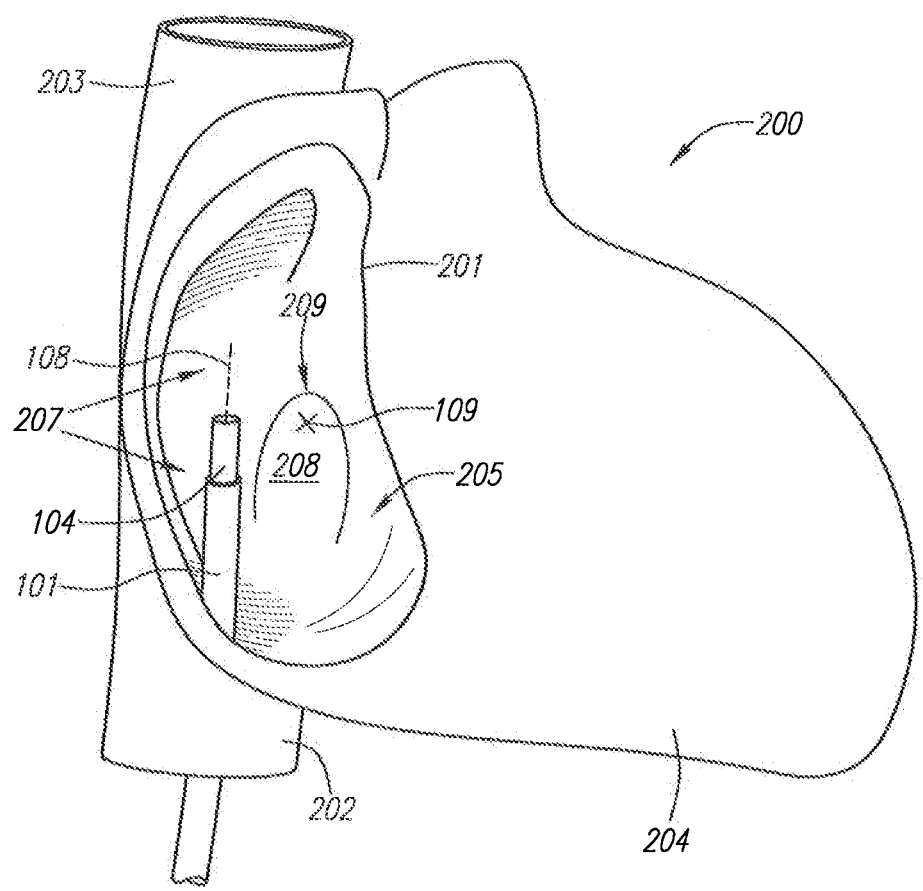
FIG. 12 depicts another exemplary embodiment of the treatment system within a heart.

Turning now to the devices and methods for delivering implant 103, FIG. 12 depicts another exemplary embodiment of treatment system 100 within heart 200. Implant 103 is preferably delivered from right atrium 205, although delivery from left atrium 212 is also possible. Right atrium 205 is preferably accessed via inferior vena cava 202. In this embodiment, implant 103 is delivered from within delivery device 104. To facilitate delivery in this manner, longitudinal axis 108 of delivery device 104 is preferably substantially parallel, i.e., at least close to parallel but not necessarily parallel, to the normal axis 109 of the surface of septal wall 207 into which implant 103 is to be delivered. However, as shown in FIG. 12, longitudinal axis 108 of delivery device 104 is close to perpendicular to this normal axis 109 (shown here extending into the page). To accommodate for this, treatment system 100 is preferably configured for off-axis delivery, which allows the orientation of delivery device 104 to be changed so that the longitudinal axis 108 of delivery device 104 is transverse to the longitudinal axis 107 (not shown) of body member 101.

Figure 13:
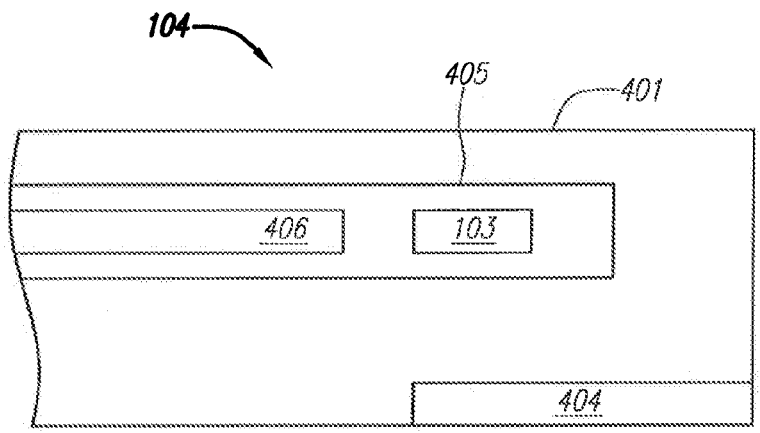
FIG. 13 is a block diagram depicting an exemplary embodiment of a delivery device.

FIG. 13 is a block diagram depicting one exemplary embodiment of delivery device 104 configured for off-axis delivery. Here, delivery device 104 includes an off-axis (OA) delivery member 401. Delivery device 104 is preferably configured to grasp or engage cardiac tissue to support and/or facilitate orientation of delivery member 401. Accordingly, an optional tissue engagement device 404 is included within delivery device 104. Delivery device 104 can also include a needle member 405 for puncturing septal wall 207 and a pusher member 406 for pushing implant 103 from within delivery device 104.

Figure 14A:
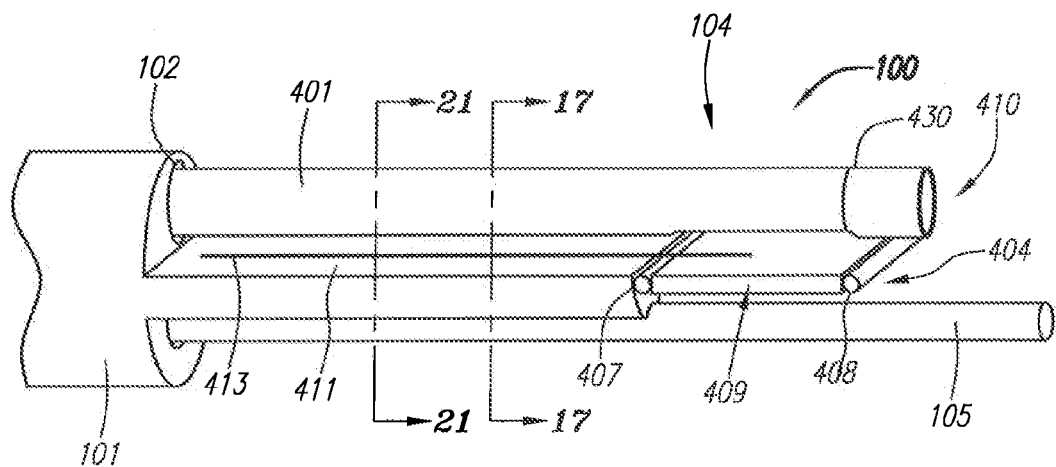
FIG. 14A is a perspective view depicting another exemplary embodiment of the treatment system.

FIG. 14A is a perspective view depicting another exemplary embodiment of treatment system 100, including body member 101, delivery device 104 and stabilization device 105. Here, OA delivery member 401 is an elongate flexible tubular member having open distal end 410. Inner lumen 102 of body member 101 is preferably configured to slidably receive OA delivery member 401, such that OA delivery member 401 can be advanced both proximally and distally. Distal end 410 of OA delivery member 401 is coupled with an elongate support structure 411 of body member 101 via optional grasping device 404. In this embodiment, grasping device 404 includes an arm member 409 coupled with support structure 411 and OA delivery member 401 with hinges 407 and 408, respectively. A biasing element 413 can also be optionally included, to apply a bias force to maintain arm member 409 in the position shown here. Stabilization device 105 is also an elongate member preferably placed in a location to oppose arm member 401.

Figure 14B:
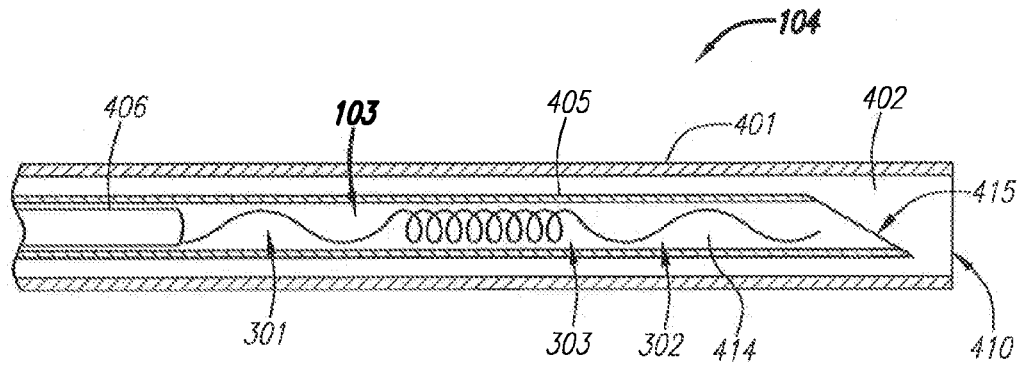
FIG. 14B is a cross-sectional view depicting another exemplary embodiment of the delivery device.

FIG. 14B is a cross-sectional view depicting another exemplary embodiment of OA delivery member 401 with embodiments of needle member 405, pusher member 406 and implant 103 located within lumen 414. Needle member 405 has an open distal end 415 and an inner lumen 414 in which pusher member 406 and implant 103 are slidably received and housed. In this embodiment, implant 103 is deformed to the housed configuration where RA/LA portions 301/302 are relatively straightened but central portion 303 remains in the coiled at rest configuration. As will be discussed in more detail below, delivery of implant 103 is accomplished by first orienting delivery device 104 in the desired orientation transverse to longitudinal axis 107 such that distal end 410 is in proximity with septal wall 207, then advancing needle member 405 through septal wall 207 to create opening 315. After needle member 405 has advanced through septal wall 207 into left atrium 212, pusher member 406 is advanced distally to push LA portion 302 of implant 103 from within lumen 414. Once LA portion 302 is outside lumen 414, LA portion 302 returns to the coiled at rest configuration. Needle member 405 can then be retracted proximally such that LA portion 302 engages septal wall 207 and remains in left atrium 212. As needle member 405 is retracted through septal wall 207, central portion 303 deploys within opening 315. Once needle member 405 is retracted back into lumen 402, OA delivery member 401 can be retracted from septal wall 207, for instance by pulling body member 101 proximally back, thereby allowing RA portion 301 to deploy and engage septal wall 207 in a coiled configuration.

Figure 14C:
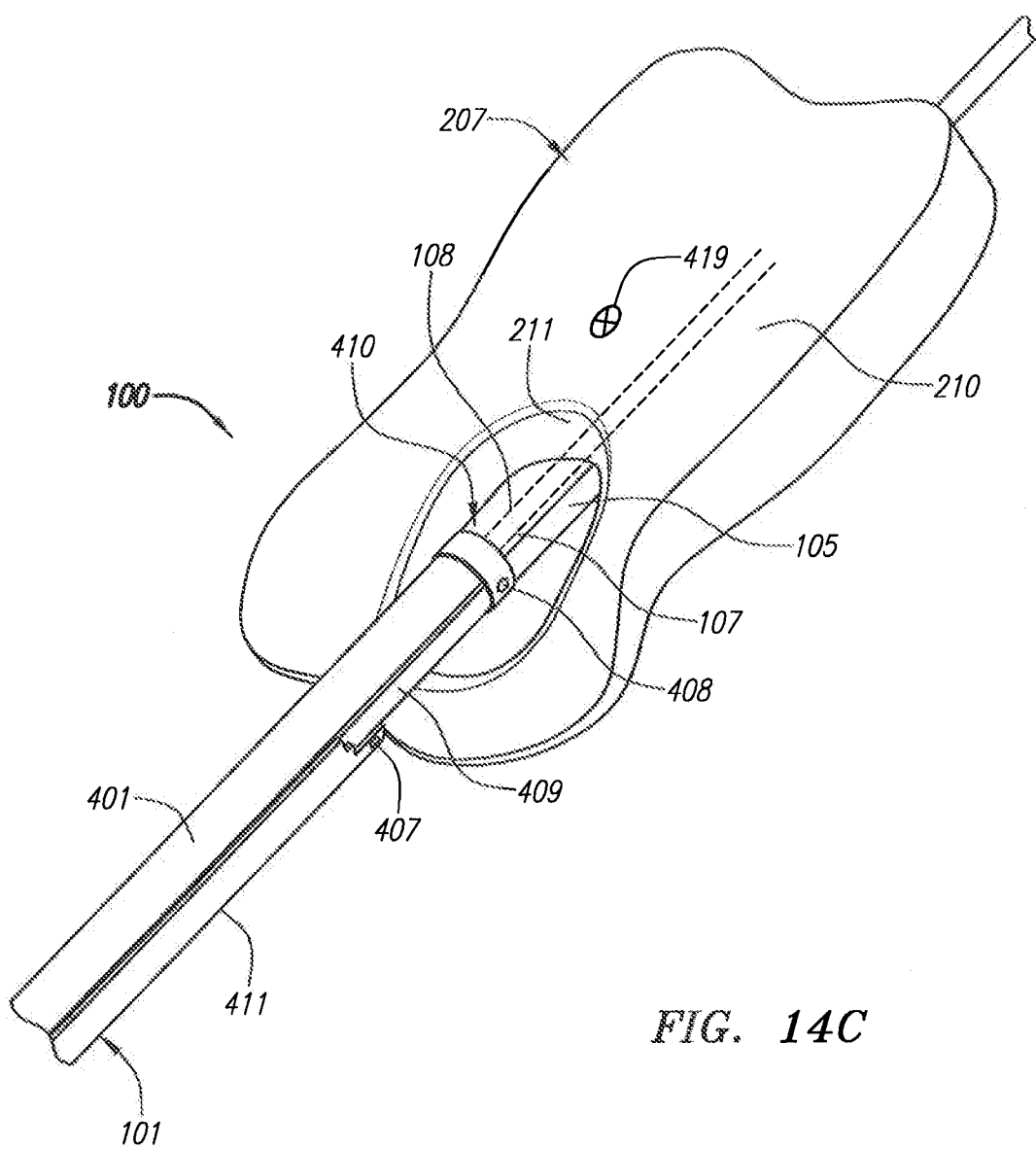
FIGS. 14C-F are perspective views depicting a portion of the septal wall and an additional exemplary embodiment of the treatment system.
Figure 14D:
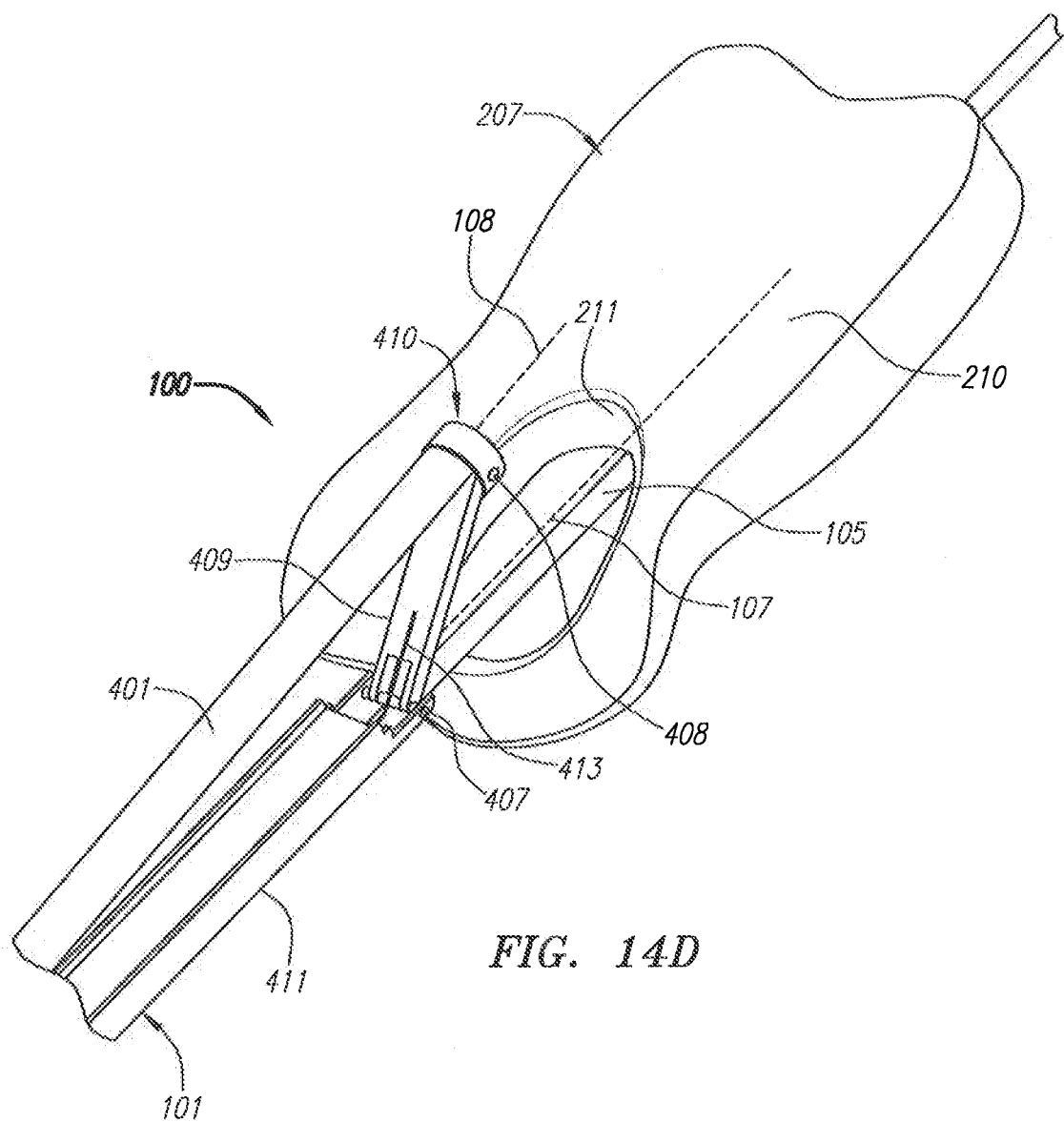
Figure 14E:
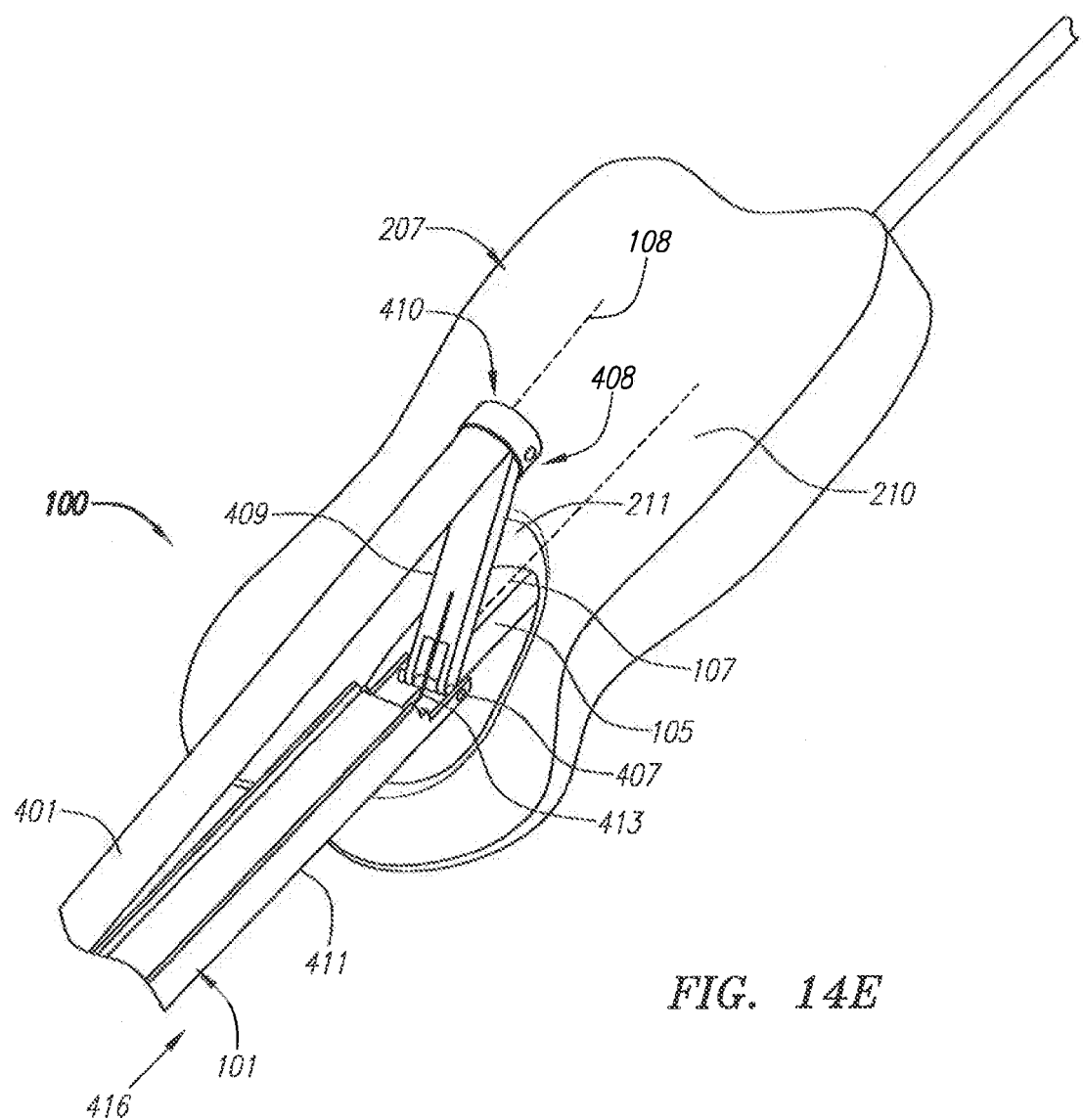

FIGS. 14C-F are perspective views depicting a portion of septal wall 207 and an additional exemplary embodiment of treatment system 100 during use of delivery device 104 prior to insertion of needle member 405. Here, the preferred location for insertion of needle member 405 is indicated by location 419. FIG. 14C depicts treatment system 100 with delivery device 401 in the on-axis position, where the longitudinal axes 107-108 are generally or substantially parallel. Stabilization device 105, the use and structure of which will be described in more detail below, is shown positioned within PFO tunnel 215. In FIG. 14D, OA delivery member 401 has been retracted proximally with respect to body member 101 and in opposition to bias member 413, causing distal end 410 to move away from stabilization device 105 by way of arm member 409 and hinges 407-408. In FIG. 14E, treatment system 100 is advanced distally in direction 416 until the underside surface 417 of arm member 409 abuts limbus 211, at which point OA delivery member 401 can be advanced distally with respect to body member 101 to force arm member 409 back towards stabilization device 105 to clamp, or grasp limbus 211 between arm member 409 and stabilization device 105, which is preferably in a substantially fixed position with respect to arm member 409. By grasping limbus 211 in this manner, treatment system is effectively anchored to septal wall 207.

Figure 14F:
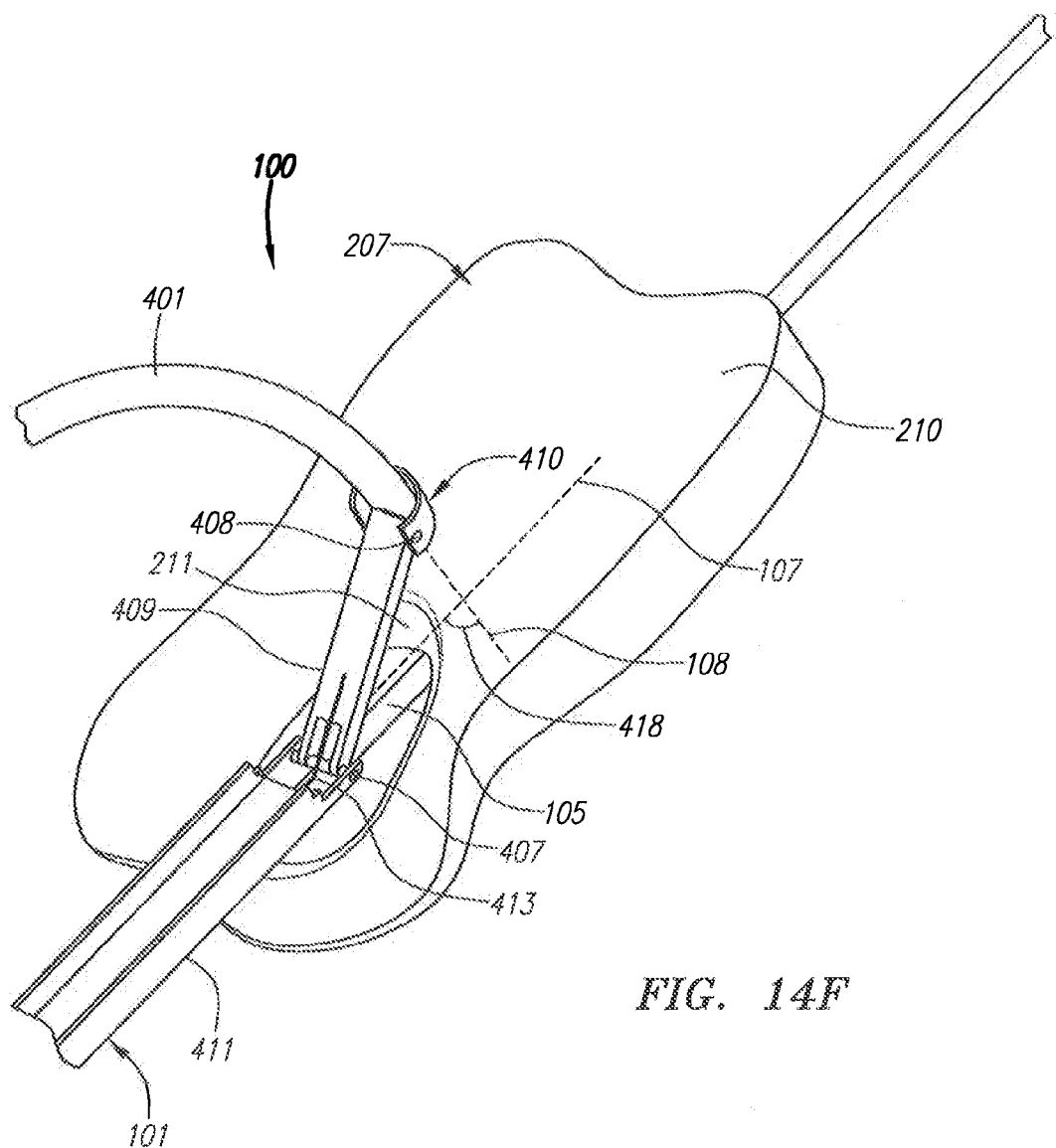

In FIG. 14F, OA delivery member 401 is further advanced distally with respect to body member 101, which causes OA delivery member to deflect or arc outwards, in order to rotate distal end 410 about hinge 408 into the desired orientation with respect to septal wall 207. Distal end 410 is now preferably in contact with septal wall 207 at the desired needle insertion location 419. As shown here, OA delivery member 401 is in an outwardly arced state. The degree to which OA delivery member 401 arcs outwards can be adjusted by altering the length of OA delivery member 401 present outside of body member 101. Because needle member 405, pusher member 406 and implant 103 all preferably move within OA delivery member 401, the radius of curvature of the arc is preferably kept large enough to allow movement within OA delivery member 401. A very large radius of curvature can result in sharp angles or kinking in OA delivery member 401 that can make movement difficult.

As shown in FIG. 14F, longitudinal axis 108, as measured at distal end 410, is now transverse to longitudinal axis 107. Preferably, the delivery angle 418, which is the angle between longitudinal axis 107 and longitudinal axis 108 as measured at distal end 410, is approximately 90 degrees. Once distal end 410 is in the desired orientation, needle member 405 can be advanced into septal wall 207.

The needle insertion location 419 can be placed in any desired location, but should be chosen based in part on the configuration and size of implant 103 and the degree of overlap between septum primum 214 and septum secundum 210. For instance, in one exemplary embodiment, which is included for illustration only and in no way should be used to limit the invention, needle insertion location 419 is placed between 3 and 7 mm from limbus 211. The position of needle insertion location 419 can be determined by the length of arm member 409, which in turn can position distal end 410 using limbus 211 as a point of reference. To allow for added flexibility, the length of arm member 409 can be configured to be adjustable during the implantation procedure. Thus, arm member 409 is preferably configured for at least two functions: (1) to stop travel of body member 101 at limbus 211 by abutting limbus 211 and (2) to position distal end 410 in the desired needle insertion location 419.

Figure 15A:
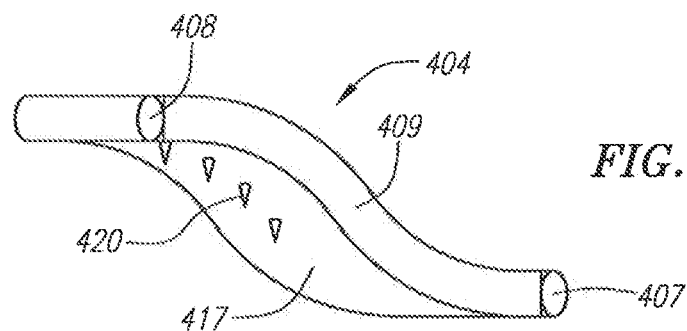
FIGS. 15A-D are perspective views depicting additional exemplary embodiments of the delivery device.

FIGS. 15A-D are perspective views depicting additional exemplary embodiments of grasping device 404 in a pulled back position. In FIG. 15A, arm member 409 is configured to engage limbus 211 with a contoured undersurface 417 that accommodates the shape of limbus 211 in order to facilitate grasping or engagement. Undersurface 417 can also be textured as desired to increase surface friction, or made lubricious to assist in friction-free centering, and, as shown here, undersurface can include abutments 420 configured to fixably grasp limbus 211. Also, it should be noted that any type of hinges 407-408 can be used including, but not limited to, the swivel type hinges depicted here.

Figure 15B:
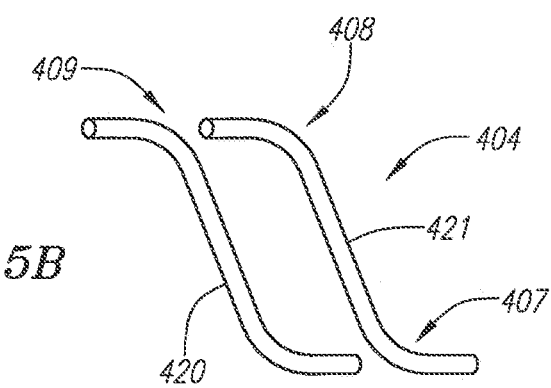
Figure 15C:
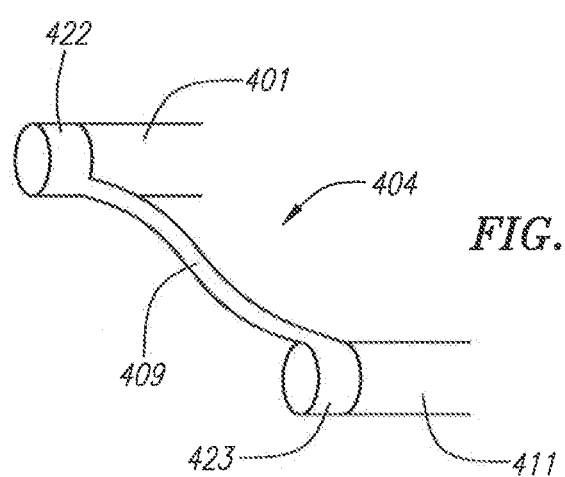

FIGS. 15B-C depict exemplary embodiments of grasping device 404 where hinges 407 and 408 are integrated into arm member 409. In FIG. 15B, arm member 409 includes two elastic wires 421 each configured to flex at hinge positions 407 and 408, e.g., by reducing the thickness of the material at the hinge positions. Arm member 409 is preferably biased towards a downwards position, which can allow elimination of any additional biasing element 413. In FIG. 15C, arm member 409 is configured to be both flexible and stretchable and can be composed of an elastomeric or rubber-like material or thin or slotted metal or polymeric material with the appropriate modulus. This flexibility and stretchability facilitates the conformance of arm member 409 to limbus 211. Here, arm member 409 includes tubular portions 422 and 423 for coupling arm member 409 with OA delivery member 401 and support structure 411, respectively.

Figure 15D:
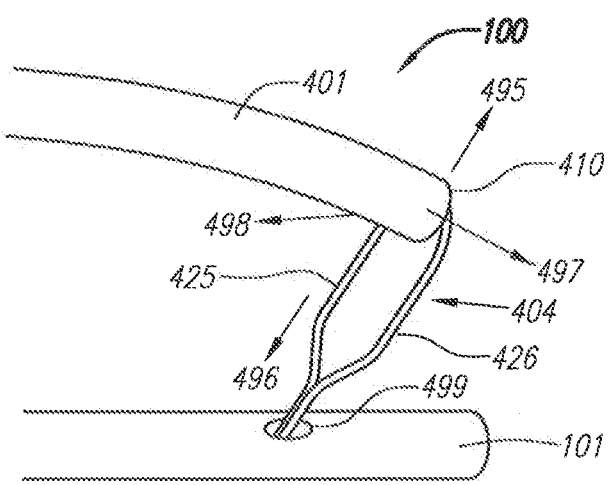

FIG. 15D is a perspective view depicting yet another exemplary embodiment of grasping device 404. Here, arm member 409 again includes two flexible wires 420 and 421 that can be coupled with OA delivery member 401. Like the embodiment described with respect to FIG. 15B, hinges 407 and 408 can be integrated into wires 420 and 421, which can be biased towards a downwards position. As shown in FIG. 15D, wires 425 and 426 are preferably routed through aperture 499 into a lumen 102 within body member 101 and to the proximal end of body member 101, where they can be independently adjusted to control, or steer, OA delivery member 401. For instance, distal movement of both wires 425 and 426 moves distal end 410 of OA delivery member 401 in direction 495 and proximal movement of both wires 425 and 426 moves distal end 410 of OA delivery member 401 in direction 496, as OA delivery member 401 permits. Distal advancement of wire 425 with respect to wire 426, alone or in combination with proximal movement of wire 426 with respect to wire 425, moves distal end 410 in lateral direction 497, while reverse movement moves distal end 410 in lateral direction 498, as OA delivery member 401 permits.

Figure 16A:
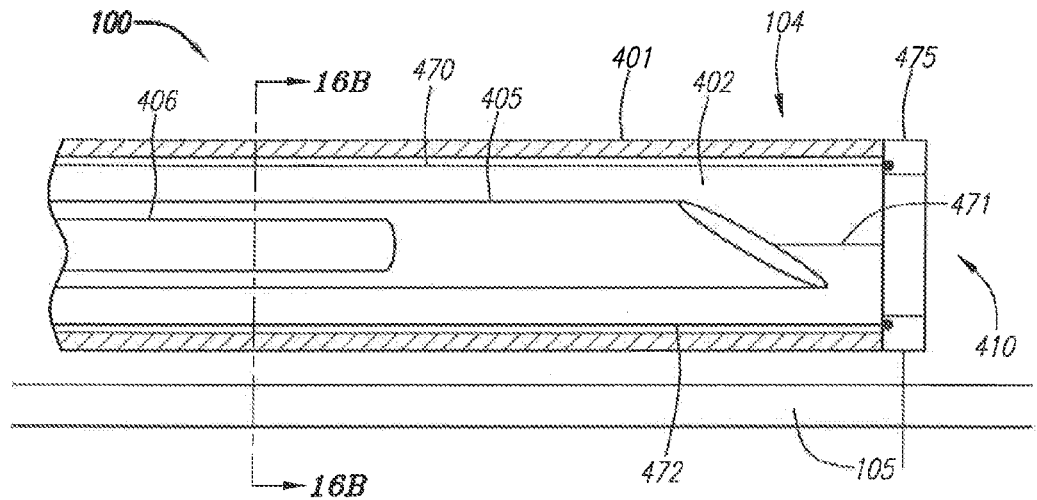
FIGS. 16A-B are cross-sectional views depicting additional exemplary embodiments of the treatment system.
Figure 16B:
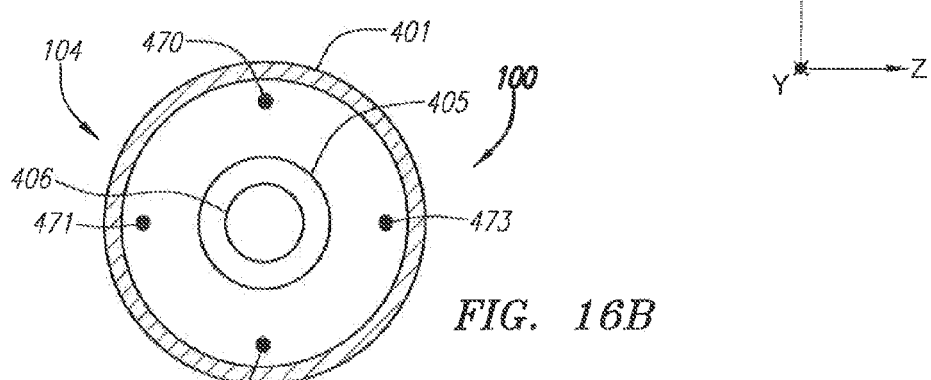

FIGS. 16A-B are cross-sectional views depicting additional exemplary embodiments of treatment system 100 with delivery device 104. FIG. 16A depicts a longitudinal cross-sectional view of treatment system 100 and FIG. 16B depicts a radial cross-sectional view of treatment system 100 taken along line 16B-16B of FIG. 16A. Here, delivery device 104 includes a steerable OA delivery member 401, which is configured to be freely steerable to position distal end 410 in the desired orientation at needle insertion location 419. Accordingly, distal end 410 is preferably left unconnected with any grasping device 404 (not shown). Preferably, steerability is provided through the use of one or more pull wires 424 coupled with distal end cap 475. In this embodiment, four pull wires 470-473 are equally spaced apart from each other within lumen 402. This configuration allows for manipulation of distal end 410 to any three-dimensional (X, Y, Z) orientation. For instance, pulling wire 470 back proximally with respect to wires 471-473, or pulling wire 472 back proximally with respect to wires 470-471 and 473 allows movement of distal end 410 in the X-Z plane. Pulling wire 471 back proximally with respect to wires 470 and 472-473, or pulling wire 473 back proximally with respect to wires 470-472 allows movement of distal end 410 in the Y-Z plane.

Figure 16C:
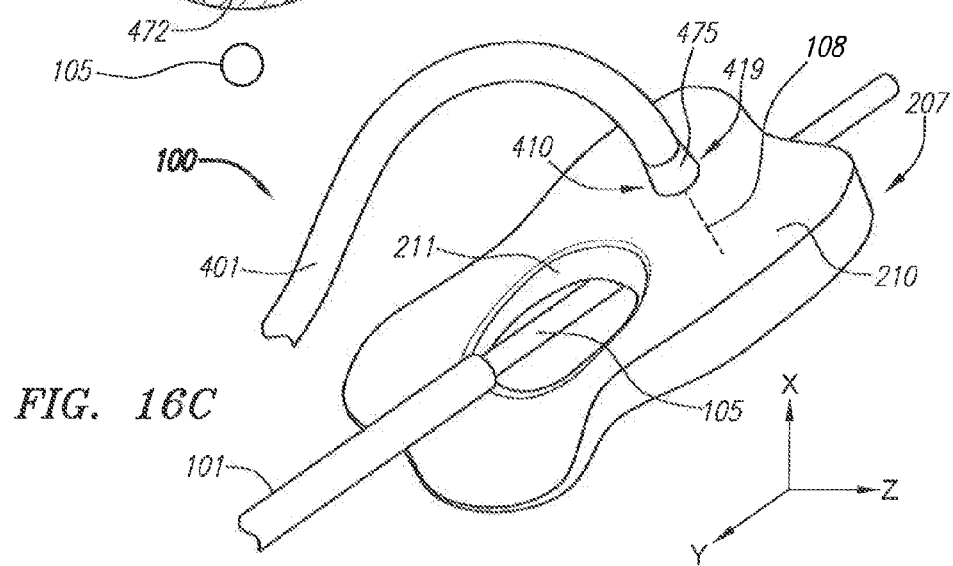
FIG. 16C is a perspective view depicting the embodiment described with respect to FIGS. 16A-B during delivery.

FIG. 16C is a perspective view depicting the embodiment described with respect to FIGS. 16A-B during delivery. Here, distal end 410 has been oriented in its needle insertion location 419 and longitudinal axis 108 lies within both the X-Z and Y-Z planes. The degree of steerability can be altered as desired for each individual application. For instance, the inclusion of additional pull back wires can provide for more finely controllable steerability, while the deletion of any of pull wires 470-473 can eliminate freedom of steerability, but can simplify the overall design of device 104. The design and use of steerable devices is also discussed in parent U.S. patent application Ser. No. 10/847,747, filed on May 7, 2004.

As mentioned above, OA delivery member 401 is preferably configured to allow slidable movement of needle member 405, pusher member 406 and implant 103 within inner lumen 402. Preferably, OA delivery member 401 is configured so as to maintain a sufficient degree of structural integrity and kink resistance, while at the same time providing adequate torque or twist control. In one exemplary embodiment, OA delivery member 401 is composed of a flexible braided metal reinforced polymeric tube configured to provide the desired amount of kink resistance and torque control. In other exemplary embodiments, OA delivery member 401 can be composed of a braided or unbraided polymeric tube. In yet another exemplary embodiment, OA delivery member 401 is composed of a metal tube having apertures located therein to provide added flexibility. For instance, OA delivery member 401 can be a NITINOL slotted tube, with the size and spacing of each slot configured for optimal flexibility, kink resistance and torque control. The apertures are preferably placed in a location corresponding to the portion of OA delivery member 401 that extends or arcs out, while the portion of OA delivery member 401 proximal to this can be left solid without apertures to maintain resilience in OA delivery member 401 and provide resistance to push back from needle member 405 as it penetrates septal wall 207.

Figure 17:
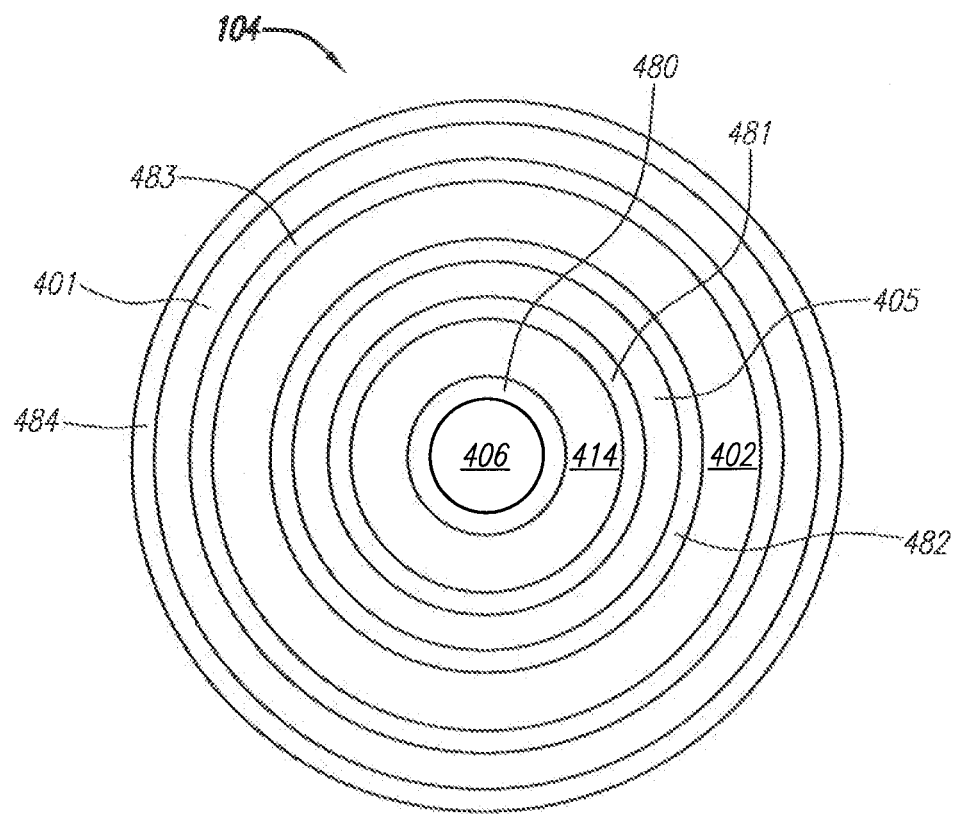
FIG. 17 is a cross-sectional view depicting an exemplary embodiment of the delivery device taken along line 17-17 of FIG. 14A.

Furthermore, OA delivery member 401 can be coated to provide low friction surfaces to facilitate advancement of OA delivery member 401 within body member 101 and the patient's body, as well as to facilitate movement of needle member 405 within lumen 402. Pusher member 406 and needle member 405 can be coated as well. For instance, FIG. 17 is a cross-sectional view depicting an exemplary embodiment of OA delivery member 401 taken along line 17-17 of FIG. 14A. Here, pusher member 406 includes an outer coating 480, needle member 405 includes both an inner coating 481 and an outer coating 482 and OA delivery member 401 includes both an inner coating 483 and an outer coating 484. Coatings 480-484 can be implemented for any purpose desired. For instance, in one embodiment, coatings 480-484 are composed of any material used to lower surface friction, including, but not limited to polymers such as polyethylene (PE), polytetrafluoroethylene, fluorinated ethylenelpropylene copolymers, silicones, hydrogels, hydrophilic coatings or polyurethane (PU) and the like. Preferably, a high density PE material is used that is thin enough to provide the desired degree of flexibility while at the same time providing a low friction surface.

Like OA delivery member 401, needle member 405 and pusher member 406 are also preferably flexible elongate members. FIG. 18A is a cross-sectional view of an exemplary embodiment of needle member 405. Distal end 415 of needle member 405 is preferably substantially sharp enough to penetrate the desired portion of septal wall 207. In this embodiment, distal end 415 is tapered similar to a conventional needle. Also, needle member 405 is preferably flexible enough to move within OA delivery member 401 when deflected for off-axis delivery.

For instance, needle member 405 can include one or more openings, or apertures 436, to increase flexibility. Here, needle member 405 includes multiple apertures 436 in various arrangements. Needle member 405 can be fabricated from any desired material including, but not limited to, NITINOL and stainless steel, and apertures 436 can be formed in any manner including, but not limited to, molding, milling, grinding, laser cutting, EDM, chemical etching, punching and drilling. The design and use of flexible needles is also discussed in parent U.S. patent application Ser. No. 10/847,747, filed on May 7, 2004.

A first region 437 of needle member 405 includes apertures 436 located at various intervals around the circumference of needle member 405. A second region 438, located distal to the first region 437, includes apertures 436 on the lower portion of needle member 405. FIG. 18B is a cross-sectional view depicting an exemplary embodiment of needle member 405 in a deflected state within an exemplary embodiment of OA delivery member 401. Because apertures 436 in region 437 are located around the circumference of needle member 405, region 437 is relatively more flexible than region 438. In region 438, placement of apertures 436 on the lower surface, reduces the possibility that implant 103 will catch or snag an aperture 436 during advancement of needle member 405 from OA delivery member 401. In addition, distal tip 439 of needle member 405 is also preferably aligned on the lower portion of needle member 405 to reduce the possibility that distal tip 439 will impact, catch, snag, or damage OA delivery member 401.

Treatment system 100 can be configured to apply a suction-type force to any surface of septal wall 207 to allow needle member 405 to more easily penetrate the septal tissue without excessive "tenting" of septal wall 207 in response to the pressure applied by needle member 405. For instance, the proximal end of OA delivery member 401 can be coupled with a vacuum or pressure adjustment device configured to lower the air or fluid pressure within OA delivery member 401. The pressure is preferably lowered to a degree sufficient to create a suction-type force between OA delivery member 401 and septal wall 207 thereby keeping septal wall 207 in contact or in proximity with OA delivery member 401 while needle member 405 is advanced into septal wall 207. Also, the suction-type force can be applied through needle member 405 instead of or in addition to OA delivery member 401.

Treatment system 100 preferably includes one or more sensors to facilitate determination of when needle member 405 has entered left atrium 212. For instance, in one exemplary embodiment, needle member 405 includes a sensor at or near distal end 415. The sensor can be any type of applicable sensor, such as a pressure sensor, thermal sensor, imaging device, acoustic device and the like. In one exemplary embodiment, a pressure sensor is included that is configured to sense the blood pressure change between right atrium 205 and left atrium 212. The pressure sensor can be any type of pressure sensor including, but not limited to, an electrical sensor and a fluid feedback sensor such as a lumen within needle member 405 having an open distal end in fluid communication with the exterior environment. In an alternative exemplary embodiment, distal end 415 of needle member 405 is configured to be visible by an external or internal imaging device, which can then be used to track the position of distal end 415 with respect to septal wall 207.

Figure 18C:
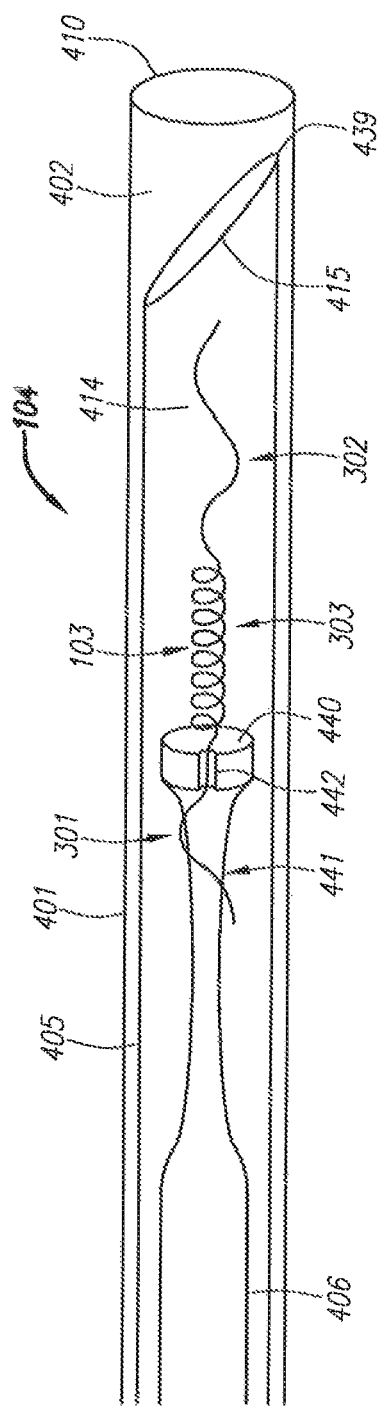

FIG. 18C is a cross-sectional view of another exemplary embodiment of delivery device 104. Here, distal end 440 of pusher member 406 is configured to push against central portion 303 of implant 103 as opposed to end tip 307 of RA portion 301. This reduces the likelihood that RA portion 301 will coil when pushed within lumen 414, which could result in bunching of implant 103 within lumen 414 making delivery more difficult. Because distal end 440 of pusher member 406 is located distal to RA portion 301, pusher member 406 includes a relatively thinner portion 441 that can provide additional room for RA portion 301 within lumen 414 as well as provide added flexibility to pusher member 406. Relatively thinner portion 441 is relatively thinner than distal end 440, which is preferably thick enough to adequately engage central portion 303. Distal end 440 can include a recess 442 to provide enough room for RA portion 301. Recess 442 can also be used to help position implant 103 during delivery. For instance, rotation of pusher member 406 can cause implant 103 to rotate if implant 103 is still routed through recess 442. This can allow the proper rotational orientation of implant 103 before or during delivery into septal wall 207. Distal end surface 443 can be configured in any manner desired to facilitate proper contact and engagement of implant 103.

Figure 19A:
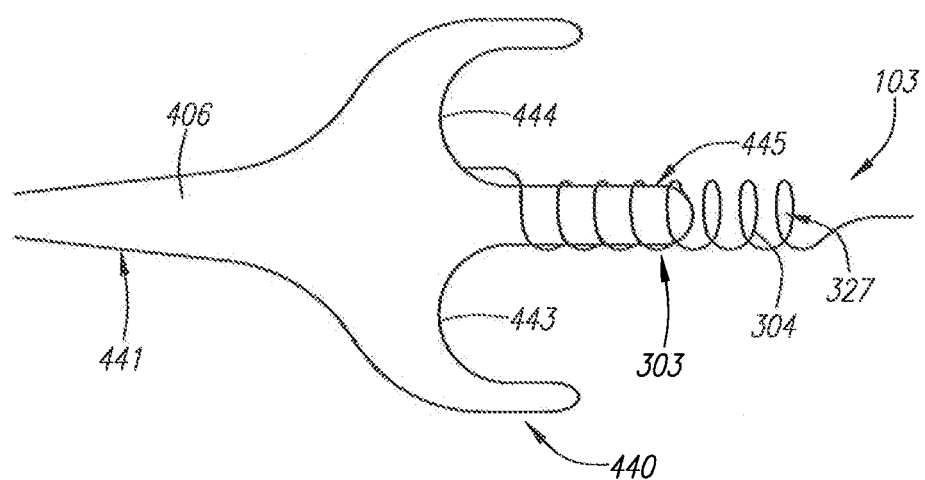
FIGS. 19A-B are cross-sectional views depicting exemplary embodiments of a delivery device and an implantable treatment device.
Figure 19B:
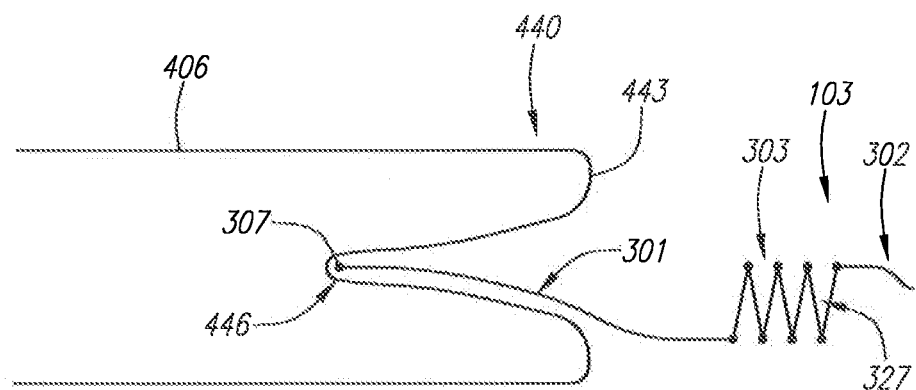

For instance, FIGS. 19A-B are cross-sectional views depicting exemplary embodiments of pusher member 406 and implant 103. In FIG. 19A, distal end surface 443 is contoured with a rounded recessed portion 444 into which a coiled central portion 303 can rest and an elevated portion 445 configured to fit within open interior region 327. As one of skill in the art will readily recognize, the contours of distal end surface 443 are dependent on the type and housed configuration of implant 103, as well as the desired point of contact on implant 103. In FIG. 19B, distal end surface 443 is contoured with a narrow recessed portion 446 into which end tip 307 of RA portion 301 can rest.

Pusher member 406 can also be configured to releasably couple with implant 103. For instance, in one exemplary embodiment, pusher member 406 is tethered to implant 103 with a tether 485 in order to allow implant 103 to be drawn back into needle member 405 if needed, such as in a case of improper deployment. If implant 103 is properly deployed, tether 485 can be released from pusher member 406, in another exemplary embodiment, pusher member 406 can be configured to both push and pull implant 103 while within needle member 405, as depicted in FIGS. 20A-B.

Figure 20A:
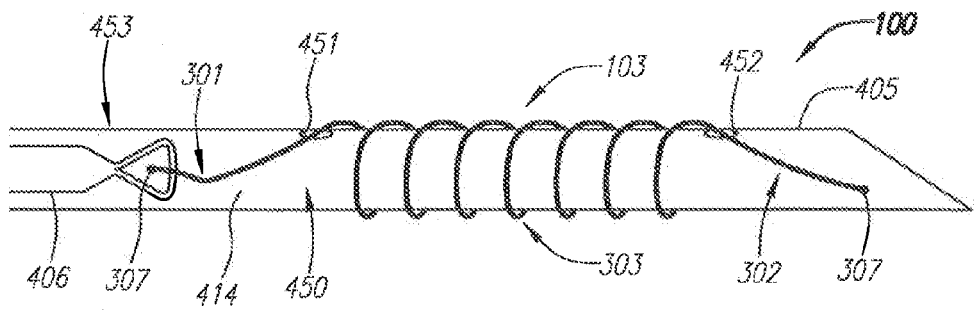
FIGS. 20A-B are schematic views depicting additional exemplary embodiments of a delivery device and an implantable treatment device.
Figure 20B:
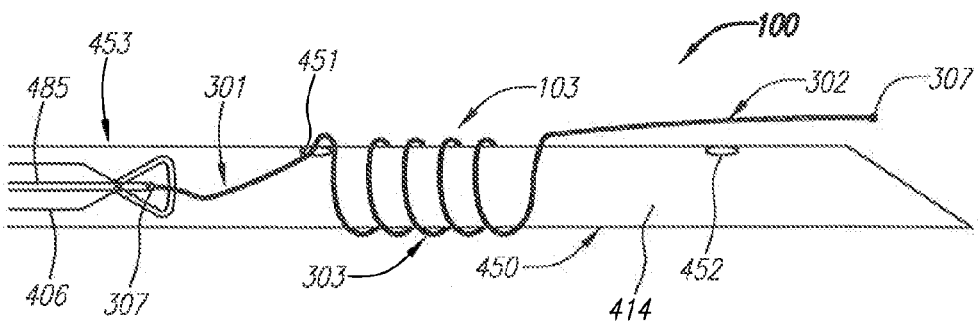

FIGS. 20A-B are schematic views depicting additional exemplary embodiments of needle member 405, pusher member 406 and implant 103. In FIG. 20A, implant 103 is placed over outer surface 450 of needle member 405 and end tips 307 of RA portion 301 and LA portion 302 can be routed through apertures 451 and 452, respectively, and housed within lumen 414. To deliver implant 103, after needle member 405 has traversed septal wall 207 into left atrium 212, pusher member 406 is used to pull implant 103 hack proximally to expose end tip 307 of LA portion 302 as depicted in FIG. 20B. To grasp end tip 307, pusher member 406 can include any type of grasping device desired. Here, pusher member 406 includes a clamp-type device 453. Once removed from aperture 452, LA portion 302 can enter the coiled state. As needle member 405 is withdrawn back through septal wall 207, LA portion 302 engages septal wall 207 and cause implant 103 to slide off needle member 405. Pusher member 406 can also be used to push end tip 307 of RA portion 301 to facilitate deployment. In this embodiment, proximally locate end tip 307 includes an aperture through which a tether 485 is routed for use as described above.

Figure 21:
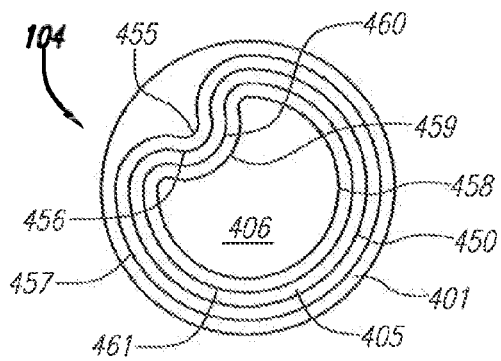
FIG. 21 is a cross-sectional view depicting another exemplary embodiment of a delivery device taken along lines 21-21 of FIG. 14A.

Delivery device 104 can be configured to maintain the proper orientation of OA delivery member 401, needle member 405, pusher member 406 and implant 103 during delivery. FIG. 21 is a cross-sectional view depicting another exemplary embodiment of delivery device 104 taken along lines 21-21 of FIG. 14A where delivery device 104 is configured to use a lock and key technique to maintain proper orientation. Here, the lock and keys are implemented with a combination of abutments and corresponding recesses. For instance, outer surface 450 of needle member 405 includes a recess 456 configured to receive an abutment 455 located on inner surface 457 of OA delivery member 401. Recess 456 can extend longitudinally along needle member 405 for any desired distance to ensure proper orientation even when needle member 405 is advanced and retracted within OA delivery member 401. Similarly, outer surface 458 of pusher member 406 includes a recess 459 configured to receive an abutment 460 located on inner surface 461 of needle member 405. Like recess 456, recess 459 can extend longitudinally along pusher member 406 for any desired distance to ensure proper orientation when pusher member 406 is advanced and retracted. As discussed above with respect to FIGS. 18A-13, pusher member 406 can include recess 442 to accommodate for the presence of RA portion 301. This recess 442 can also maintain implant 103 in the proper orientation with respect to pusher member 406.

The distances that OA delivery member 401, needle member 405 and pusher member 406 are moved proximally and distally with respect to body member 101, can be relatively small. Manual movement of these components, while possible, can be difficult. Treatment system 100 can include one or more automated systems or devices at the proximal end of body member 101 to facilitate movement of these components and lessen the risk that each component is inadvertently advanced too far or not enough. The automated systems or devices can also be configured to apply the desired amount of force to move each component and sense if too much force is being used, which could be indicative of an error in the delivery process.

To further facilitate movement of OA delivery member 401, needle member 405 and pusher member 406, each can be optionally preshaped. For instance, in one exemplary embodiment, one or more of OA delivery member 401, needle member 405 and pusher member 406 can include a curved section that corresponds to the desired deflected arc shape of OA delivery member 401 depicted in FIG. 14F.

It should also be noted that needle member 405 can be excluded from system 100 altogether. Pusher member 406 can deploy implant 103 through a pre-existing hole, or implant 103 can be configured with a substantially sharp end tip 307 for creation of a hole while being deployed by pusher member 406.

Figure 22:
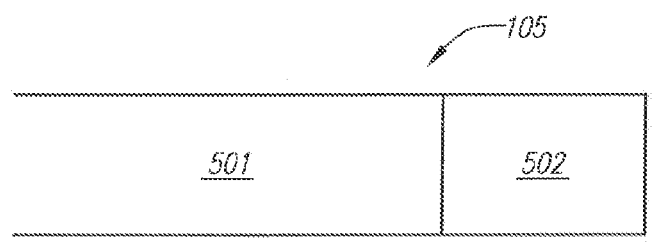
FIG. 22 is a block diagram depicting an exemplary embodiment of a stabilization device.

As described with respect to FIG. 1, treatment system 100 can optionally include stabilization device 105. FIG. 22 is a block diagram depicting an exemplary embodiment of stabilization device 105 within treatment system 100. Here, stabilization device 105 is preferably configured to stabilize treatment system 100 during delivery of implant 103. Stabilization device 105 can have any configuration desired in accordance with the needs of the application. For instance, stabilization device 105 can be configured as a body routed through PFO tunnel 215 or any portion of the patient's vasculature, such as superior vena cava 203. Stabilization device 105 preferably includes an elongate stabilization member 501 and can optionally include grasping device 502, which is preferably configured to grasp nearby tissue in order to facilitate stabilization.

Figure 23A:
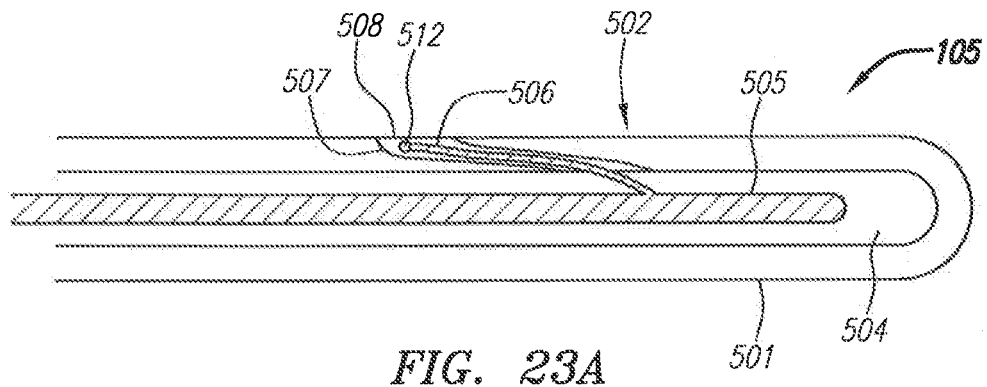
FIGS. 23A-C are cross-sectional views depicting additional exemplary embodiments of a stabilization device.
Figure 23B:
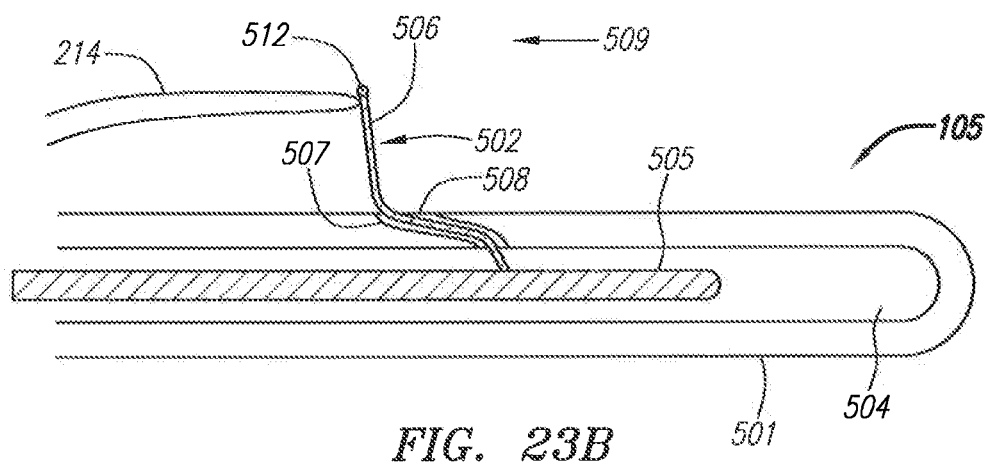
Figure 23C:
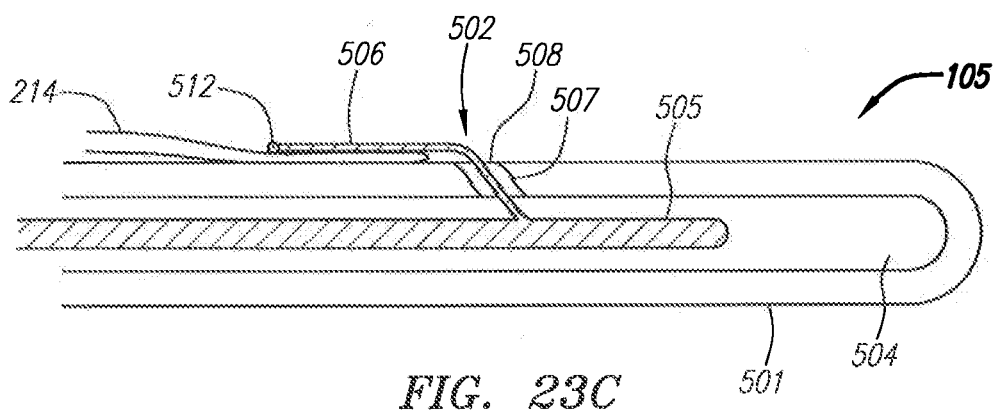

FIGS. 23A-C are cross-sectional views depicting additional exemplary embodiments of stabilization device 105 being used to in an exemplary method of stabilizing treatment system 100. Here, stabilization member 105 is configured as an elongate member including an outer tubular sheath 501 having an inner lumen 504 configured to slidably receive inner elongate pull member 505. Outer tubular sheath 501 and inner pull member 505 are preferably semi-rigid, having enough rigidity to stabilize treatment system 100 while at the same time having enough flexibility to allow movement and manipulation within the patient's vasculature and heart 200. In these embodiments, stabilization device 105 is preferably configured to be routed from right atrium 205 through PFO tunnel 215 into left atrium 212, where grasping device 502 can be used to cover a portion of septum primum 214 and anchor stabilization device 105 thereto.

The nature of the tissue forcing septum primum 214 can be irregular, for instance including overlapping folds, variations in tissue thickness and variations in distensibility, each of which can cause septum primum 214 to move, or tent, when needle member 405 is advanced through. The inclusion of grasping device 502 can also provide the additional advantage of holding septum primum 214 in place and reducing the risk of tenting.

Grasping device 502 preferably includes a flexible grasping element 506 coupled with inner pull member 505. Here, grasping element 506 is configured as a rectangular element. Outer tubular sheath 501 preferably includes lumen 507 having open distal end 508, from which grasping element 506 can be deployed. Lumen 507 can be configured with contoured sidewalls to facilitate deployment of grasping element 506. To deploy grasping element 506, inner member 505 can be pulled in a proximal direction with respect to outer sheath 501, causing grasping element 506 to advance through lumen 507 and out of distal end 508. Grasping element 506 can optionally include an atraumatic end 512, which in this embodiment is a radio-opaque element, which may be gold or platinum. In this embodiment, grasping element 506 is configured as a deformable, pre-shaped element having three main configurations.

FIG. 23A depicts grasping element 506 in a first configuration housed within lumen 507. This configuration is preferably used while treatment system 100 is moved through the patient's vasculature and as well as when stabilization device 105 traverses PFO tunnel 215, as depicted here. FIG. 23B depicts grasping element 506 in a second configuration partially deployed from within lumen 507. Once stabilization device 105 is advanced through PFO tunnel 215 and out of PFO exit 218, grasping element 506 is preferably deployed to this configuration by pulling inner member 505 proximally with respect to outer sheath 501. In this configuration, grasping element 506 can be used to catch the edge of septum primum 214 as stabilization device 105 is pulled slightly back in proximal direction 509. FIG. 23C depicts grasping element 506 in a third, fully deployed configuration, after inner member 505 has been pulled back further. Grasping element 506 can optionally include a recess configured to engage an abutment on outer sheath 501 in this configuration, which is preferably used to more hilly grasp or engage septum primum 214 to anchor stabilization device 105 thereto.

Once the delivery procedure is complete, inner member 505 can be advanced distally with respect to outer sheath 501 to draw grasping element 506 back within lumen 507. Any component of treatment system 100 adequately coupled with stabilization device 105 is thereby also anchored to septum primum 214. One of skill in the art will readily recognize that this and similar embodiments of stabilization device 105 can be used to engage any tissue flap or edge desired, not solely septum primum 214.

Figure 24A:
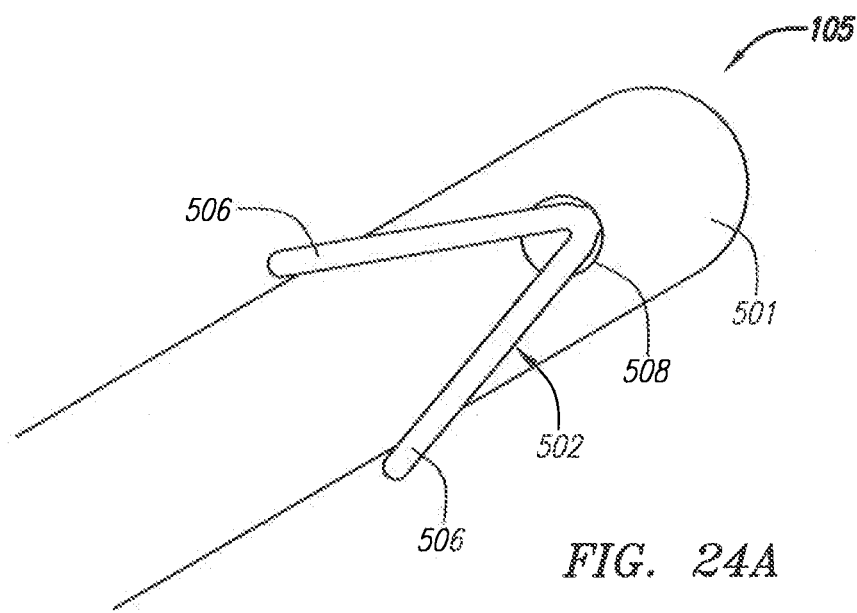
FIGS. 24A-B are perspective views depicting additional exemplary embodiments of a stabilization device.
Figure 24B:
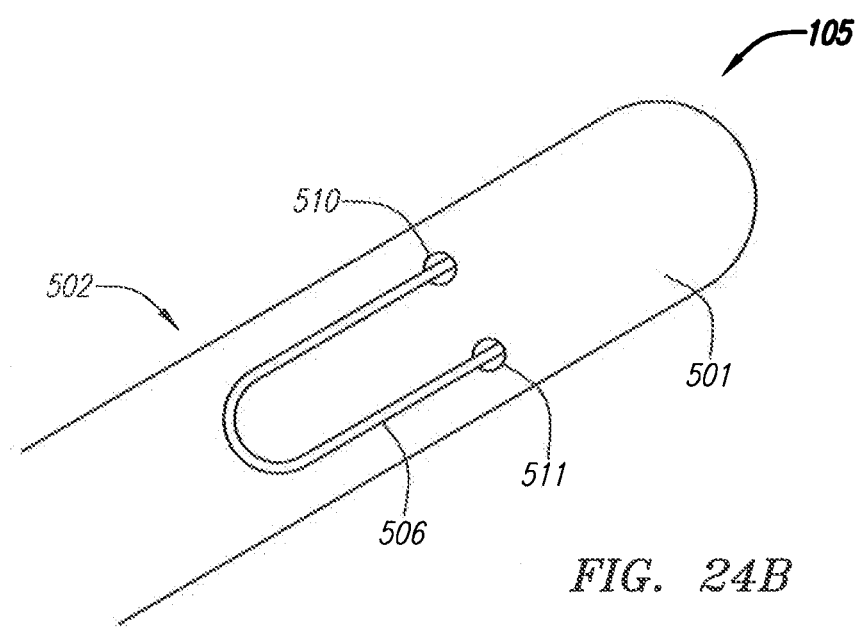

Grasping device 502 can be configured in any manner desired in accordance with the needs of the application. FIGS. 24A-B are perspective views depicting additional exemplary embodiments of stabilization device 105 with grasping device 502. In FIG. 24A, grasping device 502 includes multiple grasping elements 506 for grasping over a wider area. In FIG. 24B, grasping device 502 includes a wire-like grasping element 506. Here, grasping element 506 is looped into lumen 507 (not shown) via apertures 510 and 511, which communicate with lumen 507.

Figure 25A:
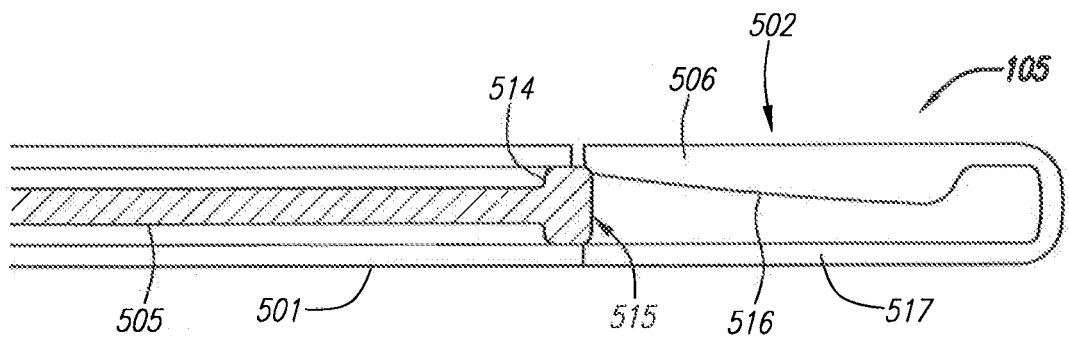
FIGS. 25A-D are cross-sectional views depicting additional exemplary embodiments of a stabilization device.
Figure 25B:
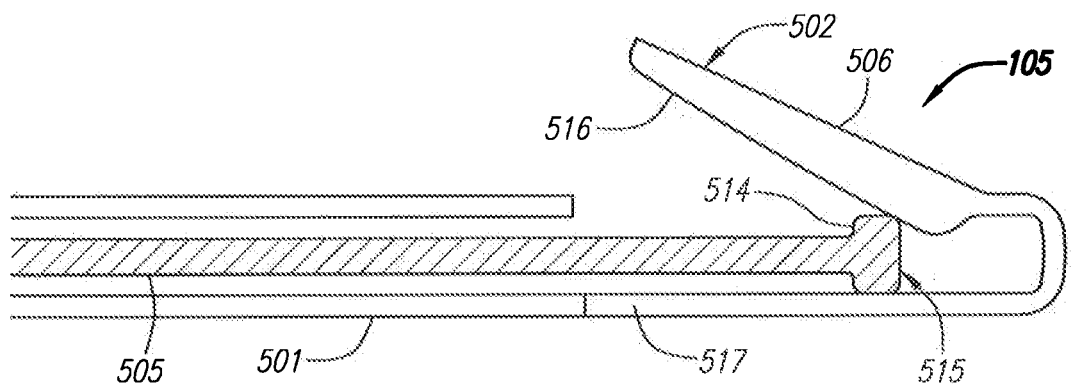
Figure 25C:
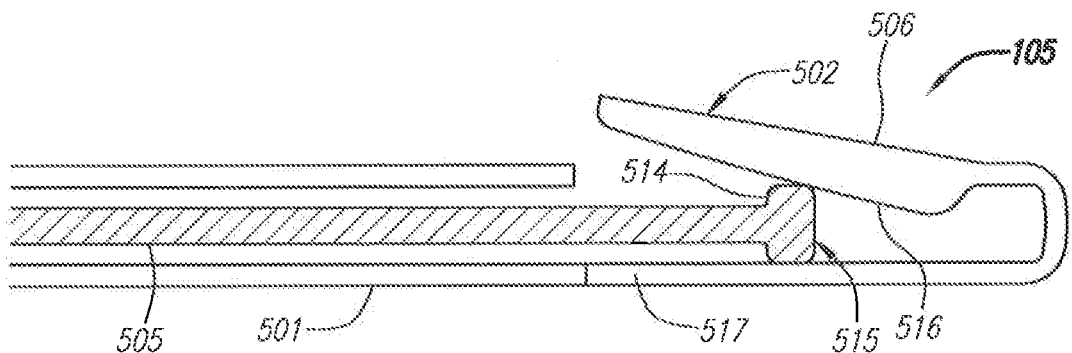
Figure 25D:
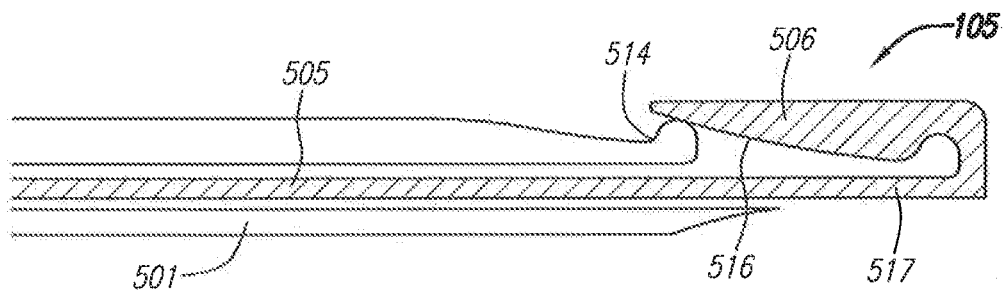

FIGS. 25A-D are cross-sectional views depicting additional exemplary embodiments of stabilization device 105. Here, grasping element 506 has a flap-like shape with tapered inner surface 516 and is located on distal end member 517 of outer sheath 501. Inner member 505 includes an abutment 514 on distal end portion 515 and is configured to push against and apply a force to grasping element 506. FIG. 25A depicts grasping element 506 in the first, housed configuration. To deploy grasping element 506 to the second configuration for catching septum primum 214, inner member 505 is advanced distally with respect to outer sheath 501 as depicted in FIG. 25B. Because of tapered inner surface 516, the more inner member 505 is advanced distally, the more outwards deflection of element 506 will occur. To more fully grasp septum primum 214, inner member 505 (and body member 101, if necessary) is retracted proximally by the desired amount, as depicted in FIG. 25C. Manufacture of this embodiment can be made relatively simple. For instance, distal end member 517 and grasping element 506 can be formed by laser or EDM cutting a NITINOL tube. In FIG. 25D, distal end member 517 is located on distal end of inner member 505 and abutment 514 is located on sheath 501.

Figure 26A:
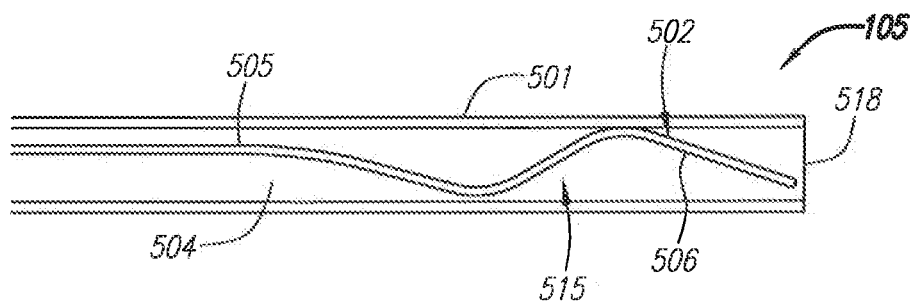
FIGS. 26A-C are cross-sectional views depicting additional exemplary embodiments of a stabilization device.
Figure 26B:
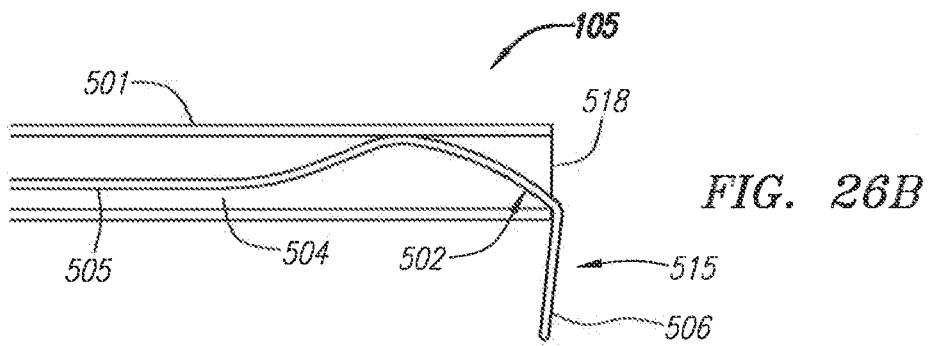
Figure 26C:
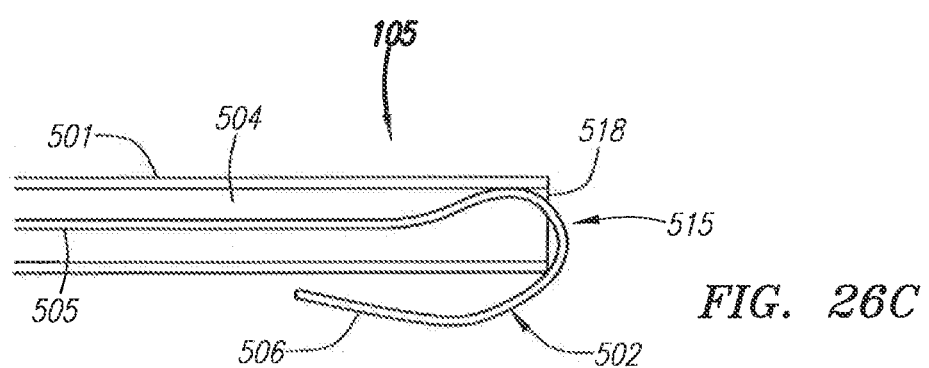

FIGS. 26A-C are cross-sectional views of additional exemplary embodiments of stabilization device 105. Here, outer sheath 501 preferably includes an open distal end 518, from which grasping device 502 can be deployed. Grasping element 506 is preferably located on distal end portion 515 of inner member 505 and can be formed of a deformable elastic material such as stainless steel, NITINOL, shape memory polymers and the like. Grasping element 506 is preferably configured to be slidable within inner lumen 504 and is preferably pre-shaped, such as by heat-treating NITINOL, so that grasping element 506 can assume a desired shape when advanced from inner lumen 504. In FIG. 26A, grasping element 506 is depicted in the first, housed configuration within inner lumen 504. In FIG. 26B, inner member 505 has been advanced distally to deploy grasping element 506 in the second configuration for catching septum primum 214. In FIG. 26C, inner member 505 has been advanced further distally to place grasping element 506 in the third configuration for grasping septum primum 214. Embodiments of stabilization device 105 where grasping device 502 can be deployed by pushing grasping device 502 out from within inner lumen 504, such as that described with respect to FIGS. 26A-C, will be referred to herein as "push out" embodiments.

Figure 27A:
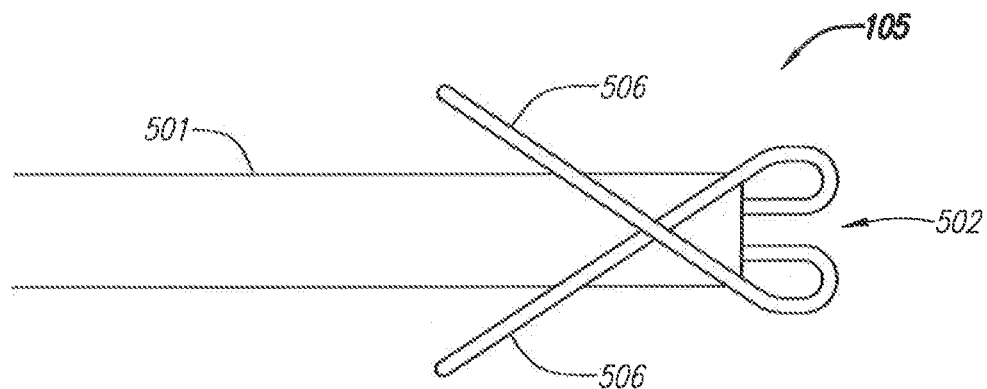
FIG. 27A is a perspective view depicting an additional exemplary embodiment of a stabilization device.
Figure 27B:
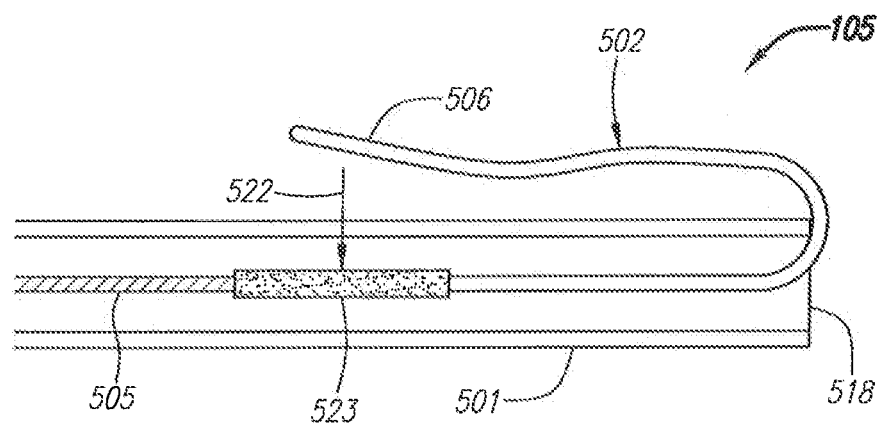
FIG. 27B is a cross-sectional view depicting another exemplary embodiment of a stabilization device.

FIG. 27A is a perspective view depicting an additional exemplary embodiment of stabilization device 105 having a "push-out" grasping device 502. Here, grasping device 502 is shown in the fully deployed third configuration having two grasping elements 506. It should be noted that grasping device 502 can include any number of grasping elements 506. Here, each grasping element 506 overlaps so as to provide additional grasping force at location 419 where needle member 405 insertion occurs. FIG. 27B is a cross-sectional view depicting another exemplary embodiment where grasping element 506 is configured to attract to a magnetic force 522 provided by magnet 523 coupled with inner member 505. Once deployed, the magnetic force is preferably great enough to penetrate outer sheath 501 and septum primum 214 and attract elements 506 to provide additional grasping force. Of course, magnet 523 can be placed in any desired location, for instance, on outer sheath 501 at distal end 518 or on grasping element 506, in which case inner member 505 could be configured to attract to the magnetic force, or any combination thereof.

It should be noted that, in order to provide additional surface friction, additional abutments can be included on grasping element 506 and/or the surface of grasping element 506 can be etched or coated or otherwise textured.

As discussed with respect to FIG. 1, treatment system 100 can include centering device 106 to facilitate proper placement of implant 103. Centering device 106 can be configured to align delivery device 104 in the desired location with respect to the center of PFO tunnel 215. Although the term "centering" is used, it should be understood that centering device 106 can be configured to align delivery device 104 in any location, not necessarily the center of PFO tunnel 215.

Figure 28A:
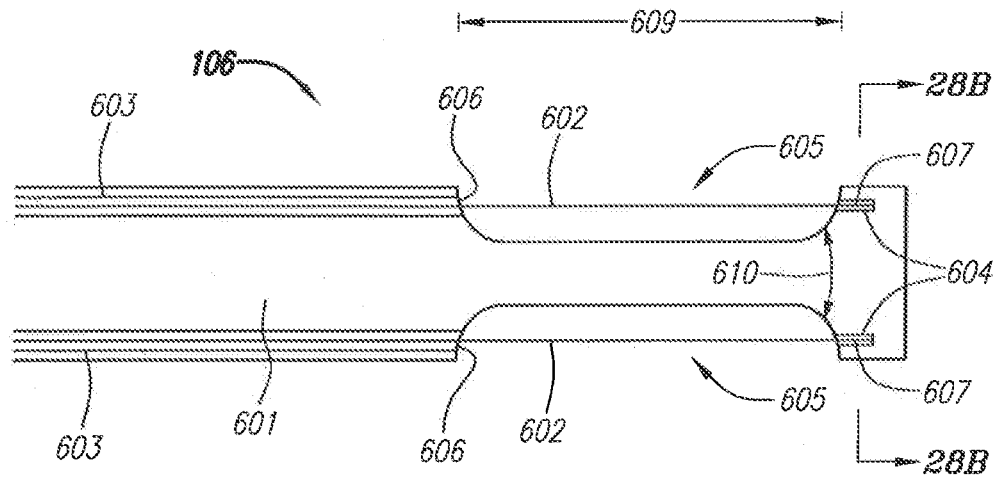
FIGS. 28A-C are cross-sectional views depicting additional exemplary embodiments of a centering device.
Figure 28B:
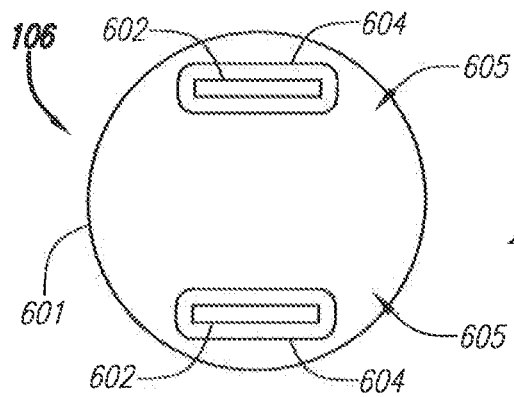
Figure 28C:
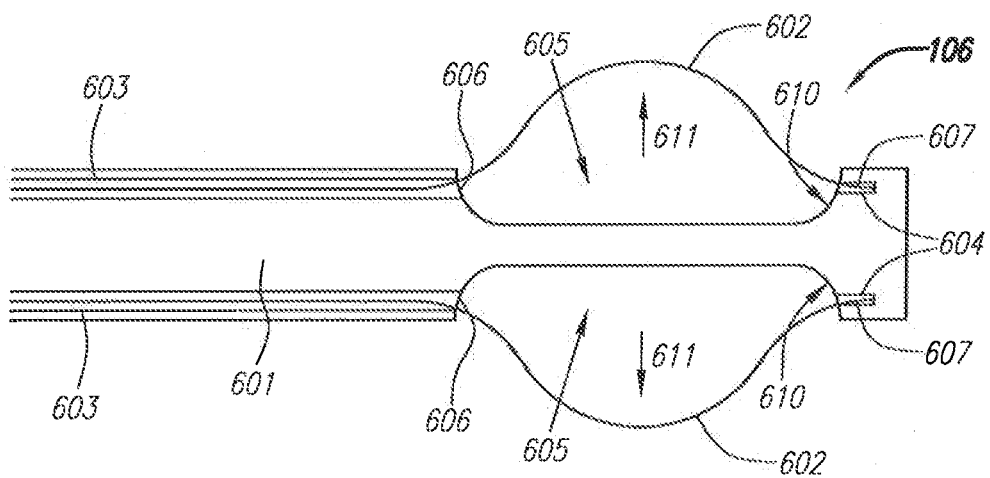

FIGS. 28A-C are cross-sectional views depicting additional exemplary embodiments of centering device 106. In this embodiment, centering device 106 includes an elongate centering support member 601 having two elongate flexible positioning members 602, referred to herein as centering arms 602, located on opposite sides of and extending along the length of support member 601. Support member 601 can include two lumens 603, each configured to slidably receive a centering arm 602. Each lumen 603 preferably has an open distal end 606 which opens to an open or recessed portion 605 of support member 601. Each centering arm 602 preferably extends through this recessed portion 605 and into seat 604 preferably configured to receive distal end 607 of each centering arm 602. Seat 604 is preferably located in recessed portion 605 in a position opposite to lumen 603.

FIG. 28A depicts centering arms 602 at rest within recessed portion 605 along the sides of support member 601. The length of recessed portion 605 is indicated as length 609. FIG. 28B is a cross-sectional view of centering device 106 taken along tine 28B-28B of FIG. 28A. As depicted here, centering arms 602 are preferably configured as rectangular wire bands, although any configuration can be used as desired. Advancement of centering arms 602 in a distal direction causes distal end 607 to contact seat 604 and forces centering arms 602 to extend outwards from recessed portion 605 as depicted in FIG. 28C. Configuration of centering arms 602 as bands helps ensure that arms 602 extend directly away from support member 601 in direction 611.

Figure 28D:
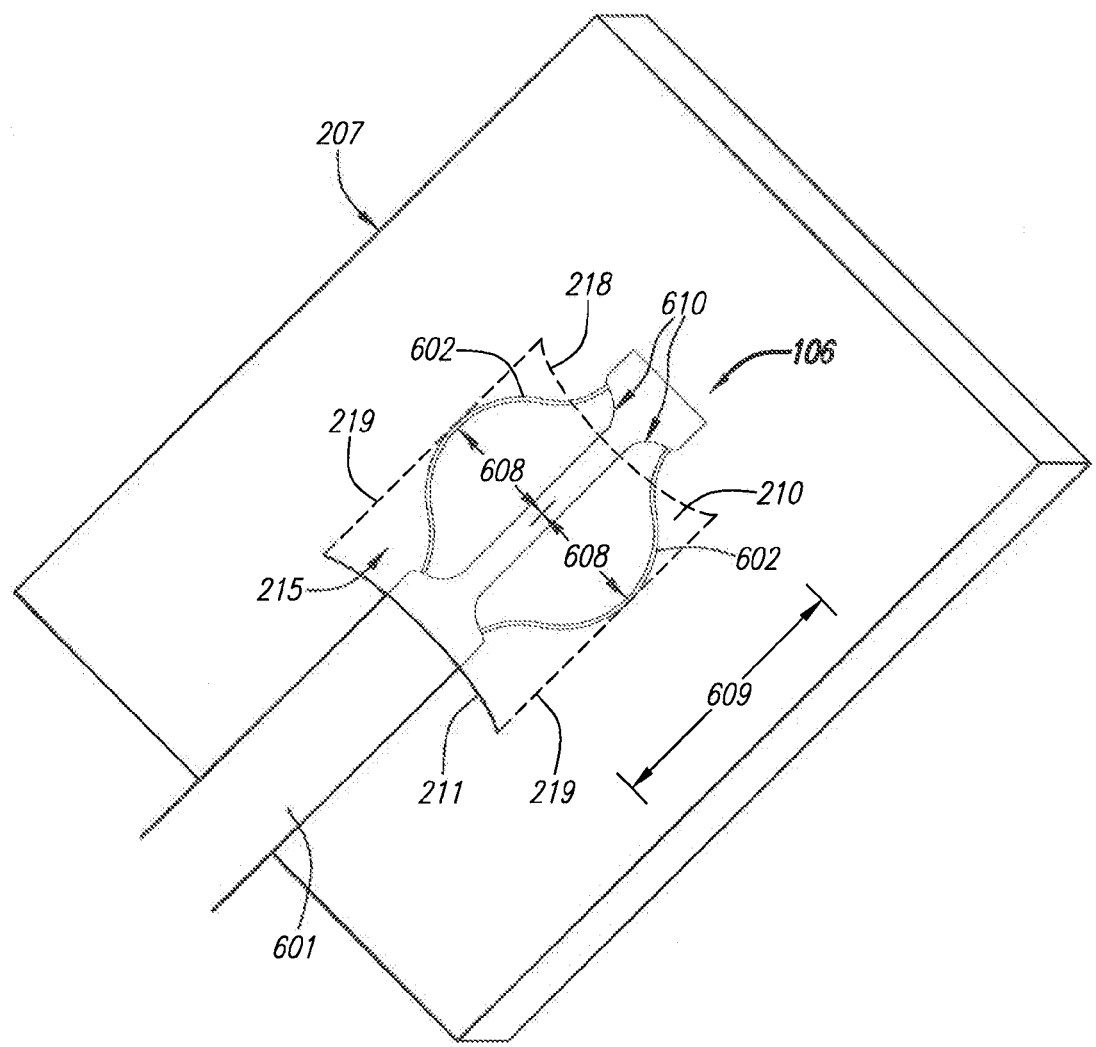
FIG. 28D is a schematic view depicting another exemplary embodiment of a centering device within a septal wall.

When centering device 106 is placed within PFO tunnel 215, centering arms 602 can be extended until coming into contact with sidewalls 219, as depicted in FIG. 28D, which is a perspective view of centering device 106 within PFO tunnel 215. Here, sidewalls 219 and PFO exit 218 are shown as dashed lines to indicate their presence underneath septum secundum 210. When centering arms 602 are each advanced the same amount until contact with both sidewalk 219 is made, the extension distance 608 of each arm 602 will likewise be the same amount and support member 601 will be forced into a centered position within PFO tunnel 215.

In this manner, centering device 106 can be centered within PFO tunnel 215 and can be used as a reference point for delivering implant 103. Preferably, centering device 106 is coupled with delivery device 104, so that centering of centering device 106 will also cause centering of delivery device 104. Preferably, once implant 103 is delivered, centering arms 602 are retracted proximally into lumens 603 and centering device can then be retracted through PFO tunnel 215. Surface 610 of recessed portion 605 is preferably curved, or tapered, to reduce the risk that support member 601 will catch or become hung up on any tissue in or around PFO tunnel 215.

Here, the extended portions of centering arms 602 are shown as being located entirely within PFO tunnel 215. One of skill in the art will readily recognize that variation of length 609 of recessed portion 605 will cause the extended portion of centering arms 602 to vary accordingly.

Support member 601 and centering arm 602 can each be composed of any desired material in accordance with the needs of the application. Preferably, support member 601 is composed of a flexible polymer, such as Polyimides, polyamides, polyproylene and the like. Preferably, centering arms 602 are composed of a flexible polymer or metal, such as NITINOL, stainless steel and the like.

Figure 29A:
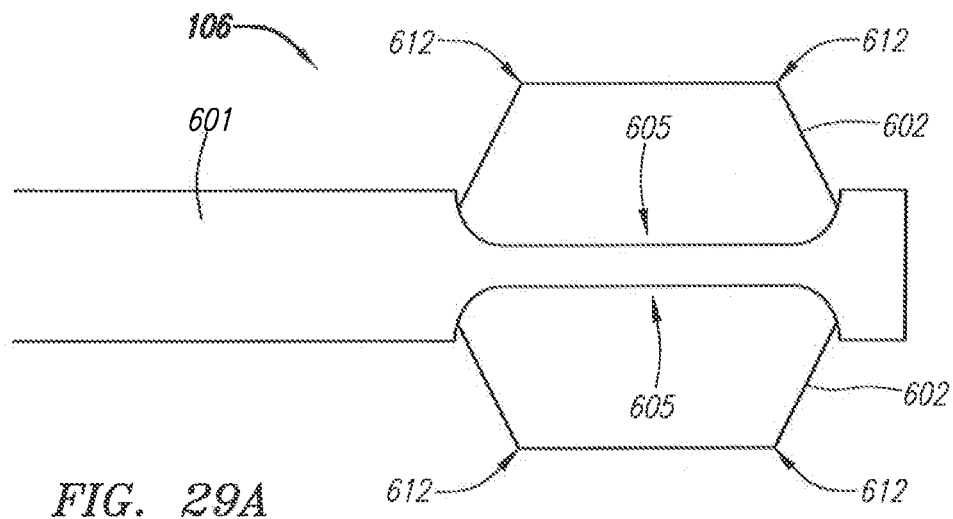
FIGS. 29A-C, 30 and 31 are schematic views depicting additional exemplary embodiments of a centering device.
Figure 29B:
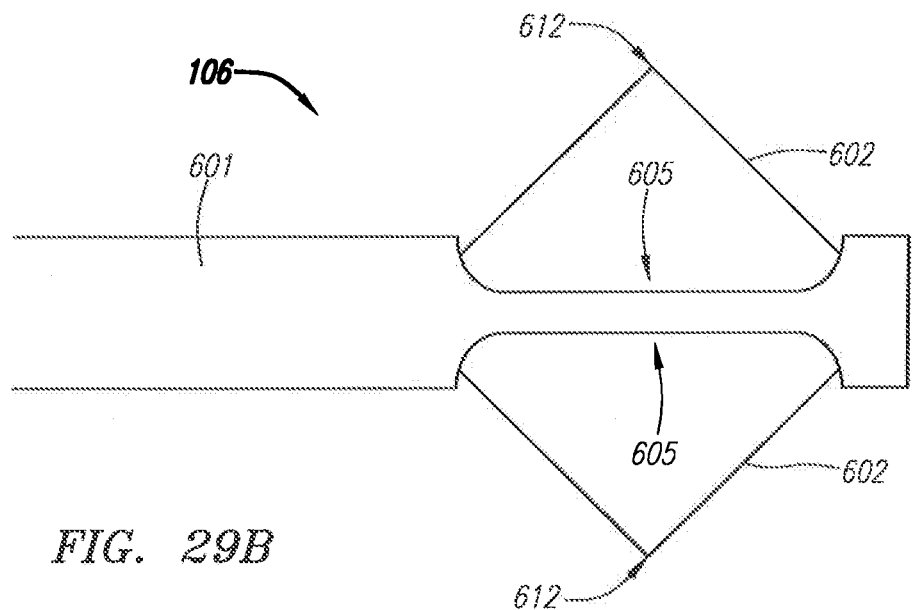

In the embodiment described with respect to FIGS. 28A-D, centering arms 602 have a curved or arcuate shape when extended from support member 601. As the FIGS. 29A-C will show, centering arms 602 can be configured to have any desired shape when extended. FIGS. 29A-B are schematic views depicting additional exemplary embodiments of centering device 106 with centering arms 602 extended in a three-sided and two-sided shapes, respectively. Preferably, portions 612 of centering arms 602 are made thinner than the surrounding portions, so that centering arms 602 have a tendency to flex first in portions 612, allowing these polygonal shapes to be achieved.

Also, arms 602 can be pre-shaped to be biased to assume a desired shape when allowed to expand from recessed portion 605. For instance, in one exemplary embodiment, arms 602 are composed of NITINOL and are heat-treated for pre-shaping. One of skill in the art will readily recognize, in light of this disclosure, that variation of the thickness of arms 602 and pre-shaping can allow an almost limitless number of shapes to be achieved, having curved portions, straight portions and any combination thereof which can be symmetric or asymmetric.

Figure 29C:
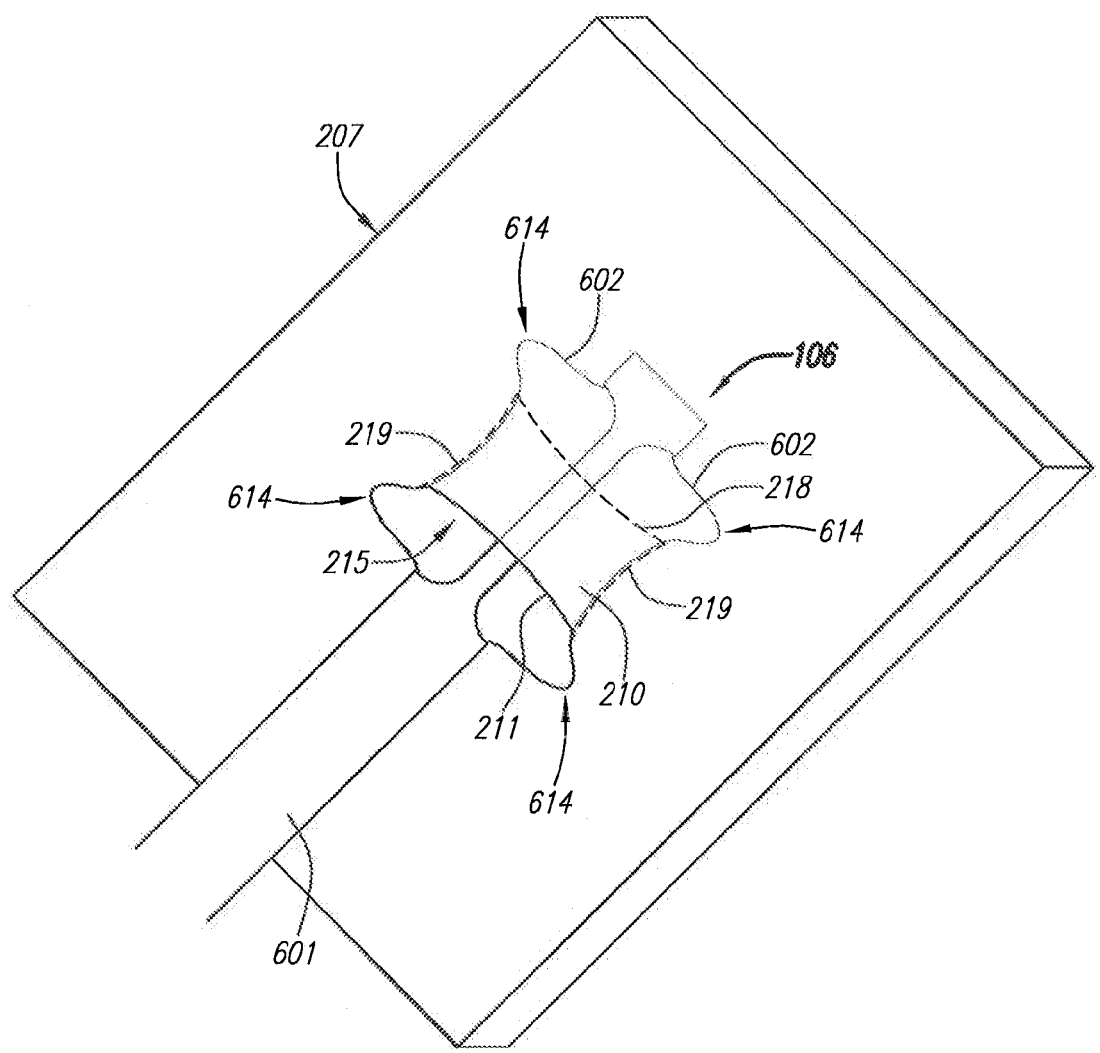

As mentioned above, in some cases, sidewalls 219 of PFO tunnel 215 are not equidistant along the length of PFO tunnel 215, causing PFO tunnel 215 to diverge or converge from PFO entrance 217 to PFO exit 218. Divergence or convergence of PFO tunnel. 215 can cause centering device 106 to slip out from PFO tunnel 215 when arms 602 are extended. FIG. 29C is a schematic view depicting another exemplary embodiment of centering device 106 where each centering arm 602 is configured to extend with two outcroppings 614. These outcroppings 614 can be placed outside PFO tunnel 215 to prevent centering device 106 from slipping out of PFO tunnel 215. Outcroppings 614 can be formed by making that portion of centering arm 602 relatively thicker than the surrounding portions, making outcropping 614 less likely to flex. A desired radius of curvature in centering arms 602 can be implemented by pre-shaping, or by gradually varying the thickness and/or width of centering arms 602, where a relatively thinner portion will correspond to a relatively larger rate of curvature.

Figure 30:
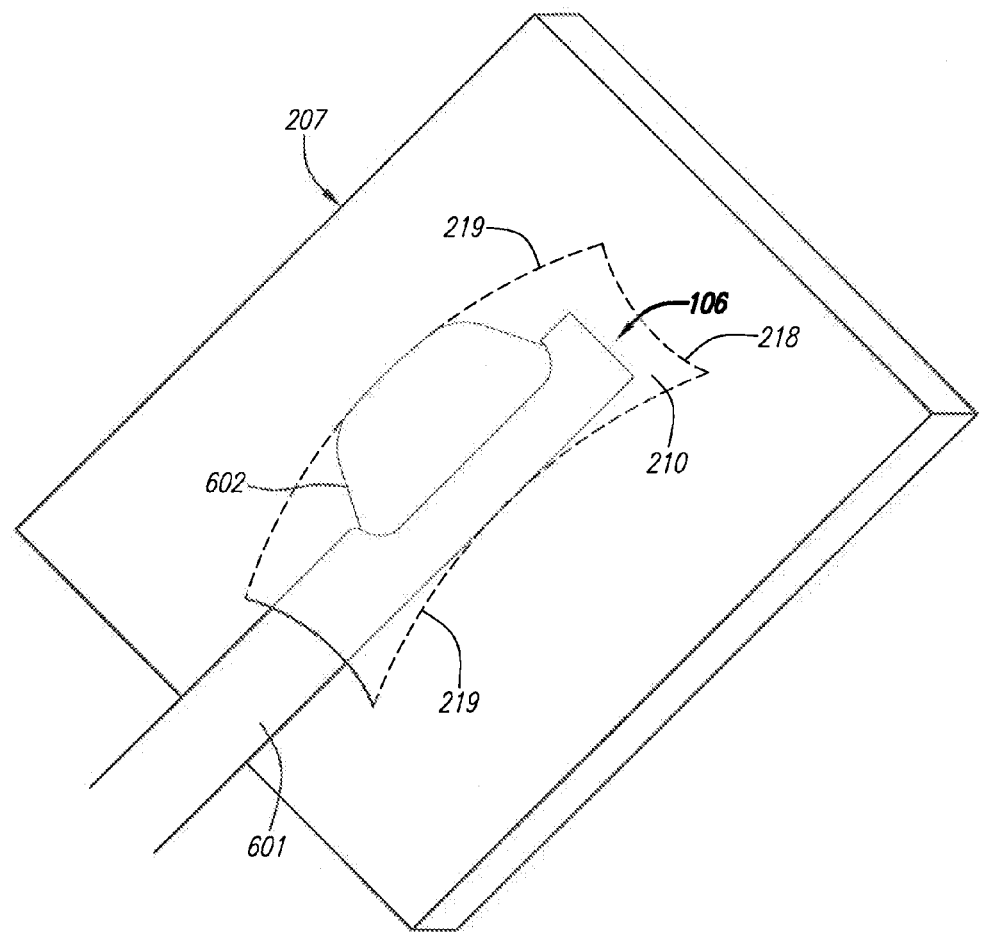

It should be noted that centering device 106 can include any number of one or more arms 602 for centering/positioning purposes. FIG. 30 is a schematic view depicting another exemplary embodiment of centering device 106 having one centering arm 602 extended within PFO tunnel 215. In this embodiment, PFO tunnel 215 is curved to one side and centering arm 602 is positioned on the opposite side. Centering arm 602 can then be extended a predetermined distance to position centering device 106 in the desired location.

In another exemplary embodiment, centering device 106 includes multiple arms 602 configured for use independently of each other to allow the user to have increased control over the position of centering device 106 within PFO tunnel 215. For instance, the user can adjust two opposing arms 602 to center device 106 between sidewalls 219 within tunnel 215, and then adjust a third arm 602 to position device 106 as desired relative to septum secundum 210 and septum primum 214. In another case, the user can use three or more arms 602 for centering based on the tunnel type or anatomy.

Figure 31:
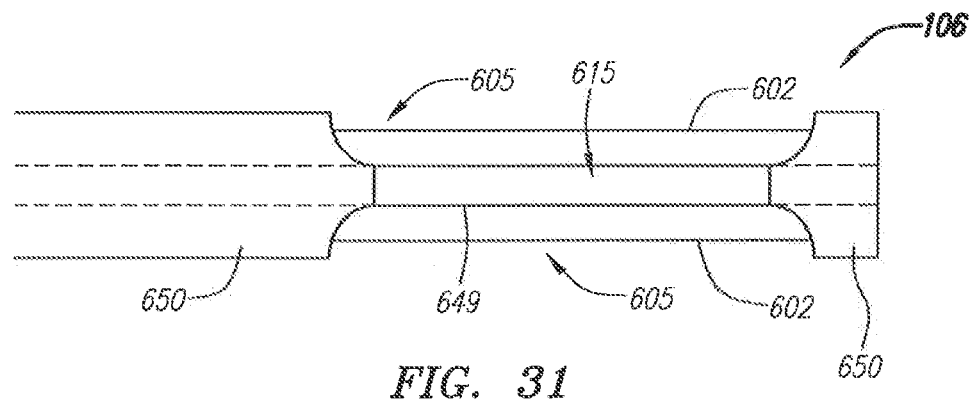

In some embodiments, it can be desirable to keep centering device 106 within PFO tunnel 215 while needle member 405 is advanced through septal wall 207. To reduce the risk that needle member 405 will contact centering device 106 during this procedure, support member 601 can be configured to deflect needle member 405. FIG. 31 is a schematic view depicting an exemplary embodiment of centering device 106 where support member 601 is a rigid cylindrical member 649 having a smooth, or polished, surface 615 between lumen 603 and seat 604 (as shown in FIG. 28A), which are formed in rigid extrusions 650 which are preferable metal and located on member 649. Here, if sharpened distal end 415 of needle member 405 comes into contact with support member 601, it is more likely to be deflected from rigid cylindrical member 649.

Figure 32A:
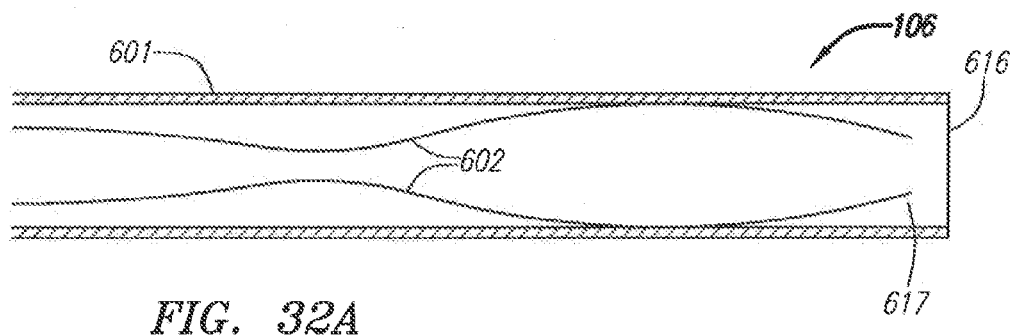
FIGS. 32A-B are cross-sectional views depicting additional exemplary embodiments of a centering device.
Figure 32B:
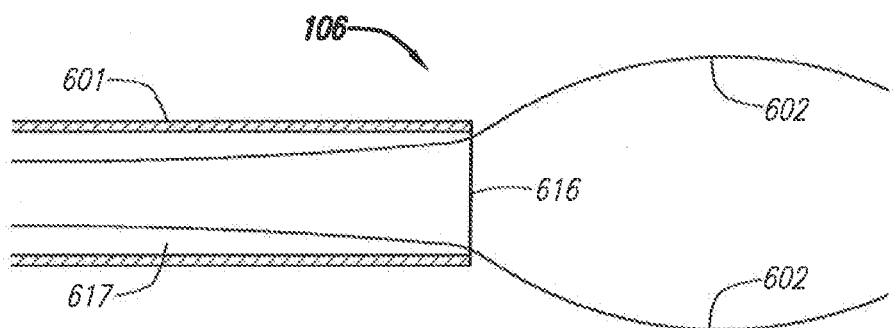

FIGS. 32A-B are cross-sectional views depicting additional exemplary embodiments of centering device 106 where support member 601 includes an open distal end 616 from which one or more pre-shaped centering arms 602 can be extended. Centering arms 602 are preferably pre-shaped to the extended position allowing elimination of seat 604 and recessed portion 605. Centering arms 602 are preferably deformable from a first configuration to allow housing within inner lumen 617 of support member 601 as depicted in FIG. 32A. In FIG. 32B, centering arms 602 are shown deployed from inner lumen 617 in their extended second configuration. Although in FIGS. 32A-B, centering arms 602 are shown as separate elements, the proximal end of the pre-shaped portion of each arm 602 can be coupled together on a common elongate shaft.

Figure 32C:
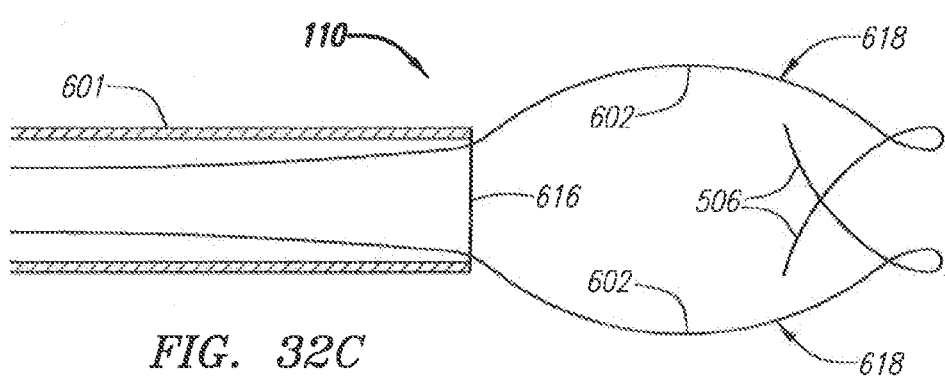
FIG. 32C is a cross-sectional view depicting another exemplary embodiment of a centering device with an exemplary embodiment of a stabilization device.

It should be noted that the functionality of the various embodiments described herein can be combined and integrated together to reduce the number of components in treatment system 100, simplify the design of treatment system 100 and so forth. For instance, FIG. 32C depicts an exemplary embodiment of treatment system 100 where the embodiments described with respect to FIGS. 27A and 32A-B have been integrated together to form device 110. Here, centering arms 602, similar to that depicted in FIGS. 32A-B each include grasping element 506 of stabilization device 105, similar to that depicted in FIG. 27A, located distal to the centering portion 618. Here, centering device 106 is used for centering and stabilization, allowing the elimination of a separate stabilization device 105 from system 100.

For stabilization and centering, support member 601 is preferably advanced through PFO exit 218. Once in left atrium 212, centering arms 602 can be advanced distally to deploy grasping elements 506 from the first, housed configuration, to the second and third configurations for catching and grasping septum primum 214. Once septum primum 214 is grasped, support member 601 can be retracted proximally with respect to centering arms 602 in order to deploy centering portions 618 of each arm 602. The centering portions 618 can then expand outwards and center device 106, thereby preferably also centering body member 101 and delivery device 104, while at the same time maintaining a grasp of septum primum 214.

Figure 32D:
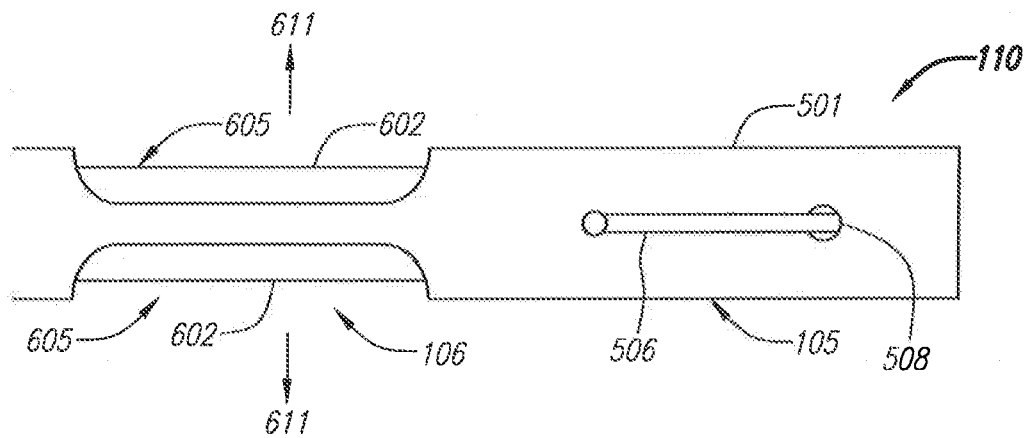
FIG. 32D is a schematic view depicting another exemplary embodiment of a centering device with an exemplary embodiment of a stabilization device.

FIG. 32D is a schematic view depicting another exemplary embodiment of treatment system 100 where centering device 106 and stabilization device 105 have been integrated together. Here, stabilization member 501 includes two lumens 603 and seats 604 (not shown), and recessed portions 605 for use with centering arms 602. After stabilization with device 105, centering arms 602 can be extended in directions 611 to center or otherwise place combined device 110 in the desired position.

Figure 33A:
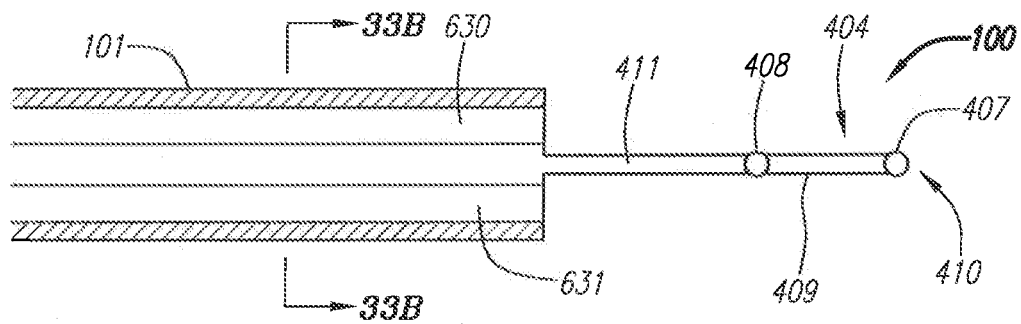
FIG. 33A is a longitudinal cross-sectional view of an exemplary embodiment of a treatment system.
Figure 33B:
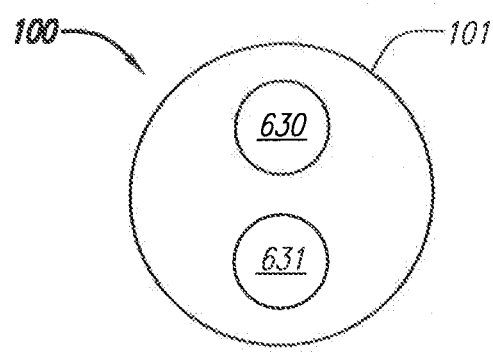
FIG. 33B is a radial cross-sectional view of another exemplary embodiment of a treatment system taken along line 33B-33B of FIG. 33A.

As discussed with respect to FIG. 1, delivery device 104, stabilization device 105 and centering device 106 are each preferably used in conjunction with body member 101. Body member 101 can be configured in any manner desired in accordance with the needs of the application. FIGS. 33A-B are cross-sectional views depicting another exemplary embodiment of treatment system 100 where body member 101 includes two lumens 630 and 631. FIG. 33A is a longitudinal cross-sectional view and FIG. 33B is a radial cross-sectional view taken along line 33B-33B of FIG. 33A. Preferably, lumen 630 is configured to slidably receive delivery device 104, while lumen 631 is configured to slidably receive either stabilization device 105 or an optional guidewire to facilitate routing body member 101 through the patient's vasculature. The guidewire can be placed in lumen 631 until body member 101 is in the desired position within the patient, at which time the guidewire can be removed and stabilization device 105 can be inserted. Also, centering device 106 is preferably integrated with stabilization device 105, such as in the embodiment described with respect to FIG. 32D, in order to provide treatment system with both stabilization and centering capability. In order to prevent rotation of elongate body member 101 around stabilization device 105 during delivery, stabilization device is preferably fixably coupled with either body member 101 or delivery device 104.

FIGS. 34A-C are cross-sectional views depicting another exemplary embodiment of treatment system 100 where body member 101 includes four lumens 630-633 as well as centering arms 602. Here, FIG. 34A is a first longitudinal cross-sectional view. FIG. 34B is a radial cross-sectional view taken along line 34B-34B of FIG. 34A and FIG. 34C is a second longitudinal cross-sectional view taken along line 34C-34C of FIG. 34A. Preferably, lumen 630 is configured to slidably receive delivery device 104, while lumen 631 is configured for any purpose, including reception of stabilization device 105, a guidewire, dye infusion and the like. FIG. 34B depicts centering arms 602 within lumens 632633 and FIG. 34C depicts centering arms 602 located within lumens 632-633, recessed portions 605 and seats 604. Here, recessed portions 605 and seats 604 are located distal to grasping device 404 on elongate support section 411. The distal portion of support section 411 can be placed within PFO tunnel 215 where centering arms 602 can be deflected for centering prior to deployment of implant 103 in left atrium.

Figure 35A:
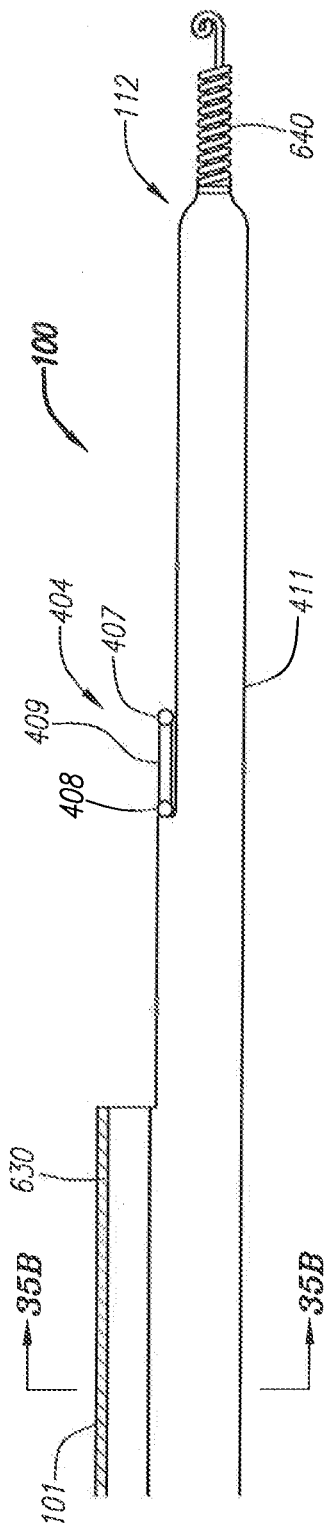
FIG. 35A is a longitudinal cross-sectional view of an exemplary embodiment of a treatment system.
Figure 35B:
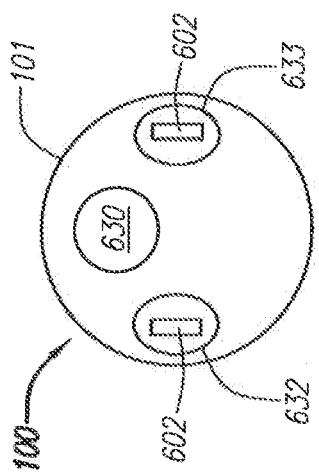
FIG. 35B is a radial cross-sectional view of another exemplary embodiment of a treatment system taken along line 35B-35B of FIG. 35A.

FIGS. 35A-B are cross-sectional views depicting another exemplary embodiment of treatment system 100 where body member 101 includes three lumens 630, 632 and 633 as well as centering arms 602. Here, FIG. 35A is a longitudinal cross-sectional view and FIG. 35B is a radial cross-sectional view taken along line 35B-35B of FIG. 35A. In this embodiment, distal end 112 of body member 101 includes an atraumatic tip 640, which in this embodiment is a floppy tip. Here, with the aid of atraumatic tip 640, body member 101 is configured to be advanceable within the patient's vasculature without the aid of a guidewire. Accordingly, no additional lumen 631 is included for use with a guidewire. Also in this embodiment, stabilization device 105 has been optionally omitted, allowing body member 101 to achieve a relatively smaller radial cross-section size. In another exemplary embodiment, atraumatic tip 640 is omitted and body member 101 is configured to be slidably advanced through a tubular guide catheter placed within the patient's vasculature.

Figure 36A:
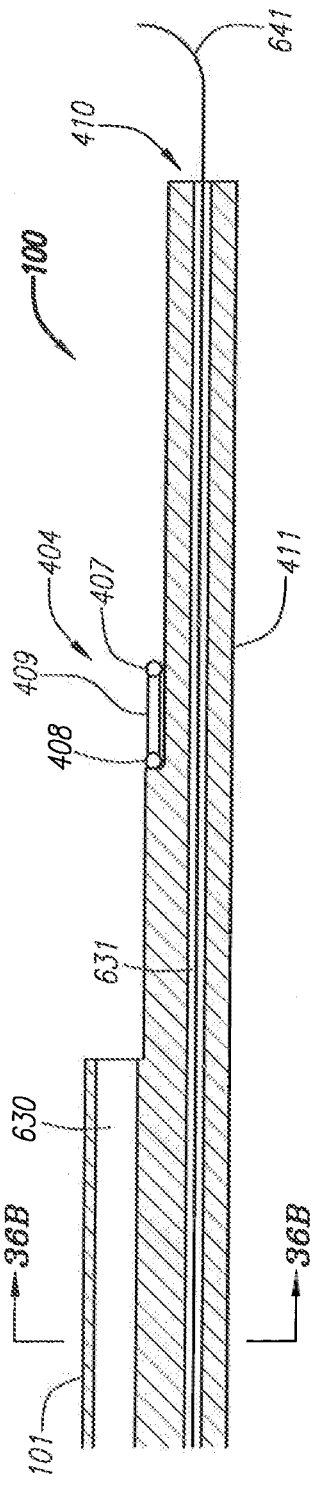
FIG. 36A is a longitudinal cross-sectional view of an exemplary embodiment of a treatment system.
Figure 36B:
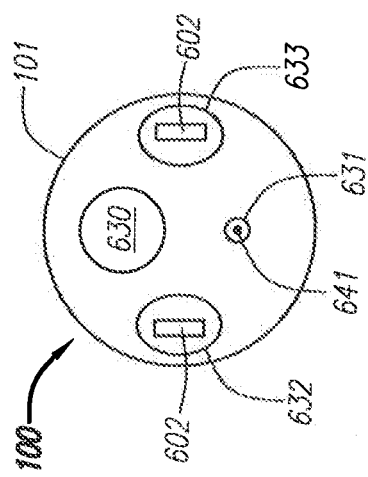
FIG. 36B is a radial cross-sectional view of another exemplary embodiment of a treatment system taken along line 36B-36B of FIG. 36A.

FIGS. 36A-B are cross-sectional views depicting another exemplary embodiment of treatment system 100 where body member 101 includes four lumens 630-633 as well as centering arms 602. Here, FIG. 36A is a longitudinal cross-sectional view and FIG. 36B is a radial cross-sectional view taken along line 36B-36B of FIG. 36A. This embodiment is similar to the embodiment described with respect to FIGS. 34A-C except here, lumen 631 is configured for use with guidewire 641 only, which can be the same size as or relatively thinner than stabilization device 105, allowing the radial cross-section size of lumen 631 and body member 101 to be reduced.

FIGS. 37A-B are cross-sectional views depicting another exemplary embodiment of treatment system 100 where body member 101 includes four lumens 630-633 as well as centering arms 602. Here, FIG. 37A is a longitudinal cross-sectional view and FIG. 37B is a radial cross-sectional view taken along line 37B-37B of FIG. 37A. This embodiment is similar to the embodiment described with respect to FIGS. 35A-C except here, lumen 631 is configured to facilitate exchange of stabilization device 105 and guidewire 641. Proximal portion 642 of lumen 631 includes a divider 643 to separate lumen 631 into a first portion 644 for stabilization device 105 and a second portion 645 for guidewire 641. Distal portion 646 of lumen 631 is preferably tapered to minimize the radial cross-section size of lumen 631. Exchange between stabilization device 105 and guidewire 641 is facilitated because both can reside within proximal portion 642 at the same time, with the desired one of stabilization device 105 or guidewire 641 being advanced distally through open distal end 647 for use.

It should be noted that in each of the embodiments described with respect to FIGS. 33A-37B, functionality can be added or removed as desired, while still remaining within the scope of treatment system 100. For instance, treatment system 100 can be further configured for dye infusion, pressure sensing, imaging, drug delivery, ablation, the use of occlusive devices such as balloons and stents, facilitating the implantation of coronary sinus pacing or defibrillation leads, the use of a stylet and the like. These and other additional types of functionality can be added in any manner, including, but not limited to the addition of one or more lumens 102, or the use of the existing lumens 102, integration directly into body member 101, or the addition of one or more extra body members 101.

In addition, treatment system 100 can include multiple delivery devices 104 for delivery of multiple implants 103, multiple stabilization devices 105 for stabilization on multiple tissue surfaces, multiple centering devices 106 and multiple body members 101 as desired. If treatment system 100 is used to access septal wall 207 via inferior vena cava 202, the maximum radial cross-section size of body member 101 is preferably 13 French or less, although it should be noted that any size body member 101 can be used in accordance with the needs of the application. Body member 101 can be constructed from any material as desired, but is preferably constructed from a flexible polymer such as polyethylene, polypropylene, nylon and the like.

Furthermore, it should be noted that any component or component portion within treatment system 100 can be configured to facilitate any type of imaging, including, but not limited to, internal and external ultrasound imaging, optical imaging, magnetic resonance imaging (MRI), and flouroscopy. For instance, radio-opaque portions can be used to increase the visibility in flouroscopic applications while echolucent coatings can be used to increase visibility in ultrasound applications. As an example, in one exemplary embodiment OA delivery member 401 can be entirely radio-opaque, or can include portions that are radio-opaque, such as on distal tip 430 of FIG. 14A.

Also described herein are methods 700 and 800 of treating PFO tunnel 215, preferably by at least partially closing PFO tunnel 215. Methods 700 and 800 are preferably used with treatment system 100, but can be used with any medical system as desired. For ease of discussion, method 700 will be described with respect to treatment system 100 and method 800 will be described without reference to a particular treatment system, although it should be understood that methods 700 and 800 can be used with or without treatment system 100. Generally, the steps of methods 700 will vary, in part, on the actual configuration of implant 103, the number of implants 103 to be delivered, the location in which each implant 103 is to be delivered, the use of guidewire 641 or a guide catheter and the optional use of stabilization device 105 and/or centering device 106 or any combination thereof.

Figure 38A:
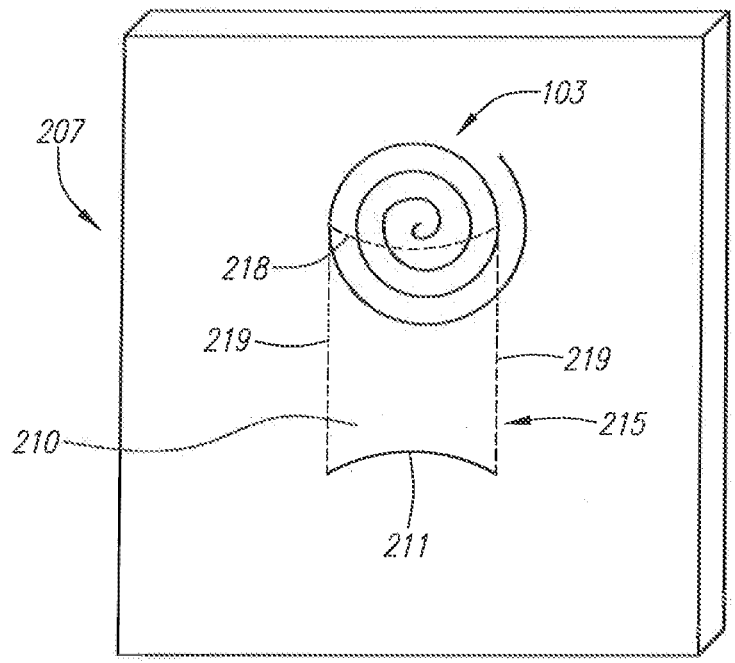
FIGS. 38A-E are cross-sectional views of a septal wall depicting exemplary embodiments of the implantable treatment device.
Figure 38B:
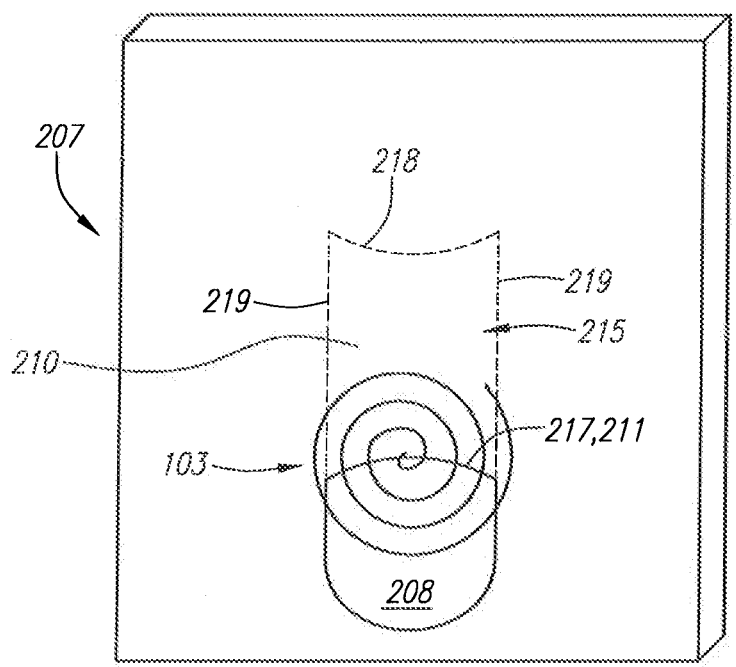
Figure 38C:
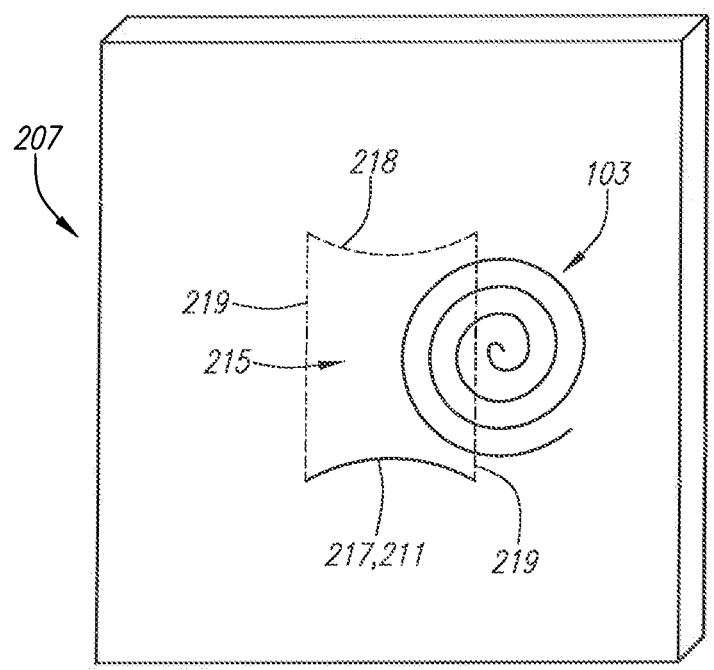

In FIG. 4E, implant 103 is delivered through both septum primum 214 and septum secundum 210. It should be noted, however, that implant 103 can be delivered in any location desired. FIGS. 38A-C are cross-sectional views of septal wall 207 depicting exemplary embodiments of implant 103 in just several of the many alternate locations that can be used. In FIG. 38A, implant 103 has been delivered through the upper portion of septum secundum 210 adjacent to PFO exit 218. In FIG. 388, implant 103 has been delivered through the lower portion of septum primum 214, adjacent to PFO entrance 217 and near (or in) fossa ovalis 208. In FIG. 38C, implant 103 has been delivered through septal wall 207 adjacent to sidewall 219, septum primum 214 and septum secundum 210.

Figure 38D:
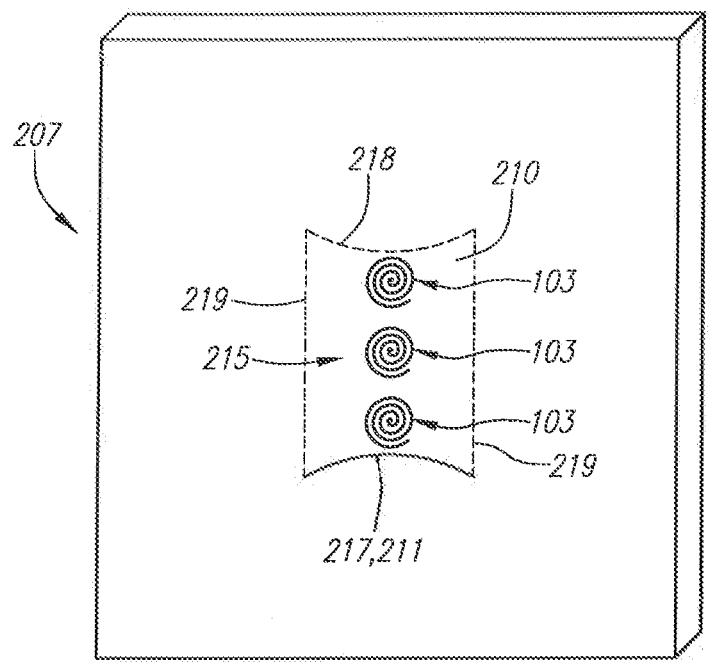
Figure 38E:
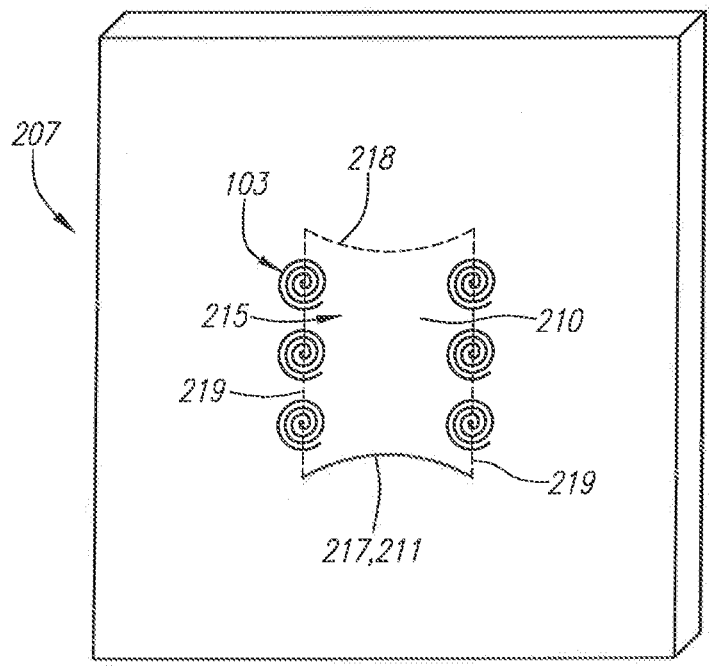

Also, as many implants 103 can be used in any arrangement as desired. FIGS. 38D-E are views of septal wall 207 depicting exemplary embodiments of multiple implants 103 in just several of the many alternate arrangements that can be used. In FIG. 38D, three implants 103 have been delivered through both septum primum 214 and septum secundum 210. In FIG. 38E, six implants 103 have been delivered through septal wall 207 adjacent to both sidewalls 219, septum primum 214 and septum secundum 210.

Although there are many different implementations and variations of method 700, for ease of discussion, method 700 will be described herein as using one implant 103, delivered through both septum primum 214 and septum secundum 210, using an exemplary embodiment of treatment system 100 similar to that described above with respect to FIGS. 33A-B, where body member 101 is configured for use with stabilization device 105 having centering device 106 integrated thereon.

Figure 39A:
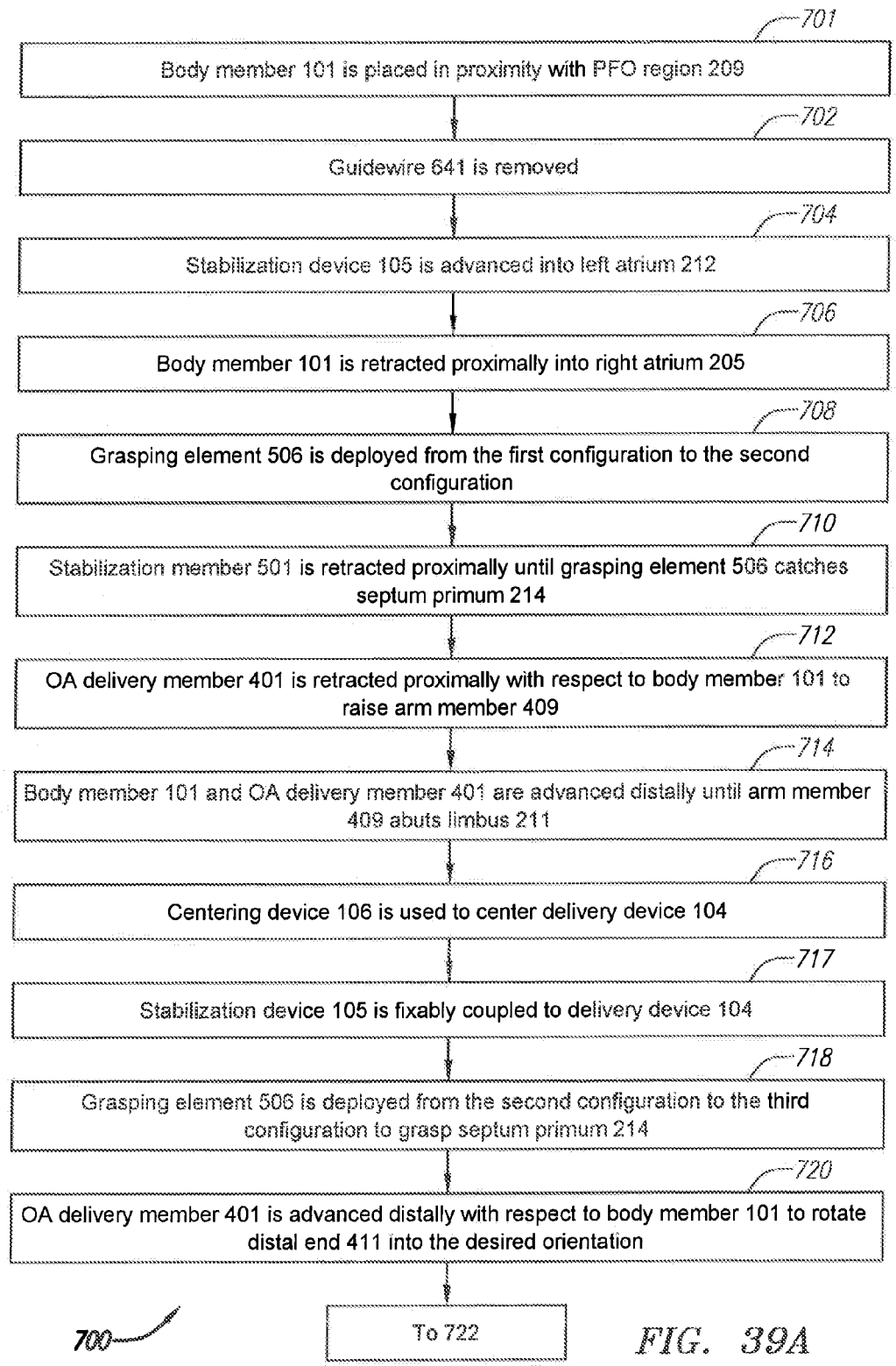

FIGS. 39A-B are flow diagrams depicting an example of method 700. First, at 701, body member 101 is placed in proximity with PFO region 209. As mentioned above, implant 103 can be delivered from left atrium 212 or right atrium 205. Preferably, implant 103 is placed into proximity with PFO region 209 by advancing body member 101 from the femoral vein to right atrium 205 in a conventional manner. For instance, in one example, a needle is inserted into the femoral vein and a guidewire is advanced through the needle into the femoral vein. The needle can then be removed and an access sheath can be routed over the guidewire, which can also then be removed. A J-tip guidewire, such as a 0.035"/0.038" guidewire, can be routed through the patient's vasculature into inferior vena cava 202 and right atrium 205. From there, the guidewire can be routed through PFO tunnel 215 and into left atrium 212. Next, an exchange sheath or multi-purpose guide can then be advanced over the S-tip guidewire into left atrium 212, at which point the J-tip guidewire can be removed. A relatively stiffer guidewire 641 can then be advanced through the exchange sheath or multi-purpose guide and into left atrium 212 and optionally the pulmonary vein, which can act as an anchor for the guidewire. Body member 101 can then be advanced over the guidewire 641 into proximity with PFO region 209, preferably through PFO tunnel 215 and into left atrium 212. In addition, a catheter or guidewire having a sizing device, such as a balloon, can be placed within PFO tunnel 215 to measure the size of PFO tunnel 215, for use in choosing a placement location, implant size, etc.

At 702, guidewire 641, if present, can be removed. At 704, stabilization device 105 is preferably advanced through lumen 631 and into left atrium 212. At 706, body member 101 can be retracted proximally into right atrium 205. Preferably, stabilization device 105 includes a stabilization member 501 and grasping device 502 with grasping element 506. At 708, grasping element 506 can be deployed from the first housed configuration to the second configuration for catching tissue, which, in this example, is preferably septum primum 214.

Next, at 710, stabilization member 501 is preferably moved distally until grasping element 506 catches septum primum 214. Then, at 712, OA delivery member 401 can be retracted proximally with respect to body member 101 to raise arm member 409. At 714, body member 101 and OA delivery member 401 are advanced distally until arm member 409 abuts limbus 211. At 716, centering device 106 can be used to center delivery device 104, preferably by deflecting centering arms 602. Once centered, if not already done so, at 717 stabilization device 105 can be fixably coupled to delivery device 104 (e.g., with a rotating hemostasis valve or Tuohy-Borst valve and the like). Next, at 718, grasping element 506 can be further deployed to the third configuration to grasp septum primum 214 and lock stabilization device 105 to septum primum 214. Alternatively, either 716, 717, 718 or any combination thereof can be implemented prior to 712. Also, 716-718 can be implemented in any order desired with respect to each other.

Once stabilized, centered and locked in place. OA delivery member 401 is preferably advanced distally with respect to body member 101 to rotate distal end 410 into the desired orientation with surface 320 of septum secundum 210. At 722, needle member 405 can be advanced through septum secundum 210 and septum primum 214 and into left atrium 212. Then, at 724, pusher member 406 can be advanced distally to at least partially deploy LA portion 302 of implant 103 from distal end 415 of needle member 405. In embodiments where centering arms 602 are in their deflected state for centering, it is possible for needle member 405 to pass between centering arms 602 and stabilization member 501 when inserted, based on needle insertion location 419. To avoid capture of implant 103 between centering arms 602 and stabilization member 501, centering arms 602 can be retracted proximally back into elongate body 101 thereby removing them from seats 604 and preventing implant 103 from being trapped between centering arms 602 and stabilization member 501. Next, at 726, grasping element 506 can be moved to the second configuration to free stabilization device 105 from septum primum 214. Alternatively, 726 can be performed before 724 if desired.

Then, at 728, LA portion 302 can be fully deployed if not already. At 730, grasping element 506 can be removed to the first configuration, housed within stabilization member 501. Next, at 732, centering device 106 can be moved to the undeployed configuration if not already, preferably by collapsing centering arms 602, after which stabilization device 105 can be retracted proximally from PFO entrance 217 at 734. At 736, needle member 405 can be withdrawn into OA delivery member 401 to deploy central portion 303 of implant 103 and at least a portion of RA portion 301. Here, at 738, an optional closure test can be performed to confirm at least partial closure, and preferably substantially complete closure, of PFO tunnel 215. Any desired closure test can be performed including, but not limited to, the introduction of gaseous bubbles simultaneously with imaging using contrast enhanced transcranial doppler (CE-TCD), intracardiac echocardiography (ICE) and the like, or the infusion of a radio-opaque dye imagable via flouroscopy. The test may be performed by pulling back OA delivery member 401 as far as necessary to deploy RA coil 301 and then test while device is at PFO entrance.

At 740, OA delivery member 401 can be retracted proximally with respect to body member 101 to complete deployment of RA portion 301, release limbus 211 and place OA delivery member 401 in the original position. If the desired degree of closure is confirmed, then any tether connection to implant 103 can be released at 742. Finally, at 744, body member 101 can be retracted distally and withdrawn from the patient.

Figure 40:
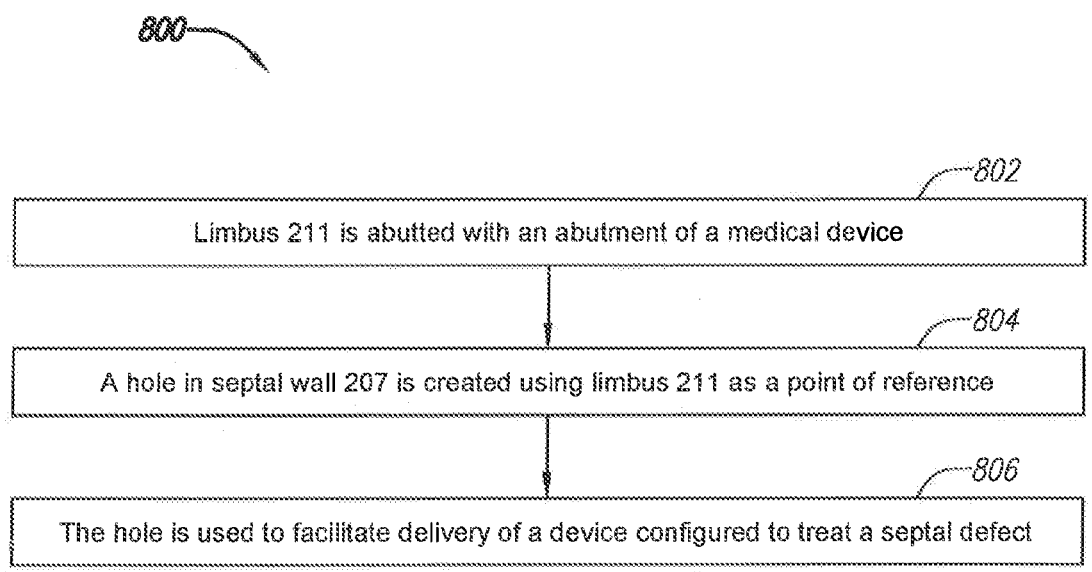
FIG. 40 is a flow diagram depicting another exemplary method of treating a septal defect.

FIG. 40 depicts another exemplary method 800 of treating a septal defect. At 802, limbus 211 is abutted with an abutment of a medical device. Preferably, limbus 211 is engaged with the medical device and optionally grasped such that the medical device is anchored to limbus 211. Then, at 804, a hole in septal wall 207, preferably in septum secundum 210, is created using limbus 211 as a point of reference. For instance, the hole can be created at a fixed or adjustable distance from limbus 211. At 806, the hole is used to facilitate delivery of a device configured to treat a septal defect. In one example, the device is deployed through the hole such that it causes at least partial closure of the septal defect. In this example of method 800, limbus 211 is abutted and used as a reference. In another example of method 800, the edge of septum primum 214 is abutted and used as a reference. In other examples of method 800, one or both sidewalls 219 and/or fossa ovalis 208 are abutted and used as points of reference.

It should be noted that any feature, function, method or component of any embodiment described with respect to FIGS. 1-40 can be used in combination with any other embodiment, whether or not described herein. As one of skill in the art will readily recognize, treatment system 100 and the methods for treating a septal defect can be configured or altered in an almost limitless number of ways, the many combinations and variations of which cannot be practically described herein.

The devices and methods herein may be used in any part of the body, in order to treat a variety of disease states. Of particular interest are applications within hollow organs including but not limited to the heart and blood vessels (arterial and venous), lungs and air passageways, digestive organs (esophagus, stomach, intestines, biliary tree, etc.). The devices and methods will also find use within the genitourinary tract in such areas as the bladder, urethra, ureters, and other areas.

Furthermore, the off-axis delivery systems may be used to pierce tissue and deliver medication, fillers, toxins, and the like in order to offer benefit to a patient. For instance, the device could be used to deliver bulking agent such as collagen, pyrolytic carbon beads, and/or various polymers to the urethra to treat urinary incontinence and other urologic conditions or to the lower esophagus/upper stomach to treat gastroesophageal reflux disease. Alternatively, the devices could be used to deliver drug or other agent to a preferred location or preferred depth within an organ. For example, various medications could be administered into the superficial or deeper areas of the esophagus to treat Barrett's esophagus, or into the heart to promote angiogenesis or myogenesis. Alternatively, the off-axis system can be useful in taking biopsies, both within the lumen and deep to the lumen. For example, the system could be used to take bronchoscopic biopsy specimens of lymph nodes that are located outside of the bronchial tree or flexible endoscopic biopsy specimens that are located outside the gastrointestinal tract. The above list is not meant to limit the scope of the invention.

In some embodiments, the off-axis delivery system is used with an anchoring means in order to anchor the device to a location within the body prior to rotation of the off-axis system. This anchoring means may involve the use of a tissue grasper or forceps. It should be noted that any device or set of devices can be advanced within the lumen of the off-axis delivery system, including but not limited to needles, biopsy forceps, aspiration catheters, drug infusion devices, brushes, stents, balloon catheters, drainage catheters, and the like.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit of the disclosure.

What is claimed is:

1. A method of treating a patent foramen ovale in septal tissue of a septal wall, the patent foramen ovale defined by a septum primum and a septum secundum with a tunnel separating them, comprising:

moving an elongate delivery device with respect to an elongate body member to position an open distal end of the elongate delivery device in proximity with the septal wall, wherein a grasping device is coupled with the elongate body member and the elongate delivery device, the elongate body member and elongate delivery device each being configured for insertion into the vasculature;

grasping opposite sides of the septum secundum with opposing members of a grasping device such that the opposing members are each in contact with an opposite side of the septum secundum, the opposing members being pivotally coupled together and being non-releasably coupled to the elongate delivery device, wherein a first one of the opposing members is a rigid arm-like member having a first end pivotally coupled with the elongate body member and a second end pivotally coupled with the elongate delivery device;

creating a hole through the septum secundum and septum primum, with a needle having a lumen which houses a closure device, while grasping the septum secundum; and deploying the closure device through the hole such that a first end of the closure device is in contact with the septum primum and a second end of the closure device is in contact with the septum secundum to at least partially close the tunnel.

2. The method of claim 1, wherein a second one of the opposing members is the elongate body member.

3. The method of claim 1, wherein the opposing members are pivotally coupled together with a hinge.

4. The method of claim 3, wherein the elongate delivery device comprises a rigid tubular distal tip, and wherein the second end of the arm-like member is pivotally coupled with the rigid tubular distal tip of the elongate delivery device by way of the hinge.

5. The method of claim 3, wherein the elongate body member comprises an elongate open channel extending along a length of the side of the elongate body member proximal to the hinge, the elongate open channel being configured to receive a side of the elongate delivery device.

6. The method of claim 5, wherein the elongate body member comprises a lumen having an open distal end located proximal to the elongate open channel, the elongate delivery device being slidably housed within the lumen.

7. The method of claim 1, further comprising, prior to grasping opposite sides of the septum secundum, moving the elongate delivery device with respect to the elongate body member to cause the arm-like member to pivot and move a distal region of the elongate delivery device relatively further away from the elongate body member.

8. The method of claim 3, wherein grasping opposite sides of the septum secundum comprises distally advancing the elongate delivery device with respect to the elongate body member such that at least a portion of a distal region of the elongate delivery device arcs outward away from the elongate body member and such that the septum secundum is grasped between the arm-like member and a second one of the opposing members.

9. The method of claim 8, wherein distally advancing the elongate delivery device with respect to the elongate body member causes the open distal end of the elongate delivery device to rotate about the hinge such that the open distal end is brought into an orientation that faces the septum secundum.

10. The method of claim 8, wherein distally advancing the elongate delivery device with respect to the elongate body member causes the open distal end of the elongate delivery device to rotate with respect to the arm member about the hinge such that the needle can be advanced along an axis normal to a right atrial surface of the septum secundum.

11. The method of claim 8, wherein, prior to moving the elongate delivery device with respect to the elongate body member to cause the arm-like member to pivot and move the distal region of the delivery device further away from the elongate body member, a longitudinal axis of the distal region of the elongate delivery device, measured at the distal end of the elongate delivery device, is substantially parallel to a longitudinal axis of a distal region of the elongate body member and is not substantially parallel to an axis normal to the surface of the septum secundum.

12. The method of claim 11, wherein distally advancing the elongate delivery device further with respect to the elongate body member to cause the distal region of the elongate delivery device to arc outwards away from the elongate body member also causes the longitudinal axis of the distal region of the elongate delivery device to move transverse to the longitudinal axis of the distal region of the elongate body member.

13. The method of claim 11, wherein distally advancing the delivery device further with respect to the body member to cause the distal region of the delivery device to arc outwards away from the body member also causes the longitudinal axis of the distal region of the delivery device to move approximately perpendicular to the longitudinal axis of the distal region of the body member.

14. The method of claim 11, wherein distally advancing the elongate delivery device further with respect to the elongate body member to cause the distal region of the elongate delivery device to arc outwards away from the elongate body member also causes the longitudinal axis of the distal region of the elongate delivery device to move substantially parallel to an axis normal to the surface of the septum secundum.

15. The method of claim 1, further comprising:
   expanding a centering device within the tunnel; and
   centering the needle with respect to a first and second sidewall of the tunnel prior to creating the hole.

* * * * *